(12) United States Patent
Braun et al.

(10) Patent No.: US 7,947,834 B2
(45) Date of Patent: May 24, 2011

(54) SUBSTITUTED QUINOXALINES, THEIR PREPARATION AND THEIR THERAPEUTICAL USE AS 11βHSD1 MODULATORS

(75) Inventors: Alain Braun, Antony (FR); Patrick Mougenot, Antony (FR); Claudie Namane, Antony (FR); Eric Nicolai, Antony (FR); Francois Pacquet, Antony (FR); Christophe Philippo, Antony (FR); Olivier Venier, Antony (FR); Olivier Crespin, Antony (FR); Cecile Pascal, Antony (FR); Michel Aletru, Antony (FR); Stefan Gussregen, Wiesbaden (DE)

(73) Assignee: Sanofi-Aventis, Paris (FR)

(*) Notice: Subject to any disclaimer, the term of this patent is extended or adjusted under 35 U.S.C. 154(b) by 0 days.

(21) Appl. No.: 12/337,967

(22) Filed: Dec. 18, 2008

(65) Prior Publication Data
US 2009/0176775 A1    Jul. 9, 2009

Related U.S. Application Data

(63) Continuation of application No. PCT/FR2007/001069, filed on Jun. 26, 2007.

(30) Foreign Application Priority Data

Jun. 27, 2006  (FR) .................................. 06 05786
Dec. 22, 2006  (FR) .................................. 06 11239

(51) Int. Cl.
C07D 241/36          (2006.01)
(52) U.S. Cl. ........................ 544/355; 546/245; 548/530
(58) Field of Classification Search .................. 544/355; 546/245; 548/530
See application file for complete search history.

(56) References Cited

U.S. PATENT DOCUMENTS 6,369,057 B1 *  4/2002  Billhardt et al. ............ 514/234.8

FOREIGN PATENT DOCUMENTS

| EP | 0130795 | 1/1985 |
|---|---|---|
| EP | 1283199 | 2/2003 |
| WO | WO 92/22552 | 12/1992 |
| WO | WO 03/031436 | 4/2003 |
| WO | WO 03/106456 | 12/2003 |
| WO | WO 2004/033427 | 4/2004 |
| WO | WO 2004/089896 | 10/2004 |
| WO | WO 2005/047250 | 5/2005 |
| WO | WO 2006/053024 | 5/2006 |
| WO | WO 2006/055752 | 5/2006 |
| WO | WO 2006/105127 | 10/2006 |
| WO | WO 2006/132436 | 12/2006 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Gilbert, A. M., et. al., Modulation of Selective Serotonin Reuptake Inhibitor and 5-HT1A Antagonist Activity in 8-Aza-Bicyclo[3.2.1.]Octane Derivatives of 2,3-Dihydro-1,4-Benzodioxane, Bioorganic & Medicinal Chemistry Letters, vol. 14, (2004), pp. 515-518.

Lu, Z., et. al., Substituted Bridged Phenyl Piperidines: Orally Active Growth Hormone Secretagogues, Bioorganic & Medicinal Chemistry Letters, vol. 13, (2003), pp. 1817-1820.
Sikazwe, D. M. N., et. al.,, Haloperidol: Toward Further Understanding of the Structural Contributions of its Pharmacophoric Elements at D2-Like Receptors, Bioorganic & Medicinal Chemistry Letters, vol. 14, (2004), pp. 5739-5742.
Andrews, R. C., et. al., Effects of the 11B-Hydroxysteroid Dehydrogenase Inhibitor Carbenoxolone on Insulin Sensitivity in Men with Type 2 Diabetes, The Journal of Clinical Endocrinology & Metabolism, vol. 88, No. 1, pp. 285-291, (2003).
Barf, T. et. al., Arylsulfonamidothiazoles as a New Class of Potential Antidiabetic Drugs. Discovery of Potent and Selective Inhibitors of the 11 Beta-Hydroxysteroid Dehydrogenase Type 1, American Chemical Society, (2002), vol. 45, No. 18, pp. 3813-3815.
Buffat, M. G. P., et. al., Synthesis of Piperidines, Tetrahedron, vol. 60, (2004), pp. 1701-1709.
Cooper, M. S., et. al., Expression and Functional Consequences of 11B-Hydroxysteroid Dehydrogenase Activity in Human Bone, Bone, vol. 27, No. 3, (2000), pp. 375-381.
Coudert, G., et. al., A New Synthesis of 3,4-Dihydro-2H-1, 4-Benzoxazines Using Solid-Liquid Phase-Transfer Catalysis, Synthesis, vol. 7, pp. 541-543, (1979). Davani, B., et. al., Type 1 11B-Hydroxysteroid Dehydrogenase Mediates Glucocorticoid Activation and Insulin Release in Pancreatic Islets , The Journal of Biological Chemistry, vol. 275, No. 45, pp. 34841-34844, (2000).
Grzyb, J. A., et. al., Carbamoylimidazolium and Thiocarbamoylimidazolium Salts: Novel Reagents for the Synthesis of Ureas, Thioureas, Carbamates, Thiocarbamates and Amides, Tetrehedron 61, 30 (2005) pp. 7153-7175.
Hermanowski-Vosatka, A., et. al., 11B-HSD1 Inhibition Ameliorates Metabolic Syndrome and Prevents Progresion of Atherosclerosis in Mice, J. Exp. Med., vol. 202, pp. 517-527, (2005).
Kotelevtsev, Y., et. al., 11B-Hydroxysteroid Dehydrogenase Type 1 Knockout Mice Show Attenuated Glucocorticoid-Inducible Responses and Resist Hyperglycemia on Obesity or Stress, Proc. Natl. Acad. Sci. USA, vol. 94, pp. 14924-14929, (1997).
Kuwabe, S., et. al., Palladium-Catalyzed Intramolecular C-O Bond Formation, J. Am. Chem. Soc. (2001), vol. 123, pp. 12202-12206.
Laschat, S., et. al., Stereoselective Synthesis of Piperidines, Synthesis (2000), vol. 13, pp. 1781-1813.

(Continued)

Primary Examiner — James O Wilson
Assistant Examiner — Douglas M Willis
(74) Attorney, Agent, or Firm — Jiang Lin, Esq.; Scully, Scott, Murphy & Presser, P.C.

(57) ABSTRACT

The present invention is related to a compound of formula (I):

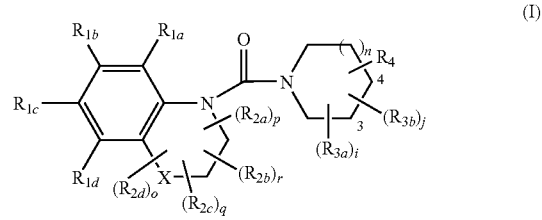

wherein i, j, n, o, p, q, r, $R_{1a}$, $R_{1b}$, $R_{1c}$, $R_{1d}$, $R_{2a}$, $R_{2b}$, $R_{2c}$, $R_{2d}$, $R_{3a}$, $R_{3b}$ and $R_4$ are as defined herein, or an addition salt with an acid thereof, or a hydrate or solvate thereof, its preparation, pharmaceutical composition, and uses for treating a disease in which the enzyme 11β-HSD1 is involved.

13 Claims, No Drawings

OTHER PUBLICATIONS

Lupien, S. J., et. al., Cortisol Levels During Human Aging Predict Hippocampal Atrophy and Memory Deficits, Nat. Neurosci., vol. 1, pp. 69-73, (1998).

Masuzaki, H., et. al., A Transgenic Model of Visceral Obesity and The Metabolic Syndrome, Science, vol. 294, pp. 2166, (2001).

Masuzaki, H., et. al., Transgenic Amplification of Glucocorticoid Action in Adipose Tissue Causes High Blood Pressure in Mice, J. Clinical Invest., vol. 112, pp. 83-90, (2003).

Matsuzawa, Y., et. al., Molecular Mechanism of Metabolic Syndrome X: Contribution of Adipocytokines Adipocyte-derived Bioactive Substances, Acad. Sci. vol. 892, pp. 146-154, (1999).

McEwen, B. S., et. al., Stress and Cognitive Function, Curr. Opin. Neurobiol., vol. 5, pp. 205-216, (1995).

Moisan, M-P., et. al., 11B-Hydroxysteroid Dehydrogenase Bioactivity and Messenger RNA Expression in Rat Forebrain: Localization in Hypothalamus, Hippocampus, and Cortex, Endocrinology, vol. 127, pp. 1450-1455, (1990).

Rauz, S., et. al., Expression and Putative Role of 11B-Hydroxysteroid Dehydrogenase Isozymes within the Human Eye, Invest. Ophtamol. Vis. Sci., vol. 42, pp. 2037-2042, (2001).

Reaven, G. M., et. al., Role of Insulin Resistance in Human Disease (Syndrome X): An Expanded Definition, Ann. Rev. Med., vol. 44, pp. 121-134, (1993).

Rocha, B. A., et. al., 11beta-Hydroxsteroid Dehydrogenase Type 1 (11 beta-HSD1) Inhibition Prolonged Memory Retention in Mice, Abstract 231 ACS Meeting, Atlanta Mar. 26-30, 2006.

Sandeep, T. C., et. al., 11B-Hydrosteroid Dehydrogenase Inhibition Improves Cognitive Function in Healthy Elderly Men and Type 2 Diabetics, Proc. Natl. Acad. Sci., vol. 101, pp. 6734-6738, (2004).

Shankaran, K., et. al., Syntheses and SAR Studies of 4-(Heteroarylpiperdin-1-yl-Methyl)-Pyrrolidin-1-yl-Acetic Acid Antagonists of the Human CCR5 Chemokine Receptor, Bioorganic & Medicinal Chemistry Letters, vol. 14, (2004), pp. 3419-3424.

Stokes, J., et. al., Distribution of Glucorticoid and Mineralocorticoid Receptors and 11B-Hydroxysteroid Dehydrogenases in Human and Rat Ocular Tissues, Invest. Ophthalmol. Vis. Sci., vol. 41, pp. 1629-1638, (2000).

Terao, Y., et. al., Trifluoroacetic Acid-Catalyzed 1,3-Cycloaddition of the Simplest Iminium Ylide Leading to 3-or 3,4-Substituted Pyrrolidines and 2,5-Dihydropyrroles, Chem. Pharm. Bull. (1985), vol. 33, No. 7, pp. 2762-2766.

Tomlinson, J. W., et. al., 11B-Hydroxysteroid Dehydrogenase Type 1: A Tissue-Specific Regulator of Glucocorticoid Response, Endocrine Reviews, vol. 25, No. 3, pp. 831-866 (2004).

Wajchenberg, B. L., et. al., Subcutaneous and Visceral Adipose Tissue: Their Relation to the Metabolic Syndrome, Endocrine Reviews, vol. 21, No. 6, pp. 697-738, (2000).

Wang, S. J. Y., et. al., Inhibition of 11B-Hydroxysteroid Dehydrogenase Type1 Reduces Food Intake and Weight Gain but Maintains Energy Expenditure in Diet-Induced Obese Mice, Diabetologia, (2006), vol. 49, pp. 1333-1337.

Yau, J. L. W., et. al., Lack of Tissue Glucocorticoid Reactivation in 11B-Hydroxysteroid Dehydrogenase Type 1 Knockout Mice Ameliorates Age-Related Learning Impairments, Proc. Natl. Acad. Sci., vol. 98, pp. 4716-4721, (2001).

* cited by examiner

SUBSTITUTED QUINOXALINES, THEIR PREPARATION AND THEIR THERAPEUTICAL USE AS 11βHSD1 MODULATORS

The present application is a Continuation of International Application No. PCT/FR2007/001069, filed Jun. 26, 2007, which is incorporated herein by reference in its entirety.

FIELD OF THE INVENTION

The present invention relates to piperidine or pyrrolidine urea derivatives, to their preparation and to their therapeutic application. The present compounds modulate the activity of 11β-hydroxysteroid dehydrogenase type 1 (11βHSD1) and are of use in the treatment of pathologies in which such a modulation is beneficial, as in the case of metabolic syndrome or non-insulin-dependent type 2 diabetes.

BACKGROUND OF THE INVENTION

11β-Hydroxysteroid dehydrogenase type 1 (11βHSD1) locally catalyzes the conversion of inactive glucocorticoids (cortisone in man) to active glucocorticoids (cortisol in man) in various tissues and organs, mainly the liver and the adipose tissue, but also in the muscles, bones, pancreas, endothelium, ocular tissue and in some parts of the central nervous system. 11βHSD1 acts as a regulator of the action of the glucocorticoids in the tissues and organs where it is expressed (Tomlinson et al., *Endocrine Reviews*, 25(5), 831-866 (2004), Davani et al., *J. Biol. Chem.*, 275, 34841 (2000); Moisan et al., *Endocrinology*, 127, 1450 (1990)).

The most important pathologies in which glucocorticoids and inhibition of 11βHSD1 are involved are shown below.

A. Obesity, Type 2 Diabetes and Metabolic Syndrome

The role of 11βHSD1 in obesity, type 2 diabetes and metabolic syndrome (also known under the name of syndrome X or insulin resistance syndrome) where the symptoms include visceral obesity, glucose intolerance, insulin resistance, hypertension, type 2 diabetes and hyperlipidaemia (*Reaven Ann. Rev. Med.*, 44, 121 (1993)) is described in numerous publications. In man, the treatment with carbenoxolone (a non-specific inhibitor of 11βHSD1) improves the insulin sensitivity in thin voluntary patients and in type 2 diabetics (Andrews et al., *J. Clin. Endocrinol. Metab.*, 88, 285 (2003)). Furthermore, the mice whose 11βHSD1 gene has been switched off are resistant to the hyperglycemia induced by stress and obesity, show an attenuation of the induction of hepatic enzymes of gluconeogenesis (PEPCK and G6P) and exhibit an increase in insulin sensitivity in the adipose tissue (Kotelevstev et al., *Proc. Nat. Acad. Sci.*, 94, 14924 (1997); Morton et al., *J. Biol. Chem.*, 276, 41293 (2001)). Furthermore, transgenic mice where the 11βHSD1 gene has been overexpressed in the adipose tissues exhibit a phenotype similar to that of human metabolic syndrome (Masuzaki et al., *Science*, 294, 2166 (2001)). It should be noted that the phenotype observed exists without an increase in the total of the circulating glucocorticoids but is induced by the specific increase in active glucocorticoids in the adipose deposits.

Furthermore, novel categories of specific 11βHSD1 inhibitors have recently appeared:

arylsulfonamidothiazoles have shown that they improve insulin sensitivity and reduce the level of glucose in the blood of mice exhibiting hyperglycemia (Barf et al., *J. Med. Chem.*, 45, 3813 (2002)). Furthermore, in a recent study, it has been shown that compounds of this type reduce food intake and the increase in weight by obese mice (Wang et al., *Diabetologia*, 49, 1333 (2006)).

triazoles have shown that they improve the metabolic syndrome and slow down the progression of atherosclerosis in mice (Hermanowski-Vosatka et al., *J. Exp. Med.*, 202, 517 (2005)).

B. Cognition and Dementia

Mild cognitive problems are common phenomena in elderly people and can result finally in progression to dementia. Both in the case of elderly animals and of elderly humans, the differences in individuals for the general cognitive functions have been related to the differences in long-term exposure to glucocorticoids (Lupien et al., *Nat. Neurosci.*, 1, 69 (1998)). Furthermore, the deregulation of the HPA (hypothalamic-pituitary-adrenal) axis resulting in the chronic exposure to glucocorticoids of certain subregions of the brain has been proposed as contributing to the decline in the cognitive functions (McEwen et al., *Curr. Opin. Neurobiol.*, 5, 205, 1995). 11βHSD1 is abundant in the brain and is expressed in numerous subregions, including the hypothalamus, the frontal cortex and the cerebellum (Sandeep et al., *Proc. Natl. Acad. Sci.*, 101, 6734 (2004)). Mice deficient in 11βHSD1 are protected against the dysfunctionings of the hypothalamus associated with glucocorticoids which are related to old age (Yau et al., *Proc. Nat. Acad. Sci.*, 98, 4716, (2001)). Furthermore, in studies in man, it has been shown that the administration of carbenoxolone improves verbal fluidity and verbal memory in elderly people (Yau et al., *Proc. Natl. Acad. Sci.*, 98, 4716 (2001), Sandeep et al., *Proc. Natl. Acad. Sci.*, 101, 6734 (2004)). Finally, the use of selective 11βHSD1 inhibitors of triazole type has shown that they extend the retention of memory in elderly mice (Rocha et al., Abstract 231 ACS Meeting, Atlanta, 26-30 Mar. 2006).

C. Intraocular Pressure

Glucocorticoids can be used by the topical route or systemic route for a great variety of pathologies of clinical opthalmology. A particular complication of these treatments is the glaucoma induced by the use of corticosteroids. This pathology is characterized by the increase in the intraocular pressure (IOP). In the most severe cases and for the untreated forms, the IOP can result in partial loss of field of vision and possibly in complete loss of vision. The IOP is the result of an imbalance between the production of aqueous humor and its drainage. The aqueous humor is produced in the nonpigmented epithelial cells and the drainage is carried out through these cells of the trabecular network. The 11βHSD1 is located in the nonpigmented epithelial calls and its function is clearly the amplification of the activity of the glucocorticoids in these cells (Stokes et al., *Invest. Opthalmol. Vis. Sci.*, 41, 1629 (2000)). This notion is confirmed by the observation that the concentration of free cortisol is in high excess with respect to the cortisone in the aqueous humor (ratio 14/1). The functional activity of 11βHSD1 in the eyes was evaluated by studying the action of carbenoxolone in healthy volunteers. After treating with carbenoxolone for seven days, the IOP is reduced by 18% (Rauz et al., *Invest. Ophtamol. Vis. Sci.*, 42, 2037 (2001)). The inhibition of 11βHSD1 in the eyes is thus predicted as reducing the local concentration of glucocorticoids and the IOP, producing a beneficial effect in the treatment of glaucoma and other disorders of vision.

D. Hypertension

The hypertensive substances resulting from the adipocytes, such as leptin and angiotensinogen, have been proposed as being key components in the hypertension pathologies related to obesity (Wajchenberg et al., *Endocr. Rev.*, 21, 697 (2000)). Leptin, which is secreted in excess in transgenic aP2-11βHSD1 mice (Masuzaki et al., *J. Clinical Invest.*, 112, 83 (2003)), can activate various networks of sympathetic neuronal systems, including those which regulate the arterial pressure (Matsuzawa et al., *Acad. Sci.*, 892, 146 (1999)). Furthermore, the renin-angiotensin system (RAS) has been identified as being a determining route in the variation in arterial pressure. Angiotensinogen, which is produced in the liver and the adipose tissue, is a key substrate for renin and is the cause of the activation of the RAS. The plasma angiotensinogen level is significantly elevated in transgenic aP2-11βHSD1 mice, as are those of angiotensin II and of aldosterone (Masuzaki et al., *J. Clinical Invest.*, 112, 83 (2003)); these components result in the elevation of the arterial pressure. The treatment of these mice with low doses of an angiotensin II receptor antagonist does away with this hypertension (Masuzaki et al., *J. Clinical Invest.*, 112, 83 (2003)). These items of information illustrate the importance of the local activation of the glucocorticoids in the adipose tissue and the liver and suggest that this hypertension can be caused or exacerbated by the activity of 11βHSD1 in these tissues. The inhibition of 11βHSD1 and the reduction in the level of glucocorticoids in the adipose tissue and/or in the liver is thus predicted as having a beneficial role in the treatment of hypertension and the associated cardiovascular pathologies.

E. Osteoporosis

The development of the skeleton and the bone functions are also regulated by the action of the glucocorticoids. 11βHSD1 is present in the osteoclasts and osteoblasts. The treatment of healthy volunteers with carbenoxolone has shown a reduction in the bone resorption markers without change in the bone formation markers (Cooper et al., Bone, 27, 375 (2000)). The inhibition of 11βHSD1 and the reduction in the level of glucocorticoids in the bones might thus be used as a protective mechanism in the treatment of osteoporosis.

Piperidine or pyrrolidine urea derivatives which modulate the activity of 11βHSD1 have now been found.

SUMMARY OF THE INVENTION

A subject matter of the present invention is compounds corresponding to the formula (I):

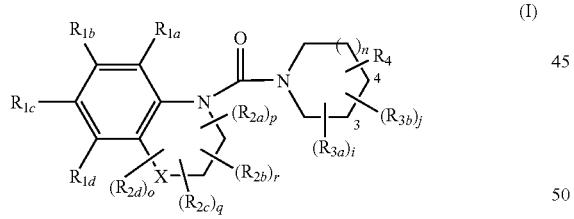

in which:

X represents either a carbon, oxygen, sulfur or nitrogen atom or the group

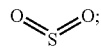

$R_{1a,b,c,d}$ and $R_{2a,b,c,d}$, which are identical or different, each represent a hydrogen or halogen atom, a $(C_1-C_5)$alkyl, $(C_1-C_5)$alkoxy, $(C_1-C_5)$haloalkyl, hydroxyl, hydroxy$(C_1-C_5)$alkyl or cyano group, a —$COOR_5$ group, an —$NR_6R_7$ group, a $COOR_5$—$(C_1-C_5)$alkyl group, an $NR_6R_7$—$(C_1-C_5)$alkyl group, a —$CONR_6R_7$ group, a $CONR_6R_7$—$(C_1-C_5)$alkyl group, an —$SO_2NR_6R_7$ group, a —$COR_5$ group or an aryl or heteroaryl, aryl$(C_1-C_5)$alkyl, heteroaryl$(C_1-C_5)$alkyl or heterocycloalkyl $(C_1-C_5)$alkyl group, it being possible for all the aryl or heteroaryl groups optionally to be substituted by 1 to 3 substituents chosen from cyano, $COOR_5$, $CONR_6R_7$, $SO_2R_5$, $(C_1-C_5)$alkoxy or $OCH_2CONR_6R_7$ groups, a halogen atom, $(C_1-C_5)$haloalkyl and only one aryl$(C_1-C_5)$alkyl group can optionally be substituted by a heteroaryl group, or $(R_{2a})$ or $(R_{2b})$ can also form, with the carbon atom to which they are attached, a C=O, C=CF$_2$ group, or $(R_{2a})$ and/or $(R_{2b})$ can also form, with the atom or atoms to which they are attached, a $(C_3-C_6)$cycloalkyl group, it being possible for these rings to be spiro when they are carried by the same carbon atom and to be optionally substituted by one to three halogen atoms, or $(R_{1d})$ and $(R_{2a})$ can also form, with the atoms to which they are attached, a $(C_3-C_7)$cycloalkyl group;

the $R_{3a,b}$ groups each represent a hydrogen atom, a fluorine atom or a $(C_1-C_5)$alkyl, $(C_1-C_5)$alkoxy, alkoxy$(C_1-C_5)$alkyl, hydroxyl, hydroxy$(C_1-C_5)$alkyl, $(C_1-C_5)$haloalkyl or cyano group, a —$COOR_5$ group, an —$NR_6R_7$ group, a $COOR_5$—$(C_1-C_5)$alkyl group, an $NR_6R_7$—$(C_1-C_5)$alkyl group, a —$CONR_6R_7$ group or a $CONR_6R_7$—$(C_1-C_5)$alkyl group, $R_4$ represents:
a $(C_1-C_5)$alkyl group;
a $(C_3-C_6)$cycloalkyl group;
a heterocycloalkyl group,
a mono- or bicyclic aryl group having from 5 to 10 carbon atoms;
a mono- or bicyclic heteroaryl group having from 2 to 9 carbon atoms;

when $R_4$ is an aryl or heteroaryl or heterocycloalkyl group, it can optionally be substituted by 1 to 4 substituents chosen from halogen atoms, $(C_1-C_5)$alkyl, $(C_1-C_5)$alkoxy, $(C_1-C_5)$haloalkyl, hydroxyl, hydroxy$(C_1-C_5)$alkyl, $(C_1-C_5)$alkoxy$(C_1-C_5)$alkyl, cyano, optionally substituted phenyl, optionally substituted benzyl, —$COOR_5$ or —$NR_6R_7$ groups, a —$COOR_5$—$(C_1-C_5)$alkyl group, an —$NR_6R_7$—$(C_1-C_5)$alkyl group, a —$CONR_6R_7$ group or an —$SO_2NR_6R_7$ group, where $R_{3a,b}$ and $R_4$ are either carried by different carbon atoms or are carried by the same carbon atom and, when they are carried by the same carbon atom, can together form a ring in the spiro position, in particular a ring of formula a), b), c) or d):

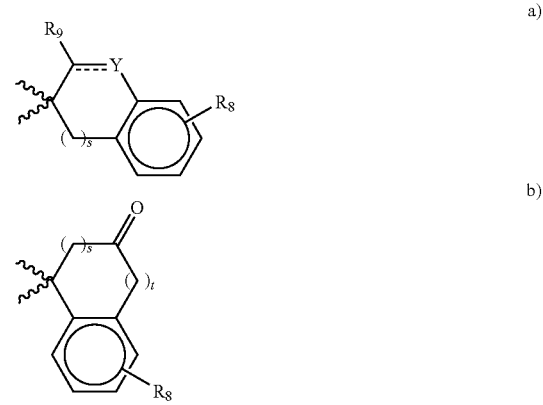

-continued

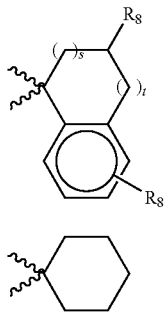

c)

d)

in which:
- ---- is a single bond or a double bond;
- s is an integer equal to 0, 1, 2 or 3;
- t is an integer equal to 0, 1, 2 or 3, it not being possible for s and t to be equal at the same time to 0;
- $R_8$ represents a hydrogen or halogen atom, a $(C_1-C_5)$ alkyl, $(C_1-C_5)$alkoxy, trifluoromethyl, hydroxyl, hydroxymethyl or cyano group, a —COOR$_5$ group or an —NR$_6$R$_7$ group;
- $R_9$ represents a hydrogen atom or a $(C_1-C_5)$alkyl or hydroxyl group;
- Y represents a bond or a carbon or nitrogen atom;
- n is an integer equal to 0 or 1;
- o, p, q and r, which are identical or different, are integers equal to 0, 1 or 2;
- i and j are integers equal to 0, 1, 2, 3 or 4;
- $R_5$ represents a hydrogen atom, a $(C_1-C_5)$alkyl group or a $(C_3-C_6)$cycloalkyl or halo$(C_1-C_5)$alkyl group;
- $R_6$ and $R_7$, which are identical or different, each represent a hydrogen atom, a $(C_1-C_5)$alkyl group, a $(C_3-C_6)$cycloalkyl, $(C_1-C_5)$alkylcarbonyl, hydroxymethyl$(C_1-C_5)$alkyl or $(C_1-C_5)$alkoxymethyl$(C_1-C_5)$alkyl group, an aryl group, an optionally substituted heterocycloalkyl group or an —SO$_2$R$_5$ group or can form, together with the nitrogen atom to which they are attached, an optionally substituted heterocycloalkyl, it being understood that, when X=CH$_2$, n=0, $R_{1a,b,c,d}$=H, $R_{2a,b,c,d}$=H and $R_{3a,b}$=H, then the $R_4$ group has to be other than phenyl optionally substituted by a halogen atom or a $(C_1-C_5)$alkyl, trifluoromethyl or $(C_1-C_5)$alkoxy group.

DETAILED DESCRIPTION OF THE INVENTION

The compounds of formula (I) can comprise one or more asymmetric carbon atoms. They can thus exist in the form of enantiomers or of diastereoisomers. These enantiomers or diastereoisomers and their mixtures, including the racemic mixtures, form part of the invention.

The compounds of formula (I) can exist in the form of bases or salified by acids or bases, in particular pharmaceutically acceptable acids or bases. Such addition salts form part of the invention.

These salts are advantageously prepared with pharmaceutically acceptable acids but the salts of other acids of use, for example, in the purification or the isolation of the compounds of formula (I) also form part of the invention.

The compounds of formula (I) can also exist in the form of hydrates or of solvates, mainly in the form of combinations or associations with one or more molecules of water or with of a solvent. Such hydrates and solvates also form part of the invention.

In the context of the present invention, and unless otherwise mentioned in the text:
- halogen atom is understood to mean: a fluorine, a chlorine, a bromine or an iodine;
- a $(C_1-C_5)$alkyl group is understood to mean: a saturated, linear or branched, aliphatic group having from 1 to 5 successive carbon atoms. Mention may be made, by way of examples, of the methyl, ethyl, propyl, isopropyl, butyl, isobutyl, tert-butyl and pentyl groups, and the like;
- a $(C_3-C_6)$cycloalkyl group is understood to mean: a cyclic alkyl group having from 3 to 6 carbon atoms. Mention may be made, by way of examples, of the cyclopropyl, methylcyclopropyl, cyclobutyl, cyclopentyl and cyclohexyl groups, and the like;
- a $(C_1-C_5)$alkoxy group is understood to mean: an —O—$(C_1-C_5)$alkyl radical where the $(C_1-C_5)$alkyl group is as defined above;
- an aryl group is understood to mean: a mono- or bicyclic aromatic group comprising between 5 and 10 carbon atoms. Mention may be made, as examples of aryl groups, of the phenyl group, the thiophene group, the furan group or the naphthalene group;
- a heteroaryl group is understood to mean: a mono- or bicyclic aromatic group comprising between 5 and 9 carbon atoms and comprising between 1 and 3 heteroatoms, such as nitrogen, oxygen or sulfur. Mention may be made, as examples of heteroaryl groups, of the groups:
  - pyridine
  - pyrazine
  - pyrimidine
  - pyrazole
  - oxadiazole
  - thiazole
  - imidazole;
- a $(C_1-C_5)$haloalkyl group is understood to mean: a $(C_1-C_5)$alkyl group as defined above substituted by 1 to 5 halogen atoms. Mention will be made, for example, of the fluoromethyl, difluoromethyl, trifluoromethyl, trichloromethyl or pentafluoroethyl groups;
- a heterocycloalkyl group is understood to mean: an optionally fused or bridged ring comprising from 4 to 9 atoms, at least one of which is chosen from oxygen, nitrogen or sulfur atoms. Mention may be made, by way of examples, of the morpholine, piperidine, pyrrolidine or piperazine groups;
- an "optionally substituted phenyl" or "optionally substituted benzyl" group is understood to mean: a phenyl or benzyl group which is optionally substituted by one or more of the following groups: halogen atoms or $(C_1-C_5)$alkyl, $(C_1-C_5)$alkoxy, $(C_1-C_5)$haloalkyl, hydroxyl, hydroxy$(C_1-C_5)$alkyl, $(C_1-C_5)$alkoxy$(C_1-C_5)$alkyl, cyano, phenyl, benzyl, —COOR$_5$, —NR$_6$R$_7$, COOR$_5$ $(C_1-C_5)$alkyl, NR$_6$R$_7$$(C_1-C_5)$alkyl, —CONR$_6$R$_7$, —SO$_2$NR$_6$R$_7$ or CONR$_6$R$_7$$(C_1-C_5)$alkyl groups;
- $R_{1a,b,c,d}$ denotes the $R_{1a}$, $R_{1b}$, $R_{1c}$ and $R_{1d}$ groups; $R_{2a,b,c,d}$ denotes the $R_{2a}$, $R_{2b}$, $R_{2c}$ and $R_{2d}$ groups; $R_{3a,b}$ denotes the $R_{3a}$ and $R_{3b}$ groups;
- $(R_{2a})_p$ denotes a number p of $R_{2a}$ groups carried by the same atom or by different atoms, $(R_{2b})_r$ denotes a number r of $R_{2b}$ groups carried by the same atom or by different atoms, $(R_{2c})_q$ denotes a number q of $R_{2c}$ groups carried by the same atom or by different atoms, $(R_{2d})_o$ denotes a number o of $R_{2d}$ groups carried by the same atom or by different atoms, $(R_{3a})_i$ denotes a number i of $R_{3a}$ groups carried by the same atom or by different atoms and $(R_{3b})_j$ denotes a number j of $R_{3b}$ groups carried by the same atom or by different atoms;

a group of "functional group-$(C_1$-$C_5)$alkyl" type, such as alkoxy$(C_1$-$C_5)$alkyl, hydroxy$(C_1$-$C_5)$alkyl, $COOR_5$—$(C_1$-$C_5)$alkyl, $NR_6R_7$—$(C_1$-$C_5)$alkyl or $CONR_6R_7$—$(C_1$-$C_5)$alkyl, or aryl$(C_1$-$C_5)$alkyl, heteroaryl$(C_1$-$C_5)$alkyl or heterocycloalkyl$(C_1$-$C_5)$alkyl type denotes a group having a linear or branched alkylene group having from 1 to 5 successive carbon atoms, i.e., respectively, —$(CH_2)_k$—$(C_1$-$C_5)$alkoxy, —$(CH_2)_k$—OH, —$(CH_2)_k$—$COOR_5$, —$(CH_2)_k$—$NR_6R_7$, —$(CH_2)_k$—$CONR_6R_7$, —$(CH_2)_k$-aryl, —$(CH_2)_k$-heteroaryl or —$(CH_2)_k$-heterocycloalkyl with k an integer from 1 to 5.

Mention may be made, among the compounds of formula (I) according to the invention, of the compounds for which:

X represents either a carbon, oxygen, sulfur or nitrogen atom or the group

$R_{1a,b,c,d}$ and $R_{2a,b,c,d}$, which are identical or different, each represent a hydrogen or halogen atom, a $(C_1$-$C_5)$alkyl, $(C_1$-$C_5)$alkoxy, $(C_1$-$C_5)$haloalkyl, hydroxyl, hydroxy $(C_1$-$C_5)$alkyl or cyano group, a —$COOR_5$ group, an —$NR_6R_7$ group, a $COOR_5$—$(C_1$-$C_5)$alkyl group, an $NR_6R_7$—$(C_1$-$C_5)$alkyl group, a —$CONR_6R_7$ group, a $CONR_6R_7$—$(C_1$-$C_5)$alkyl group, an —$SO_2NR_6R_7$ group, a —$COR_5$ group or an aryl or heteroaryl, aryl$(C_1$-$C_5)$alkyl, heteroaryl$(C_1$-$C_5)$alkyl or heterocycloalkyl$(C_1$-$C_5)$alkyl group, it being possible for all the aryl or heteroaryl groups optionally to be substituted by cyano, $COOR_5$ or $CONR_6R_7$ groups, or $(R_{2a})$ or $(R_{2b})$ can also form, with the carbon atom to which they are attached, a C=O group, or $(R_{2a})$ and/or $(R_{2b})$ can also form, with the atom or atoms to which they are attached, a $(C_3$-$C_6)$cycloalkyl group, it being possible for these rings to be spiro when they are carried by the same carbon atom, or $(R_{1d})$ and $(R_{2a})$ can also form, with the atoms to which they are attached, a $(C_3$-$C_7)$cycloalkyl group;

the $R_{3a,b}$ groups each represent a hydrogen atom, a fluorine atom or a $(C_1$-$C_5)$alkyl, $(C_1$-$C_5)$alkoxy, alkoxy$(C_1$-$C_5)$alkyl, hydroxyl, hydroxy$(C_1$-$C_5)$alkyl, $(C_1$-$C_5)$haloalkyl or cyano group, a —$COOR_5$ group, an —$NR_6R_7$ group, a $COOR_5$—$(C_1$-$C_5)$alkyl group, an $NR_6R_7$—$(C_1$-$C_5)$alkyl group, a —$CONR_6R_7$ group or a $CONR_6R_7$—$(C_1$-$C_5)$alkyl group, $R_4$ represents:
a $(C_1$-$C_5)$alkyl group;
a $(C_3$-$C_6)$cycloalkyl group;
a mono- or bicyclic aryl group having from 5 to 10 carbon atoms;
a mono- or bicyclic heteroaryl group having from 2 to 9 carbon atoms;
when $R_4$ is an aryl or heteroaryl group, it can optionally be substituted by 1 to 4 substituents chosen from halogen atoms, $(C_1$-$C_5)$alkyl, $(C_1$-$C_5)$alkoxy, $(C_1$-$C_5)$haloalkyl, hydroxyl, hydroxy$(C_1$-$C_5)$alkyl, $(C_1$-$C_5)$alkoxy$(C_1$-$C_5)$alkyl, cyano, optionally substituted phenyl, optionally substituted benzyl, —$COOR_5$ or —$NR_6R_7$ groups, a —$COOR_5$—$(C_1$-$C_5)$alkyl group, an —$NR_6R_7$—$(C_1$-$C_5)$alkyl, group, a —$CONR_6R_7$ group or an —$SO_2NR_6R_7$ group, where $R_{3a,b}$ and $R_4$ are either carried by different carbon atoms or are carried by the same carbon atom and, when they are carried by the same carbon atom, can together form a ring in the spiro position, in particular a ring of formula a), b), c) or d):

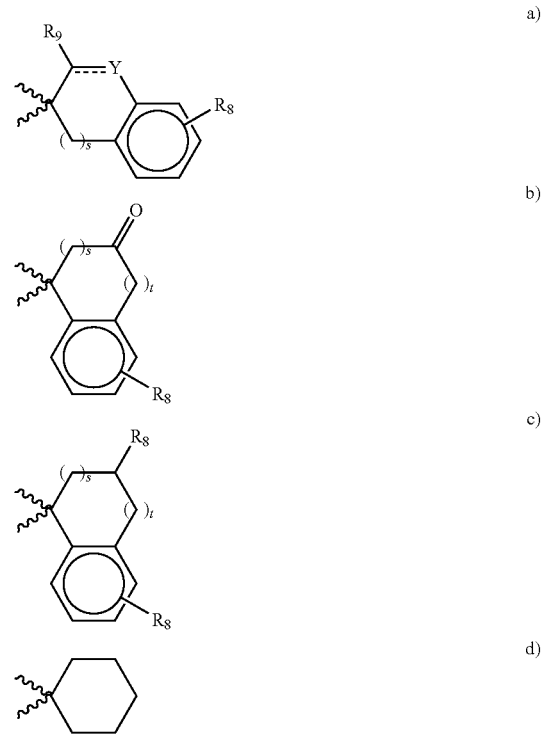

in which:
the dotted bond is a single bond or a double bond;
s is an integer equal to 0, 1, 2 or 3;
t is an integer equal to 0, 1, 2 or 3, it not being possible for s and t to be equal at the same time to 0;
$R_8$ represents a hydrogen or halogen atom, a $(C_1$-$C_5)$alkyl, $(C_1$-$C_5)$alkoxy, trifluoromethyl, hydroxyl, hydroxymethyl or cyano group, a —$COOR_5$ group or an —$NR_6R_7$ group;
$R_9$ represents a hydrogen atom or a $(C_1$-$C_5)$alkyl or hydroxyl group;
Y represents a bond or a carbon or nitrogen atom;
n is an integer equal to 0 or 1;
o, p, q and r, which are identical or different, are integers equal to 0, 1 or 2;
i and j are integers equal to 0, 1, 2, 3 or 4;
$R_5$ represents a hydrogen atom, a $(C_1$-$C_5)$alkyl group or a $(C_3$-$C_6)$cycloalkyl group;
$R_6$ and $R_7$, which are identical or different, each represent a hydrogen atom, a $(C_1$-$C_5)$alkyl group, a $(C_3$-$C_6)$cycloalkyl, $(C_1$-$C_5)$alkylcarbonyl, hydroxymethyl$(C_1$-$C_5)$alkyl or $(C_1$-$C_5)$alkoxymethyl$(C_1$-$C_5)$alkyl group, an aryl group or an —$SO_2R_5$ group or can form, together with the nitrogen atom to which they are attached, a heterocycloalkyl, it being understood that, when X=$CH_2$, n=0, $R_{1a,b,c,d}$=H, $R_{2a,b,c,d}$=H and $R_{3a,b}$=H, then the $R_4$ group has to be other than phenyl optionally substituted by a halogen atom or a $(C_1$-$C_5)$alkyl, trifluoromethyl or $(C_1$-$C_5)$alkoxy group.

Mention may be made, among the compounds of formula (I) according to the invention, of the compounds for which:

X represents a carbon, oxygen, sulfur or nitrogen atom;

$R_{1a,b,c,d}$ and $R_{2a,b,c,d}$, which are identical or different, each represent a hydrogen or halogen atom, a $(C_1\text{-}C_5)$alkyl, $(C_1\text{-}C_5)$alkoxy, $(C_1\text{-}C_5)$haloalkyl or hydroxyl group, a —$COOR_5$ group, a —$CONR_6R_7$ group, an —$SO_2NR_6R_7$ group, a —$COR_5$ group or an aryl or heteroaryl, aryl$(C_1\text{-}C_5)$alkyl, heteroaryl$(C_1\text{-}C_5)$alkyl or heterocycloalkyl$(C_1\text{-}C_5)$alkyl group, it being possible for all the aryl or heteroaryl groups optionally to be substituted by 1 to 3 substituents chosen from cyano, $COOR_5$, $CONR_6R_7$, $SO_2R_5$, $(C_1\text{-}C_5)$alkoxy or $OCH_2CONR_6R_7$ groups, a halogen atom, $(C_1\text{-}C_5)$haloalkyl and only one aryl$(C_1\text{-}C_5)$alkyl group can optionally be substituted by a heteroaryl group, or $(R_{2a})$ or $(R_{2b})$ can also form, with the carbon atom to which they are attached, a C=O, C=CF$_2$ group, or $(R_{2a})$ and/or $(R_{2b})$ can also form, with the atom or atoms to which they are attached, a $(C_3\text{-}C_6)$cycloalkyl group, it being possible for these rings to be spiro when they are carried by the same carbon atom and to be optionally substituted by one to three halogen atoms, the $R_{3a,b}$ groups each represent a hydrogen atom, hydroxyl or cyano;

$R_4$ represents:

a $(C_1\text{-}C_5)$alkyl group;

a $(C_3\text{-}C_6)$cycloalkyl group;

a heterocycloalkyl group;

a monocyclic aryl group having from 5 to 6 carbon atoms;

a monocyclic heteroaryl group having from 2 to 5 carbon atoms;

when $R_4$ is an aryl or heteroaryl or heterocycloalkyl group, it can optionally be substituted by 1 to 4 substituents chosen from halogen atoms, $(C_1\text{-}C_5)$alkyl, $(C_1\text{-}C_5)$alkoxy, $(C_1\text{-}C_5)$haloalkyl, hydroxyl, cyano, optionally substituted phenyl, benzyl or —$COOR_5$ groups or a —$CONR_6R_7$ group;

where $R_{3a,b}$ and $R_4$ are either carried by different carbon atoms or are carried by the same carbon atom and, when they are carried by the same carbon atom, can together form a ring in the spiro position, in particular a ring of formula a), b), c) or d):

a)

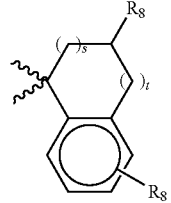

b)

c)

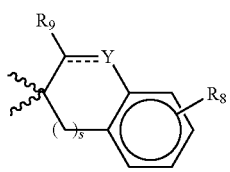

d)

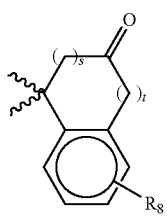

in which:
the dotted bond is a single bond or a double bond;
s is an integer equal to 0 or 1;
t is an integer equal to 0 or 1, it not being possible for s and t to be equal at the same time to 0;
$R_8$ represents a hydrogen atom or a hydroxyl group;
$R_9$ represents a hydrogen atom or a $(C_1\text{-}C_5)$alkyl group;
Y represents a bond or a carbon or nitrogen atom;
n is an integer equal to 0 or 1;
o, p, q and r, which are identical or different, are integers equal to 0 or 1;
i and j are integers equal to 0 or 1;
$R_5$ represents a hydrogen atom, a $(C_1\text{-}C_5)$alkyl group or a $(C_3\text{-}C_6)$cycloalkyl, halo$(C_1\text{-}C_5)$alkyl or optionally substituted phenyl group;
$R_6$ and $R_7$, which are identical or different, each represent a hydrogen atom, a $(C_1\text{-}C_5)$alkyl group, a $(C_3\text{-}C_6)$cycloalkyl group or an optionally substituted heterocycloalkyl group or can form, together with the nitrogen atom to which they are attached, an optionally substituted heterocycloalkyl;

it being understood that, when X=CH$_2$, n=0, $R_{1a,b,c,d}$=H, $R_{2a,b,c,d}$=H and $R_{3a,b}$=H, then the $R_4$ group has to be other than the phenyl group optionally substituted by a halogen atom or a $(C_1\text{-}C_5)$alkyl, trifluoromethyl or $(C_1\text{-}C_5)$alkoxy group.

Mention may be made, among the compounds of formula (I) according to the invention, of the compounds of formula (Ia) in which:

X represents either a carbon, oxygen, sulfur or nitrogen atom or the group

$R_{1a,b,c,d}$ and $R_{2a,b,c,d}$, which are identical or different, each represent a hydrogen or halogen atom, a $(C_1\text{-}C_5)$alkyl, $(C_1\text{-}C_5)$alkoxy, $(C_1\text{-}C_5)$haloalkyl, hydroxyl, hydroxy$(C_1\text{-}C_5)$alkyl or cyano group, a —$COOR_5$ group, an —$NR_6R_7$ group, a $COOR_5$—$(C_1\text{-}C_5)$alkyl group, an $NR_6R_7$—$(C_1\text{-}C_5)$alkyl group, a —$CONR_6R_7$ group, a $CONR_6R_7$—$(C_1\text{-}C_5)$alkyl group, an —$SO_2NR_6R_7$ group, a —$COR_5$ group or an aryl or heteroaryl, aryl$(C_1\text{-}C_5)$alkyl, heteroaryl$(C_1\text{-}C_5)$alkyl or heterocycloalkyl$(C_1\text{-}C_5)$alkyl group, it being possible for all the aryl or heteroaryl groups optionally to be substituted by 1 to 3 substituents chosen from cyano, $COOR_5$, $CONR_6R_7$, $SO_2R_5$, $(C_1\text{-}C_5)$alkoxy or $OCH_2CONR_6R_7$ groups, a halogen atom, $(C_1\text{-}C_5)$haloalkyl and only one aryl$(C_1\text{-}C_5)$alkyl group can optionally be substituted by a heteroaryl group, or ($R_{2a}$) or ($R_{2b}$) can also form, with the carbon atom to which they are attached, a C=O, C=CF$_2$ group, or ($R_{2a}$) and/or ($R_{2b}$) can also form, with the atom or atoms to which they are attached, a ($C_3$-$C_6$)cycloalkyl group, it being possible for these rings to be spiro when they are carried by the same carbon atom and to be optionally substituted by one to three halogen atoms, or ($R_{1d}$) and ($R_{2a}$) can also form, with the atoms to which they are attached, a ($C_3$-$C_7$)cycloalkyl group;

the $R_{3a,b}$ groups each represent a hydrogen atom, a fluorine atom or a ($C_1$-$C_5$)alkyl, ($C_1$-$C_5$)alkoxy, alkoxy($C_1$-$C_5$)alkyl, hydroxyl, hydroxy($C_1$-$C_5$)alkyl, ($C_1$-$C_5$)haloalkyl or cyano group, a —COOR$_5$ group, an —NR$_6$R$_7$ group, a COOR$_5$—($C_1$-$C_5$)alkyl group, an NR$_6$R$_7$—($C_1$-$C_5$)alkyl group, a —CONR$_6$R$_7$ group or a CONR$_6$R$_7$—($C_1$-$C_5$)alkyl group, R$_4$ represents:
  a ($C_1$-$C_5$)alkyl group;
  a ($C_3$-$C_6$)cycloalkyl group;
  a heterocycloalkyl group,
  a mono- or bicyclic aryl group having from 5 to 10 carbon atoms;
  a mono- or bicyclic heteroaryl group having from 2 to 9 carbon atoms;

when R$_4$ is an aryl or heteroaryl or heterocycloalkyl group, it can optionally be substituted by 1 to 4 substituents chosen from halogen atoms, ($C_1$-$C_5$)alkyl, ($C_1$-$C_5$)alkoxy, ($C_1$-$C_5$)haloalkyl, hydroxyl, hydroxy($C_1$-$C_5$)alkyl, ($C_1$-$C_5$)alkoxy($C_1$-$C_5$)alkyl, cyano, optionally substituted phenyl, optionally substituted benzyl, —COOR$_5$ or —NR$_6$R$_7$ groups, a —COOR$_5$—($C_1$-$C_5$)alkyl group, an —NR$_6$R$_7$—($C_1$-$C_5$)alkyl group, a —CONR$_6$R$_7$ group or an —SO$_2$NR$_6$R$_7$ group, $R_{3a,b}$ and R$_4$ are carried by different carbon atoms;

n is an integer equal to 0 or 1;

o, p, q and r, which are identical or different, are integers equal to 0, 1 or 2;

i and j are integers equal to 0, 1, 2, 3 or 4;

R$_5$ represents a hydrogen atom, a ($C_1$-$C_5$)alkyl group or a ($C_3$-$C_6$)cycloalkyl, halo($C_1$-$C_5$)alkyl or optionally substituted phenyl group;

R$_6$ and R$_7$, which are identical or different, each represent a hydrogen atom, a ($C_1$-$C_5$)alkyl group, a ($C_3$-$C_6$)cycloalkyl, ($C_1$-$C_5$)alkylcarbonyl, hydroxymethyl($C_1$-$C_5$)alkyl or ($C_1$-$C_5$)alkoxymethyl($C_1$-$C_5$)alkyl group, an aryl group, an optionally substituted heterocycloalkyl group (for SAR110239) or an —SO$_2$R$_5$ group or can form, together with the nitrogen atom to which they are attached, an optionally substituted heterocycloalkyl, it being understood that, when X=CH$_2$, n=0, $R_{1a,b,c,d}$=H, $R_{2a,b,c,d}$=H and $R_{3a,b}$=H, then the R$_4$ group has to be other than phenyl optionally substituted by a halogen atom or a ($C_1$-$C_5$)alkyl, trifluoromethyl or ($C_1$-$C_5$)alkoxy group.

Mention may be made, among the compounds of formula (I) according to the invention, of the compounds of formula (Ib) in which:

X represents either a carbon, oxygen, sulfur or nitrogen atom or the group

$R_{1a,b,c,d}$ and $R_{2a,b,c,d}$, which are identical or different, each represent a hydrogen or halogen atom, a ($C_1$-$C_5$)alkyl, ($C_1$-$C_5$)alkoxy, ($C_1$-$C_5$)haloalkyl, hydroxyl, hydroxy($C_1$-$C_5$)alkyl or cyano group, a —COOR$_5$ group, an —NR$_6$R$_7$ group, a COOR$_5$—($C_1$-$C_5$)alkyl group, an NR$_6$R$_7$—($C_1$-$C_5$)alkyl group, a —CONR$_6$R$_7$ group, a CONR$_6$R$_7$—($C_1$-$C_5$)alkyl group, an —SO$_2$NR$_6$R$_7$ group, a —COR$_5$ group or an aryl or heteroaryl, aryl($C_1$-$C_5$)alkyl, heteroaryl($C_1$-$C_5$)alkyl or heterocycloalkyl ($C_1$-$C_5$)alkyl group, it being possible for all the aryl or heteroaryl groups optionally to be substituted by 1 to 3 substituents chosen from cyano, COOR$_5$, CONR$_6$R$_7$, SO$_2$R$_5$, ($C_1$-$C_5$)alkoxy or OCH$_2$CONR$_6$R$_7$ groups, a halogen atom, ($C_1$-$C_5$)haloalkyl and only one aryl($C_1$-$C_5$)alkyl group can optionally be substituted by a heteroaryl group, or ($R_{2a}$) or ($R_{2b}$) can also form, with the carbon atom to which they are attached, a C=O, C=CF$_2$ group, or ($R_{2a}$) and/or ($R_{2b}$) can also form, with the atom or atoms to which they are attached, a ($C_3$-$C_6$)cycloalkyl group, it being possible for these rings to be spiro when they are carried by the same carbon atom and to be optionally substituted by one to three halogen atoms, or ($R_{1d}$) and ($R_{2a}$) can also form, with the atoms to which they are attached, a ($C_3$-$C_7$)cycloalkyl group;

the $R_{3a,b}$ groups each represent a hydrogen atom, a fluorine atom or a ($C_1$-$C_5$)alkyl, ($C_1$-$C_5$)alkoxy, alkoxy($C_1$-$C_5$)alkyl, hydroxyl, hydroxy($C_1$-$C_5$)alkyl, ($C_1$-$C_5$)haloalkyl or cyano group, a —COOR$_5$ group, an —NR$_6$R$_7$ group, a COOR$_5$—($C_1$-$C_5$)alkyl group, an NR$_6$R$_7$—($C_1$-$C_5$)alkyl group, a —CONR$_6$R$_7$ group or a CONR$_6$R$_7$—($C_1$-$C_5$)alkyl group, R$_4$ represents:
  a ($C_1$-$C_5$)alkyl group;
  a ($C_3$-$C_6$)cycloalkyl group;
  a heterocycloalkyl group;
  a mono- or bicyclic aryl group having from 5 to 10 carbon atoms;
  a mono- or bicyclic heteroaryl group having from 2 to 9 carbon atoms;

when R$_4$ is an aryl or heteroaryl or heterocycloalkyl group, it can optionally be substituted by 1 to 4 substituents chosen from halogen atoms, ($C_1$-$C_5$)alkyl, ($C_1$-$C_5$)alkoxy, ($C_1$-$C_5$)haloalkyl, hydroxyl, hydroxy($C_1$-$C_5$)alkyl, ($C_1$-$C_5$)alkoxy($C_1$-$C_5$)alkyl, cyano, optionally substituted phenyl, optionally substituted benzyl, —COOR$_5$ or —NR$_6$R$_7$ groups, a —COOR$_5$—($C_1$-$C_5$)alkyl group, an —NR$_6$R$_7$—($C_1$-$C_5$)alkyl group, a —CONR$_6$R$_7$ group or an —SO$_2$NR$_6$R$_7$ group, $R_{3a,b}$ and R$_4$ are carried by the same carbon atom but do not form a spiro group;

n is an integer equal to 0 or 1;

o, p, q and r, which are identical or different, are integers equal to 0, 1 or 2;

i and j are integers equal to 0, 1, 2, 3 or 4;

R$_5$ represents a hydrogen atom, a ($C_1$-$C_5$)alkyl group or a ($C_3$-$C_6$)cycloalkyl, halo($C_1$-$C_5$)alkyl or optionally substituted phenyl group;

R$_6$ and R$_7$, which are identical or different, each represent a hydrogen atom, a ($C_1$-$C_5$)alkyl group, a ($C_3$-$C_6$)cycloalkyl, ($C_1$-$C_5$)alkylcarbonyl, hydroxymethyl($C_1$-$C_5$)alkyl or ($C_1$-$C_5$)alkoxymethyl($C_1$-$C_5$)alkyl group, an aryl group, an optionally substituted heterocycloalkyl group or an —SO$_2$R$_5$ group or can form, together with the nitrogen atom to which they are attached, a heterocycloalkyl, it being understood that, when X=CH$_2$, n=0, $R_{1a,b,c,d}$=H, $R_{2a,b,c,d}$=H and $R_{3a,b}$=H, then the R$_4$ group has to be other than a phenyl group optionally substituted by a halogen atom or a $(C_1-C_5)$alkyl, trifluoromethyl or $(C_1-C_5)$alkoxy group.

Mention may be made, among the compounds of formula (I), (Ia) or (Ib) according to the invention, of the compounds in which:

X represents a carbon, oxygen, sulfur or nitrogen atom;

$R_{1a,b,c,d}$ and $R_{2a,b,c,d}$, which are identical or different, each represent a hydrogen or halogen atom, a $(C_1-C_5)$alkyl, $(C_1-C_5)$alkoxy, $(C_1-C_5)$haloalkyl, hydroxyl or hydroxy $(C_1-C_5)$alkyl group, a —$COOR_5$ group, a —$CONR_6R_7$ group, an —$SO_2NR_6R_7$ group, a —$COR_5$ group or an aryl or heteroaryl, aryl$(C_1-C_5)$alkyl, heteroaryl$(C_1-C_5)$alkyl or heterocycloalkyl$(C_1-C_5)$alkyl group, it being possible for all the aryl or heteroaryl groups optionally to be substituted by 1 to 3 substituents chosen from cyano, $COOR_5$, $CONR_6R_7$, $SO_2R_5$, $(C_1-C_5)$alkoxy or $OCH_2CONR_6R_7$ groups, a halogen atom, $(C_1-C_5)$haloalkyl and only one aryl$(C_1-C_5)$alkyl group can optionally be substituted by a heteroaryl group, or $(R_{2a})$ or $(R_{2b})$ can also form, with the carbon atom to which they are attached, a C=O, C=CF$_2$ group, or $(R_{2a})$ and/or $(R_{2b})$ can also form, with the atom or atoms to which they are attached, a $(C_3-C_6)$cycloalkyl group, it being possible for these rings to be spiro when they are carried by the same carbon atom and to be optionally substituted by one to three halogen atoms, the $R_{3a,b}$ groups each represent a hydrogen atom, $R_4$ represents:
a $(C_1-C_5)$alkyl group;
a $(C_3-C_6)$cycloalkyl group;
a heterocycloalkyl group;
a monocyclic aryl group having from 5 to 6 carbon atoms;
a monocyclic heteroaryl group having from 2 to 5 carbon atoms;
when $R_4$ is an aryl or heteroaryl or heterocycloalkyl group, it can optionally be substituted by 1 to 2 substituents chosen from halogen atoms, $(C_1-C_5)$alkyl, $(C_1-C_5)$alkoxy, $(C_1-C_5)$haloalkyl, hydroxyl, cyano, optionally substituted phenyl, or benzyl groups or a —$CONR_6R_7$ group, n is an integer equal to 0 or 1;
o, p, q and r, which are identical or different, are integers equal to 0 or 1;
i and j are integers equal to 0 or 1;
$R_5$ represents a hydrogen atom or a $(C_1-C_5)$alkyl or optionally substituted phenyl group;
$R_6$ and $R_7$, which are identical or different, each represent a hydrogen atom, a $(C_1-C_5)$alkyl group, a $(C_3-C_6)$cycloalkyl group or a heterocycloalkyl group or can form, together with the nitrogen atom to which they are attached, an optionally substituted heterocycloalkyl, it being understood that, when X=CH$_2$, n=0, $R_{1a,b,c,d}$=H, $R_{2a,b,c,d}$=H and $R_{3a,b}$=H, then the $R_4$ group has to be other than phenyl optionally substituted by a halogen atom or a $(C_1-C_5)$alkyl, trifluoromethyl or $(C_1-C_5)$alkoxy group.

Mention may be made, among the compounds of formula (Ib) according to the invention, of the compounds in which:

X represents a carbon, oxygen, sulfur or nitrogen atom;

$R_{1a,b,c,d}$ and $R_{2a,b,c,d}$, which are identical or different, each represent a hydrogen or halogen atom, a $(C_1-C_5)$alkyl, $(C_1-C_5)$alkoxy, $(C_1-C_5)$haloalkyl, hydroxyl or hydroxy $(C_1-C_5)$alkyl group, a —$COOR_5$ group, a —$CONR_6R_7$ group, an —$SO_2NR_6R_7$ group, a —$COR_5$ group or an aryl or heteroaryl, aryl$(C_1-C_5)$alkyl, heteroaryl$(C_1-C_5)$alkyl or heterocycloalkyl$(C_1-C_5)$alkyl group, it being possible for all the aryl or heteroaryl groups optionally to be substituted by 1 to 3 substituents chosen from cyano, $COOR_5$, $CONR_6R_7$, $SO_2R_5$, $(C_1-C_5)$alkoxy or $OCH_2CONR_6R_7$ groups, a halogen atom, $(C_1-C_5)$haloalkyl and only one aryl$(C_1-C_5)$alkyl group can optionally be substituted by a heteroaryl group, or $(R_{2a})$ or $(R_{2b})$ can also form, with the carbon atom to which they are attached, a C=O, C=CF$_2$ group, or $(R_{2a})$ and/or $(R_{2b})$ can also form, with the atom or atoms to which they are attached, a $(C_3-C_6)$cycloalkyl group, it being possible for these rings to be spiro when they are carried by the same carbon atom and to be optionally substituted by one to three halogen atoms, the $R_{3a,b}$ groups each represent a hydrogen atom or a hydroxyl group, $R_4$ represents:
a $(C_1-C_5)$alkyl group;
a $(C_3-C_6)$cycloalkyl group;
a heterocycloalkyl group;
a monocyclic aryl group having from 5 to 6 carbon atoms;
a monocyclic heteroaryl group having from 2 to 5 carbon atoms;
when $R_4$ is an aryl or heteroaryl or heterocycloalkyl group, it can optionally be substituted by 1 to 2 substituents chosen from halogen atoms, $(C_1-C_5)$alkyl, $(C_1-C_5)$alkoxy, $(C_1-C_5)$haloalkyl, hydroxyl, cyano, optionally substituted phenyl, or benzyl groups or a —$CONR_6R_7$ group, n is an integer equal to 0 or 1;
o, p, q and r, which are identical or different, are integers equal to 0 or 1;
i and j are integers equal to 0 or 1;
$R_5$ represents a hydrogen atom or a $(C_1-C_5)$alkyl or optionally substituted phenyl group;
$R_6$ and $R_7$, which are identical or different, each represent a hydrogen atom, a $(C_1-C_5)$alkyl group, a $(C_3-C_6)$cycloalkyl group or a heterocycloalkyl group or can form, together with the nitrogen atom to which they are attached, an optionally substituted heterocycloalkyl, it being understood that, when X=CH$_2$, n=0, $R_{1a,b,c,d}$=H, $R_{2a,b,c,d}$=H and $R_{3a,b}$=H, then the $R_4$ group has to be other than phenyl optionally substituted by a halogen atom or a $(C_1-C_5)$alkyl, trifluoromethyl or $(C_1-C_5)$alkoxy group.

Mention may be made, among the compounds of formula (I), (Ia) or (Ib) according to the invention, of a subgroup of compounds in which X is carbon, oxygen or nitrogen, $R_{1a,b,c,d}$, $R_{2a,b,c,d}$, $R_{3a,b}$ to $R_9$, Y, i, j, n, o, p, q, r, s and t being as defined above.

Among the latter compounds, compounds of the invention are compounds of formula (I), (Ia) or (Ib) in which:
p and r represent 1;
o and q represent 0;
i and j represent 1 or 2;
n represents 0 or 1;
$R_{1a,b,c,d}$ represent hydrogen or one of the $R_{1a,b,c,d}$ groups is a halogen and the others are hydrogen;
$R_{2a,b}$ represent hydrogen or one of the $R_{2a,b}$ groups is a $(C_1-C_5)$alkyl group, preferably methyl, and the other $R_{2a,b}$ group is hydrogen;
$R_{3a,b}$ represent hydrogen;
$R_4$ in the 4-position is chosen from the following heteroaryls:
pyridine
pyrazine
pyrazole
oxadiazole thiazole
imidazole.

Another group of compounds within the meaning of the invention corresponds to the derivatives of formula (I), (Ia) or (Ib) in which X represents the carbon or oxygen atom, n represents 1 and $R_4$ in the 4-position is an imidazole, a pyrazole or a pyridine, $R_{1a,b,c,d}$, $R_{2a,b,c,d}$, $R_{3a,b}$, $R_5$ to $R_7$, i, j, o, p, q and r being as defined above.

Another group of compounds within the meaning of the invention corresponds to the derivatives of formula (I), (Ia) or (Ib) in which X represents the carbon or oxygen atom, n represents 0 and $R_4$ in the 4-position is an imidazole, a pyrazole or a pyridine, $R_{1a,b,c,d}$, $R_{2a,b,c,d}$, $R_{3a,b}$, $R_5$ to $R_7$, i, j, o, p, q and r being as defined above.

Another group of compounds within the meaning of the invention corresponds to the derivatives of formula (I), (Ia) or (Ib) in which X represents the nitrogen atom, n represents 0 and $R_4$ in the 4-position is a pyrazole or a pyridine, $R_{1a,b,c,d}$, $R_{2a,b,c,d}$, $R_{3a,b}$, $R_5$ to $R_7$, i, j, o, p, q and r being as defined above.

Another group of compounds within the meaning of the invention corresponds to the derivatives of formula (I), (Ia) or (Ib) in which X represents the carbon atom or the oxygen atom, n represents 0, p represents 1, r represents 1, the two $R_{2a}$ and $R_{2b}$ groups carried by the same carbon atom forming a spiro group and $R_4$ in the 4-position is a pyrazole or a pyridine, $R_{1a,b,c,d}$, $R_{2c,d}$, $R_{3a,b}$, $R_5$ to $R_7$, i, j, o and q being as defined above.

Another group of compounds according to the invention corresponds to the compounds of formula (I) or (Ib) in which X represents the carbon, oxygen or nitrogen atom, n represents 0 or 1, i represents 1, $R_{3a}$ and $R_4$ are attached to the same carbon atom in the 4-position and $R_{3a}$ is a cyano or ($C_1$-$C_5$) alkoxy group, $R_{1a,b,c,d}$, $R_{2a,b,c,d}$, $R_{3b}$, $R_5$ to $R_7$, j, o, p, q and r being as defined above.

Another group of compounds of the invention is composed of the compounds of formula (I) in which:
X is a carbon, oxygen or nitrogen atom,
$R_{1a,b,c,d}$ and $R_{2a,b,c,d}$ are hydrogen;
i represents 1;
$R_{3a}$ and $R_4$, together with the carbon atom to which they are attached, form one of the optionally substituted groups below in the spiro position:

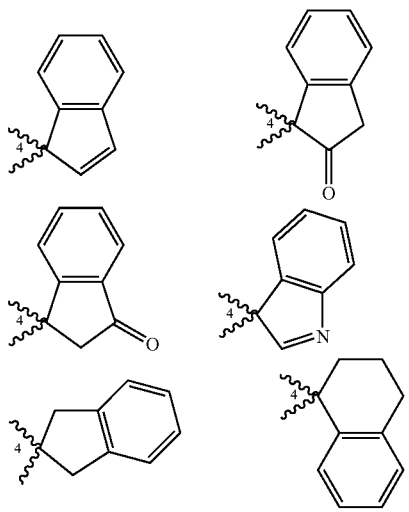

$R_{3b}$, $R_5$ to $R_7$, j, n, o, p, q and r being defined as in the formula (I) above.

Another group of compounds of the invention is composed of the compounds of formula (I) in which:
X is carbon;
$R_{1a,b,c,d}$ and $R_{2a,b,c,d}$ are hydrogen;
i represents 1;
$R_{3a}$ and $R_4$, together with the carbon atom to which they are attached, form one of the optionally substituted groups below in the spiro position:

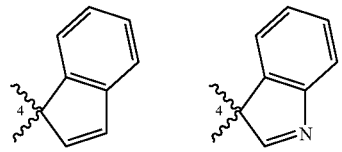

$R_{3b}$, $R_5$ to $R_7$, j, n, o, p, q and r being defined as in the formula (I) above.

Another group of compounds of the invention is composed of the compounds of formula (I) or (Ic) in which:
X is oxygen;
$R_{1a,b,c,d}$ and $R_{2a,b,c,d}$ are hydrogen;
i represents 1;
$R_{3a}$ and $R_4$, together with the carbon atom to which they are attached, form:

$R_{3b}$, $R_5$ to $R_7$, j, n, o, p, q and r being defined as in the formula (I) above.

Another group of compounds within the meaning of the invention corresponds to the derivatives of formula (I), (Ia) or (Ib) in which X represents the nitrogen atom, n represents 0, p represents 1, r, q and o represent 0, $R_{2a}$ carried by X is an aryl group optionally substituted by a $CONR_6R_7$ group or an $OCH_2CONR_6R_7$ group, $R_4$ in the 4-position is a pyrazole or a pyridine, $R_{1a,b,c,d}$, $R_{2b,c,d}$, $R_{3a,b}$, $R_5$ to $R_7$, i and j being as defined above.

Mention may be made, among the compounds of formula (I), (Ia) or (Ib) according to the invention, of:
(3,4-Dihydro-2H-quinolin-1-yl)[4-(1H-imidazol-4-yl)piperidin-1-yl]methanone
[4-(1H-Imidazol-4-yl)piperidin-1-yl](3-methyl-2,3-dihydrobenzo[1,4]oxazin-4-yl)methanone
(6-Chloro-2,3-dihydrobenzo[1,4]oxazin-4-yl)[4-(1H-imidazol-4-yl)piperidin-1-yl]methanone
(3,4-Dihydro-2H-quinolin-1-yl)(3,4,5,6-tetrahydro-2H-[4,4']bipyridinyl-1-yl)methanone
(3,4-Dihydro-2H-quinolin-1-yl)(3',4',5',6'-tetrahydro-2'H-[3,4']bipyridinyl-1'-yl)methanone
[4-(1-Benzyl-1H-imidazol-4-yl)piperidin-1-yl](3,4-dihydro-2H-quinolin-1-yl)methanone
(2-Methyl-3,4-dihydro-2H-quinolin-1-yl)[4-(1-methyl-1H-imidazol-4-yl)piperidin-1-yl]methanone
(2-Methyl-3,4-dihydro-2H-quinolin-1-yl)(4-phenylpiperidin-1-yl)methanone
[4-(1H-Imidazol-4-yl)piperidin-1-yl](2-methyl-3,4-dihydro-2H-quinolin-1-yl)methanone
1-(2-Methyl-3,4-dihydro-2H-quinoline-1-carbonyl)-4-phenylpiperidine-4-carbonitrile (3,4-Dihydro-2H-quinolin-1-yl)[4-(2-methoxyphenyl)piperidin-1-yl]methanone
(2-Methyl-3,4-dihydro-2H-quinolin-1-yl)(3,4,5,6-tetrahydro-2H-[4,4']bipyridinyl-1-yl)methanone
(3,4-Dihydro-2H-quinolin-1-yl)[4-(1H-pyrazol-4-yl)piperidin-1-yl]methanone
(3,4-Dihydro-2H-quinolin-1-yl)(4-(pyrazin-2-yl)piperidin-1-yl)methanone
1'-(3,4-Dihydroquinolin-1(2H)-ylcarbonyl)spiro[indene-1,4'-piperidine]
1'-(3,4-Dihydroquinolin-1(2H)-ylcarbonyl)-1,3-dihydrospiro[indene-2,4'-piperidine]
1-(3,4-Dihydro-2H-quinoline-1-carbonyl)-4-phenylpiperidine-4-carbonitrile
1'-(3,4-Dihydroquinolin-1(2H)-ylcarbonyl)-3,4-dihydro-2H-spiro[naphthalene-1,4'-piperidine]
(3,4-Dihydro-2H-quinolin-1-yl)(3-(pyridin-3-yl)pyrrolidin-1-yl)methanone
(3,4-Dihydro-2H-quinolin-1-yl)(3-(pyridin-4-yl)pyrrolidin-1-yl)methanone
(6-Fluoro-2,3-dihydrobenzo[1,4]oxazin-4-yl)(3',4',5',6'-tetrahydro-2'H-[3,4']bipyridinyl-1'-yl)methanone
(3,4-Dihydro-2H-quinolin-1-yl)[4-(4-phenylthiazol-2-yl)piperidin-1-yl]methanone
(3,4-Dihydro-2H-quinolin-1-yl)(4-([1,2,4]oxadiazol-3-yl)piperidin-1-yl)methanone
(3,4-Dihydro-2H-quinolin-1-yl)(4-(thiazol-2-yl)piperidin-1-yl)methanone
{4-[3-(2,6-Dichlorophenyl)[1,2,4]oxadiazol-5-yl]piperidin-1-yl}(3,4-dihydro-2H-quinolin-1-yl)methanone
(2,3-Dihydrobenzo[1,4]oxazin-4-yl)(3-(pyridin-3-yl)pyrrolidin-1-yl)methanone
(3,4-Dihydro-2H-quinolin-1-yl)[3-(5-fluoropyridin-3-yl)pyrrolidin-1-yl]methanone
4-Cyclohexyl-1-(3,4-dihydro-2H-quinoline-1-carbonyl)piperidine-4-carbonitrile
1-(3,4-Dihydro-2H-quinoline-1-carbonyl)-4-methylpiperidine-4-carbonitrile
1-(3,4-Dihydro-2H-quinoline-1-carbonyl)-4-ethylpiperidine-4-carbonitrile
(3,4-Dihydro-2H-quinolin-1-yl)[3-(2H-pyrazol-3-yl)pyrrolidin-1-yl]methanone
(3,4-Dihydro-2H-quinolin-1-yl)[3-(2H-pyrazol-3-yl)pyrrolidin-1-yl]methanone
(7-Chloro-2,3-dihydrobenzo[1,4]oxazin-4-yl)[4-(2H-pyrazol-3-yl)piperidin-1-yl]methanone
1'-(3,4-Dihydroquinolin-1(2H)-ylcarbonyl)-2-methylspiro[indole-3,4'-piperidine]
1'-(3,4-Dihydroquinolin-1(2H)-ylcarbonyl)spiro[indene-1,4'-piperidin]-3(2H)-one
1'-(3,4-Dihydroquinolin-1(2H)-ylcarbonyl)spiro[indene-1,4'-piperidin]-2(3H)-one
(6-Fluoro-2,3-dihydrobenzo[1,4]oxazin-4-yl)(3',4',5',6'-tetrahydro-2'H-[3,4']bipyridinyl-1'-yl)methanone
(6-Fluoro-2,3-dihydrobenzo[1,4]oxazin-4-yl)(3-(pyridin-3-yl)pyrrolidin-1-yl)methanone
(7-Chloro-2,3-dihydrobenzo[1,4]oxazin-4-yl)(3',4', 5',6'-tetrahydro-2'H-[3,4']bipyridinyl-1'-yl)methanone
(2,3-Dihydrobenzo[1,4]thiazin-4-yl)(3-(pyridin-3-yl)pyrrolidin-1-yl)methanone
(6-Methoxy-2,3-dihydrobenzo[1,4]oxazin-4-yl)(3-(pyridin-3-yl)pyrrolidin-1-yl)methanone
(7-Fluoro-2,3-dihydrobenzo[1,4]oxazin-4-yl)(3-(pyridin-3-yl)pyrrolidin-1-yl)methanone
(3,4-Dihydro-2H-quinolin-1-yl)[3-(1H-pyrazol-4-yl)pyrrolidin-1-yl]methanone
1'-(3,4-Dihydroquinolin-1(2H)-ylcarbonyl)-2,3-dihydrospiro[indene-1,4'-piperidin]-3-ol
(2,3-Dihydrobenzo[1,4]oxazin-4-yl)(6-hydroxy-3',4',5',6'-tetrahydro-2'H-[3,4']bipyridinyl-1'-yl)methanone
(2,3-Dihydrobenzo[1,4]oxazin-4-yl)[4-(1H-pyrazol-4-yl)piperidin-1-yl]methanone
(3,4-Dihydro-2H-quinolin-1-yl)[3-(6-fluoropyridin-3-yl)pyrrolidin-1-yl]methanone
(3,4-Dihydro-2H-quinolin-1-yl)[4-(2H-pyrazol-3-yl)piperidin-1-yl]methanone
(3,4-Dihydro-2H-quinolin-1-yl)[4-(1-methyl-1H-pyrazol-4-yl)piperidin-1-yl]methanone
(3,4-Dihydro-2H-quinolin-1-yl)(3,4,5,6-tetrahydro-2H-[3,3']bipyridinyl-1-yl)methanone
(3,4-Dihydro-2H-quinolin-1-yl)(3-(pyridin-2-yl)pyrrolidin-1-yl)methanone
(3,4-Dihydro-2H-quinolin-1-yl)(3-hydroxy-3-(pyridin-3-yl)pyrrolidin-1-yl)methanone
(3,4-Dihydro-2H-quinolin-1-yl)[3-(6-hydroxypyridin-3-yl)pyrrolidin-1-yl]methanone
1'-(3,4-Dihydroquinolin-1(2H)ylcarbonyl)-2,3-dihydrospiro[indene-1,4'-piperidin]-3-ol
(3,4-Dihydro-2H-quinolin-1-yl)[3-(6-methoxypyridin-3-yl)pyrrolidin-1-yl]methanone
(6-Chloro-2,3-dihydrobenzo[1,4]oxazin-4-yl)(3-(pyridin-3-yl)pyrrolidin-1-yl)methanone
(3,4-Dihydro-2H-quinoxalin-1-yl)(3-(pyridin-3-yl)pyrrolidin-1-yl)methanone
[3-(2-Chlorophenyl)pyrrolidin-1-yl](3,4-dihydro-2H-quinolin-1-yl)methanone
(3,4-Dihydro-2H-quinolin-1-yl)[3-(2-fluorophenyl)pyrrolidin-1-yl]methanone
(6-Methyl-3,4-dihydro-2H-quinolin-1-yl)(3-(pyridin-3-yl)pyrrolidin-1-yl)methanone
1'-(3,4-Dihydroquinolin-1(2H)-ylcarbonyl)-3,4-dihydro-2H-spiro[naphthalene-1,3'-pyrrolidine]
[3-(4-Chlorophenyl)pyrrolidin-1-yl](3,4-dihydro-2H-quinolin-1-yl)methanone
(4-Methyl-3,4-dihydro-2H-quinoxalin-1-yl)(3-(pyridin-3-yl)pyrrolidin-1-yl)methanone
(6,7-Difluoro-2,3-dihydrobenzo[1,4]oxazin-4-yl)(3-(pyridin-3-yl)pyrrolidin-1-yl)methanone
[3-(3-Chlorophenyl)pyrrolidin-1-yl](3,4-dihydro-2H-quinolin-1-yl)methanone
(3,4-Dihydro-2H-quinolin-1-yl)[3-(3-fluorophenyl)pyrrolidin-1-yl]methanone
(3-(Pyridin-3-yl)pyrrolidin-1-yl)(7-trifluoromethyl-3,4-dihydro-2H-quinolin-1-yl)methanone
(6-Bromo-3,4-dihydro-2H-quinolin-1-yl)(3-(pyridin-3-yl)pyrrolidin-1-yl)methanone
(2,3-Dihydrobenzo[1,4]thiazin-4-yl)(3',4',5',6'-tetrahydro-2'H-[3,4']bipyridinyl-1'-yl)methanone
(3,4-Dihydro-2H-quinolin-1-yl)[3-(5-methylpyridin-3-yl)pyrrolidin-1-yl]methanone
(6-Methoxy-3,4-dihydro-2H-quinolin-1-yl)(3-(pyridin-3-yl)pyrrolidin-1-yl)methanone
1-(3-(Pyridin-3-yl)pyrrolidine-1-carbonyl)-1,2,3,4-tetrahydroquinoline-6-carboxylic acid methyl ester
(3,4-Dihydro-2H-quinolin-1-yl)(2-(pyridin-4-yl)pyrrolidin-1-yl)methanone
1-(3-(Pyridin-3-yl)pyrrolidine-1-carbonyl)-2,3-dihydro-1H-quinolin-4-one
1-(3-(Pyridin-3-yl)pyrrolidine-1-carbonyl)-1,2,3,4-tetrahydroquinoline-6-sulfonic acid methylamide
4-(3-(Pyridin-3-yl)pyrrolidine-1-carbonyl)-3,4-dihydro-2H-benzo[1,4]oxazine-6-carboxylic acid methyl ester (8-Hydroxy-3,4-dihydro-2H-quinolin-1-yl)(3-(pyridin-3-yl)pyrrolidin-1-yl)methanone
(6-Chloro-2,3-dihydrobenzo[1,4]oxazin-4-yl)[3-(1H-pyrazol-4-yl)pyrrolidin-1-yl]methanone
1-(3-(Pyridin-3-yl)pyrrolidine-1-carbonyl)-1,2,3,4-tetrahydroquinoline-6-carboxylic acid
(2,3-Dihydrobenzo[1,4]oxazin-4-yl)[3-(1H-pyrazol-4-yl)pyrrolidin-1-yl]methanone
(6-Fluoro-2,3-dihydrobenzo[1,4]oxazin-4-yl)[3-(1H-pyrazol-4-yl)pyrrolidin-1-yl]methanone
(6-Hydroxymethyl-2,3-dihydrobenzo[1,4]oxazin-4-yl)(3-(pyridin-3-yl)pyrrolidin-1-yl)methanone
2-[1-(2,3-Dihydrobenzo[1,4]oxazine-4-carbonyl)pyrrolidin-3-yl]benzamide
(4-Amino-3,4-dihydro-2H-quinolin-1-yl)(3-(pyridin-3-yl)pyrrolidin-1-yl)methanone
(3,4-Dihydro-2H-quinolin-1-yl)(3-(pyrazin-2-yl)pyrrolidin-1-yl)methanone
[3-(5-Chloropyridin-3-yl)pyrrolidin-1-yl](3,4-dihydro-2H-quinolin-1-yl)methanone
(3,4-Dihydro-2H-quinolin-1-yl)((S)-3-(pyridin-4-yl)pyrrolidin-1-yl)methanone
(3,4-Dihydro-2H-quinolin-1-yl)((R)-3-(pyridin-4-yl)pyrrolidin-1-yl)methanone
(2,3-Dihydrobenzo[1,4]oxazin-4-yl)[3-(2-fluorophenyl)pyrrolidin-1-yl]methanone
[3-(2-Chlorophenyl)pyrrolidin-1-yl](2,3-dihydrobenzo[1,4]oxazin-4-yl)methanone
[3-(3-Chlorophenyl)pyrrolidin-1-yl](2,3-dihydrobenzo[1,4]oxazin-4-yl)methanone
1'-(2,3-Dihydro-4H-1,4-benzoxazin-4-ylcarbonyl)-3,4-dihydro-2H-spiro[naphthalene-1,3'-pyrrolidine]
[3-(4-Chlorophenyl)pyrrolidin-1-yl](2,3-dihydrobenzo[1,4]oxazin-4-yl)methanone
(2,3-Dihydrobenzo[1,4]oxazin-4-yl)[3-(4-methoxyphenyl)pyrrolidin-1-yl]methanone
(2,3-Dihydrobenzo[1,4]oxazin-4-yl)[3-(3-(trifluoromethyl)phenyl)pyrrolidin-1-yl]methanone
(2,3-Dihydrobenzo[1,4]oxazin-4-yl)[3-(2-methoxyphenyl)pyrrolidin-1-yl]methanone
(2,3-Dihydrobenzo[1,4]oxazin-4-yl)[3-(3-fluorophenyl)pyrrolidin-1-yl]methanone
(2,3-Dihydrobenzo[1,4]oxazin-4-yl)[3-(4-fluorophenyl)pyrrolidin-1-yl]methanone
1-(3-(Pyridin-3-yl)pyrrolidine-1-carbonyl)-1,2,3,4-tetrahydroquinoline-6-sulfonic acid dimethylamide
(4-Ethyl-3,4-dihydro-2H-quinoxalin-1-yl)(3-(pyridin-3-yl)pyrrolidin-1-yl)methanone
(4-Propyl-3,4-dihydro-2H-quinoxalin-1-yl)(3-(pyridin-3-yl)pyrrolidin-1-yl)methanone
3-[1-(2,3-Dihydrobenzo[1,4]oxazine-4-carbonyl)pyrrolidin-3-yl]pyridine-2-carbonitrile
(2,3-Dihydrobenzo[1,4]oxazin-4-yl)[3-(2-fluoropyridin-3-yl)pyrrolidin-1-yl]methanone
[3-(2,3-Difluorophenyl)pyrrolidin-1-yl](2,3-dihydrobenzo[1,4]oxazin-4-yl)methanone
(4,4-Dimethyl-3,4-dihydro-2H-quinolin-1-yl)(3-(pyridin-3-yl)pyrrolidin-1-yl)methanone
(4,4-Dimethyl-3,4-dihydro-2H-quinolin-1-yl)[3-(1H-pyrazol-4-yl)pyrrolidin-1-yl]methanone
1-(2,3-Dihydrobenzo[1,4]oxazine-4-carbonyl)-3-(pyridin-3-yl)pyrrolidine-3-carbonitrile
1-(2,3-Dihydrobenzo[1,4]oxazine-4-carbonyl)-3-(pyridin-3-yl)pyrrolidine-3-carbonitrile
1-(3,4-Dihydro-2H-quinoline-1-carbonyl)-3-(pyridin-3-yl)pyrrolidine-3-carbonitrile
4-(3-(Pyridin-3-yl)pyrrolidine-1-carbonyl)-3,4-dihydro-2H-quinoxaline-1-carboxylic acid dimethylamide
(2,3-Dihydrobenzo[1,4]oxazin-4-yl)[3-(1H-imidazol-4-yl)pyrrolidin-1-yl]methanone
(3,4-Dihydro-2H-quinolin-1-yl)[3-(1H-imidazol-4-yl)pyrrolidin-1-yl]methanone
[3-(2-Chloropyridin-3-yl)pyrrolidin-1-yl](2,3-dihydrobenzo[1,4]oxazin-4-yl)methanone
(2,3-Dihydrobenzo[1,4]oxazin-4-yl)[3-(2-methylpyridin-3-yl)pyrrolidin-1-yl]methanone
(2,3-Dihydrobenzo[1,4]oxazin-4-yl)(3-(pyrazin-2-yl)pyrrolidin-1-yl)methanone
[3-(2,3-Difluorophenyl)pyrrolidin-1-yl](2,3-dihydrobenzo[1,4]oxazin-4-yl)methanone
(4-Hydroxy-3,4-dihydro-2H-quinolin-1-yl)(3(pyridin-3-yl)pyrrolidin-1-yl)methanone
4-(3-(Pyridin-3-yl)pyrrolidine-1-carbonyl)-3,4-dihydro-2H-quinoxaline-1-carboxylic acid methyl ester
(4-Butyl-3,4-dihydro-2H-quinoxalin-1-yl)(3-(pyridin-3-yl)pyrrolidin-1-yl)methanone
1-[4-(3-(Pyridin-3-yl)pyrrolidine-1-carbonyl)-3,4-dihydro-2H-quinoxalin-1-yl]ethanone
(4-Benzyl-3,4-dihydro-2H-quinoxalin-1-yl)(3-(pyridin-3-yl)pyrrolidin-1-yl)methanone
(4-Methyl-3,4-dihydro-2H-quinoxalin-1-yl)[3-(1H-pyrazol-4-yl)pyrrolidin-1-yl]methanone
(4-Methyl-3,4-dihydro-2H-quinoxalin-1-yl)(3-(pyridin-3-yl)pyrrolidin-1-yl)methanone
(6-Chloro-2,3-dihydrobenzo[1,4]oxazin-4-yl)[3-(2-chlorophenyl)pyrrolidin-1-yl]methanone
(6-Chloro-2,3-dihydrobenzo[1,4]oxazin-4-yl)[3-(3-chlorophenyl)pyrrolidin-1-yl]methanone
(6-Chloro-2,3-dihydrobenzo[1,4]oxazin-4-yl)[3-(2-fluorophenyl)pyrrolidin-1-yl]methanone
(6-Chloro-2,3-dihydrobenzo[1,4]oxazin-4-yl)[3-(3-fluorophenyl)pyrrolidin-1-yl]methanone
(6-Chloro-2,3-dihydrobenzo[1,4]oxazin-4-yl)[3-(2-(trifluoromethyl)phenyl)pyrrolidin-1-yl]methanone
1'-[(6-Chloro-2,3-dihydro-4H-1,4-benzoxazin-4-yl)carbonyl]-3,4-dihydro-2H-spiro[naphthalene-1,3'-pyrrolidine]
(7-Chloro-4,4-dimethyl-3,4-dihydro-2H-quinolin-1-yl)[3-(1H-pyrazol-4-yl)pyrrolidin-1-yl]methanone
(6,7-Difluoro-4,4-dimethyl-3,4-dihydro-2H-quinolin-1-yl)[3-(1H-pyrazol-4-yl)pyrrolidin-1-yl]methanone
(6,7-Difluoro-4,4-dimethyl-3,4-dihydro-2H-quinolin-1-yl)(3-(pyridin-3-yl)pyrrolidin-1-yl)methanone
4-{4-[3-(1H-Pyrazol-4-yl)pyrrolidine-1-carbonyl]-3,4-dihydro-2H-quinoxalin-1-yl}benzonitrile
(6-Methoxy-4,4-dimethyl-3,4-dihydro-2H-quinolin-1-yl)[3-(1H-pyrazol-4-yl)pyrrolidin-1-yl]methanone
1-(3-Fluorobenzyl)-5-trifluoromethyl-1H-pyrrolo[2,3-b]pyridine-2-carboxylic acid (6-(methylamino)pyridin-3-yl)amide
[3-(2-Chlorophenyl)pyrrolidin-1-yl](4,4-dimethyl-3,4-dihydro-2H-quinolin-1-yl)methanone
2-[1-(2,3-Dihydrobenzo[1,4]oxazine-4-carbonyl)pyrrolidin-3-yl]benzoic acid methyl ester
(3,4-Dihydro-2H-quinolin-1-yl)(3-methoxy-3-(pyridin-3-yl)pyrrolidin-1-yl)methanone
(2,3-Dihydrobenzo[1,4]oxazin-4-yl)[3-(2-methoxypyridin-3-yl)pyrrolidin-1-yl]methanone
4-{4-[3-(1H-Pyrazol-4-yl)pyrrolidine-1-carbonyl]-3,4-dihydro-2H-quinoxalin-1-ylmethyl}benzonitrile
1'-{[3-(1H-Pyrazol-4-yl)pyrrolidin-1-yl]carbonyl}-2',3'-dihydro-1'H-spiro[cyclopentane-1,4'-quinoline]
(6-Chloro-4,4-dimethyl-3,4-dihydro-2H-quinolin-1-yl)[3-(1H-pyrazol-4-yl)pyrrolidin-1-yl]methanone

[3-(1H-Pyrazol-4-yl)pyrrolidin-1-yl](6-trifluoromethyl-2,3-dihydrobenzo[1,4]oxazin-4-yl)methanone
(6-Trifluoromethyl-2,3-dihydrobenzo[1,4]oxazin-4-yl)[3-(2-(trifluoromethyl)phenyl)pyrrolidin-1-yl]methanone
5-[1-(3,4-Dihydro-2H-quinoline-1-carbonyl)piperidin-4-yl]-2,4-dihydropyrazol-3-one
(4,4-Dimethyl-3,4-dihydro-2H-quinolin-1-yl)(3-(pyridazin-4-yl)pyrrolidin-1-yl)methanone
(5-Chloro-4,4-dimethyl-3,4-dihydro-2H-quinolin-1-yl)[3-(1H-pyrazol-4-yl)pyrrolidin-1-yl]methanone
(3,4-Dihydro-2H-quinoxalin-1-yl)[3-(1H-pyrazol-4-yl)pyrrolidin-1-yl]methanone
(2-Azaspiro[4.5]dec-2-yl)(2,3-dihydrobenzo[1,4]oxazin-4-yl)methanone
[4-(3-(Morpholin-4-yl)propyl)-3,4-dihydro-2H-quinoxalin-1-yl][3-(1H-pyrazol-4-yl)pyrrolidin-1-yl]methanone
(5-Hydroxy-3,4-dihydro-2H-quinolin-1-yl)[3-(1H-pyrazol-4-yl)pyrrolidin-1-yl]methanone
[4-(2-(Morpholin-4-yl)ethyl)-3,4-dihydro-2H-quinoxalin-1-yl][3-(1H-pyrazol-4-yl)pyrrolidin-1-yl]methanone
(4,4-Dimethyl-3,4-dihydro-2H-quinolin-1-yl)[3-(2-(trifluoromethyl)phenyl)pyrrolidin-1-yl]methanone
(3-Methyl-2,3-dihydrobenzo[1,4]oxazin-4-yl)[3-(1H-pyrazol-4-yl)pyrrolidin-1-yl]methanone
5-[1-(2,3-Dihydrobenzo[1,4]oxazine-4-carbonyl)pyrrolidin-3-yl]-2,4-dihydropyrazol-3-one
[3-(1H-Pyrazol-4-yl)pyrrolidin-1-yl][4-(2,2,2-trifluoroethyl)-3,4-dihydro-2H-quinoxalin-1-yl]methanone
4-{4-[3-(1H-Pyrazol-4-yl)pyrrolidine-1-carbonyl]-3,4-dihydro-2H-quinoxalin-1-yl}benzoic acid
N-Cyclopropyl-4-{4-[3-(1H-Pyrazol-4-yl)pyrrolidine-1-carbonyl]-3,4-dihydro-2H-quinoxalin-1-yl}benzamide
(2,3-Dihydrobenzo[1,4]oxazin-4-yl)[3-(4-fluoro-2-(trifluoromethyl)phenyl)pyrrolidin-1-yl]methanone
4-{4-[3-Hydroxy-3-(2H-pyrazol-3-yl)pyrrolidine-1-carbonyl]-3,4-dihydro-2H-quinoxalin-1-yl)methyl}benzonitrile
[4-(4-(Methanesulfonyl)benzyl)-3,4-dihydro-2H-quinoxalin-1-yl][3-(1H-pyrazol-4-yl)pyrrolidin-1-yl]methanone
3-{4-[3-(1H-Pyrazol-4-yl)pyrrolidine-1-carbonyl]-3,4-dihydro-2H-quinoxalin-1-ylmethyl}benzonitrile
(4-Difluoromethylene-3,4-dihydro-2H-quinolin-1-yl)(3-(pyridin-3-yl)pyrrolidin-1-yl)methanone
(4-Benzyl-3,4-dihydro-2H-quinoxalin-1-yl)[3-(1H-pyrazol-4-yl)pyrrolidin-1-yl]methanone
(2,3-Dihydrobenzo[1,4]oxazin-4-yl)[3-hydroxy-3-(2H-pyrazol-3-yl)pyrrolidin-1-yl]methanone
(3,4-Dihydro-2H-quinoxalin-1-yl)[3-(1H-pyrazol-4-yl)pyrrolidin-1-yl]methanone
(6,7-Difluoro-3,4-dihydro-2H-quinoxalin-1-yl)[3-(1H-pyrazol-4-yl)pyrrolidin-1-yl]methanone
6-{4-[3-(1H-Pyrazol-4-yl)pyrrolidine-1-carbonyl]-3,4-dihydro-2H-quinoxalin-1-ylmethyl}nicotinonitrile
1'-(3,4-Dihydroquinoxalin-1(2H)-ylcarbonyl)-3,4-dihydro-2H-spiro[naphthalene-1,3'-pyrrolidine]
4-[1-(2,3-Dihydrobenzo[1,4]oxazine-4-carbonyl)pyrrolidin-3-yl]-1H-pyrazole-3-carbonitrile
N-Cyclopropyl-3-{4-[3-(1H-pyrazol-4-yl)pyrrolidine-1-carbonyl]-3,4-dihydro-2H-quinoxalin-1-ylmethyl}benzamide
N-(Piperidin-1-yl)-4-{4-[3-(1H-pyrazol-4-yl)pyrrolidine-1-carbonyl]-3,4-dihydro-2H-quinoxalin-1-yl}benzamide
(4-{4-[3-(1H-Pyrazol-4-yl)pyrrolidine-1-carbonyl]-3,4-dihydro-2H-quinoxalin-1-yl}phenyl)(pyrrolidin-1-yl)methanone
(Morpholin-4-yl)(4-{4-[3-(1H-pyrazol-4-yl)pyrrolidine-1-carbonyl]-3,4-dihydro-2H-quinoxalin-1-yl}phenyl)methanone
(4-Methylpiperazin-1-yl)(4-{4-[3-(1H-pyrazol-4-yl)pyrrolidine-1-carbonyl]-3,4-dihydro-2H-quinoxalin-1-yl}phenyl)methanone
N-Cyclopropyl-2-(4-{4-[3-(1H-pyrazol-4-yl)pyrrolidine-1-carbonyl]-3,4-dihydro-2H-quinoxalin-1-yl}phenyl)acetamide
Trifluoromethanesulfonic acid 4-{4-[3-(1H-pyrazol-4-yl)pyrrolidine-1-carbonyl]-3,4-dihydro-2H-quinoxalin-1-yl}phenyl ester
N-Cyclopropyl-2-methoxy-4-{4-[3-(1H-pyrazol-4-yl)pyrrolidine-1-carbonyl]-3,4-dihydro-2H-quinoxalin-1-yl}benzamide
4-{4-[3-(1H-Pyrazol-4-yl)pyrrolidine-1-carbonyl]-3,4-dihydro-2H-quinoxalin-1-yl}-2-(trifluoromethyl)benzonitrile
N-Cyclopropyl-2-(4-{4-[3-(1H-pyrazol-4-yl)pyrrolidine-1-carbonyl]-3,4-dihydro-2H-quinoxalin-1-yl}phenoxy)acetamide
N-Cyclopropyl-2-(3-{4-[3-(1H-pyrazol-4-yl)pyrrolidine-1-carbonyl]-3,4-dihydro-2H-quinoxalin-1-yl}phenoxy)acetamide
[4-(5-Bromopyridin-2-yl)-3,4-dihydro-2H-quinoxalin-1-yl][3-(1H-pyrazol-4-yl)pyrrolidin-1-yl]methanone
2,2-Difluoro-1'-{[3-(1H-pyrazol-4-yl)pyrrolidin-1-yl]carbonyl}-2',3'-dihydro-1'H-spiro[cyclopropane-1,4'-quinoline]
1-[3-(1H-Pyrazol-4-yl)pyrrolidine-1-carbonyl]-1,2,3,4-tetrahydroquinoline-4-carboxylic acid methyl ester
[3-(1H-Pyrazol-4-yl)pyrrolidin-1-yl](8-trifluoromethyl-2,3-dihydrobenzo[1,4]oxazin-4-yl)methanone
3-{4-[3-(1H-Pyrazol-4-yl)pyrrolidine-1-carbonyl]-3,4-dihydro-2H-quinoxalin-1-yl}benzonitrile
4-{4-[3-(1H-Pyrazol-4-yl)pyrrolidine-1-carbonyl]-3,4-dihydro-2H-quinoxalin-1-yl}benzamide
5-{4-[3-(1H-Pyrazol-4-yl)pyrrolidine-1-carbonyl]-3,4-dihydro-2H-quinoxalin-1-yl}pyridine-2-carboxylic acid amide
4-{4-[3-(1H-Pyrazol-4-yl)pyrrolidine-1-carbonyl]-3,4-dihydro-2H-quinoxalin-1-ylmethyl}benzoic acid methyl ester
5-{4-[3-(1H-Pyrazol-4-yl)pyrrolidine-1-carbonyl]-3,4-dihydro-2H-quinoxalin-1-yl}nicotinonitrile
[3-(1H-Pyrazol-4-yl)pyrrolidin-1-yl](4-(pyridin-2-ylmethyl)-3,4-dihydro-2H-quinoxalin-1-yl)methanone
(2,3-Dihydrobenzo[1,4]oxazin-4-yl)[3-(2-(trifluoromethyl)pyridin-3-yl)pyrrolidin-1-yl]methanone
(2,3-Dihydrobenzo[1,4]oxazin-4-yl)[3-(2-(trifluoromethyl)piperidin-3-yl)pyrrolidin-1-yl]methanone
[3-(1H-Pyrazol-4-yl)pyrrolidin-1-yl][4-(5-(trifluoromethyl)pyridin-2-yl)-3,4-dihydro-2H-quinoxalin-1-yl]methanone
4-{4-[3-(2-(Trifluoromethyl)phenyl)pyrrolidine-1-carbonyl]-3,4-dihydro-2H-quinoxalin-1-yl}benzonitrile
[3-(1H-Pyrazol-4-yl)pyrrolidin-1-yl](4-(pyridin-3-ylmethyl)-3,4-dihydro-2H-quinoxalin-1-yl)methanone
[3-(1H-Pyrazol-4-yl)pyrrolidin-1-yl][4-(4-(trifluoromethyl)benzyl)-3,4-dihydro-2H-quinoxalin-1-yl]methanone
(8-Chloro-2,3-dihydrobenzo[1,4]oxazin-4-yl)[3-(1H-pyrazol-4-yl)pyrrolidin-1-yl]methanone
4-{4-[3-(1H-Pyrazol-4-yl)pyrrolidine-1-carbonyl]-3,4-dihydro-2H-quinoxalin-1-ylmethyl}benzoic acid
[3-(1H-Pyrazol-4-yl)pyrrolidin-1-yl][4-(4-([1,2,4]triazol-1-yl)benzyl)-3,4-dihydro-2H-quinoxalin-1-yl]methanone
(2,3-Dihydrobenzo[1,4]oxazin-4-yl)[3-(3-trifluoromethyl-1H-pyrazol-4-yl)pyrrolidin-1-yl]methanone 4-{4-[(S)-3-(1H-Pyrazol-4-yl)pyrrolidine-1-carbonyl]-3,4-dihydro-2H-quinoxalin-1-yl}benzonitrile 4-{4-[(R)-3-(1H-Pyrazol-4-yl)pyrrolidine-1-carbonyl]-3,4-dihydro-2H-quinoxalin-1-yl}benzonitrile 4-{4-[3-(1H-Pyrazol-4-yl)pyrrolidine-1-carbonyl]-3,4-dihydro-2H-quinoxalin-1-ylmethyl}benzamide 5-{4-[3-(1H-Pyrazol-4-yl)pyrrolidine-1-carbonyl]-3,4-dihydro-2H-quinoxalin-1-yl}nicotinic acid ethyl ester N-Cyclopropyl-4-{4-[3-(1H-pyrazol-4-yl)pyrrolidine-1-carbonyl]-3,4-dihydro-2H-quinoxalin-1-ylmethyl}benzamide N-(1,1-Dioxotetrahydro-1$\lambda^6$-thiophen-3-yl)-4-{4-[3-(1H-pyrazol-4-yl)pyrrolidine-1-carbonyl]-3,4-dihydro-2H-quinoxalin-1-yl}benzamide 4-{4-[3-(1H-Pyrazol-4-yl)pyrrolidine-1-carbonyl]-3,4-dihydro-2H-quinoxalin-1-yl}benzoic acid N'-phenylhydrazide The above compounds can optionally be substituted by one or more of the following groups: halogen atoms, $(C_1-C_5)$ alkyl, $(C_1-C_5)$alkoxy, $(C_1-C_5)$haloalkyl, hydroxyl, hydroxy $(C_1-C_5)$alkyl, $(C_1-C_5)$alkoxy$(C_1-C_5)$alkyl, cyano, optionally substituted phenyl, optionally substituted benzyl, —$COOR_5$ or —$NR_6R_7$ groups, a $COOR_5$—$(C_1-C_5)$alkyl group, an $NR_6R_7$—$(C_1-C_5)$alkyl group, a —$CONR_6R_7$ group, a $CONR_6R_7$—$(C_1-C_5)$alkyl group or an —$SO_2NR_6R_7$ group.

In that which follows, the term "protective group (Pg)" is understood to mean a group which makes it possible, first, to protect a reactive functional group, such as a hydroxyl or an amine, during a synthesis and, secondly, to regenerate the reactive functional group intact at the end of the synthesis. Examples of protective groups and also of methods of protection and deprotection are given in "Protective Groups in Organic Synthesis", Green et al., $3^{rd}$ Edition (John Wiley & Sons Inc., New York).

The term "leaving group (Lg)" is understood to mean, in what follows, a group which can be easily split from a molecule by cleavage of a heterolytic bond with departure of an electron pair. This group can thus be easily replaced by another group during a substitution reaction, for example. Such leaving groups are, for example, halogens or an activated hydroxyl group, such as a mesyl, tosyl, triflate, acetyl, para-nitrophenyl, and the like. Examples of leaving groups and of the methods for their preparation are given in "Advances in Organic Chemistry", J. March, $3^{rd}$ Edition, Wiley Interscience, pp. 310-316.

In accordance with the invention, the compounds of general formula (I) can be prepared according to the processes below. In the case where X represents a nitrogen atom, it has to be substituted either by an $R_{2a,b,c,d}$ group (other than H) or by a protective group Pg as defined above.

Scheme 1 (Method 1):

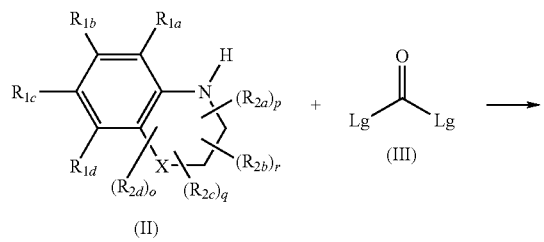

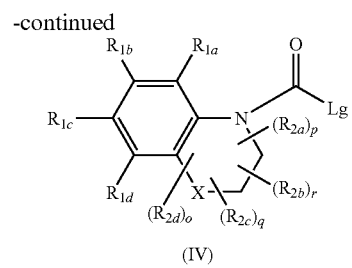

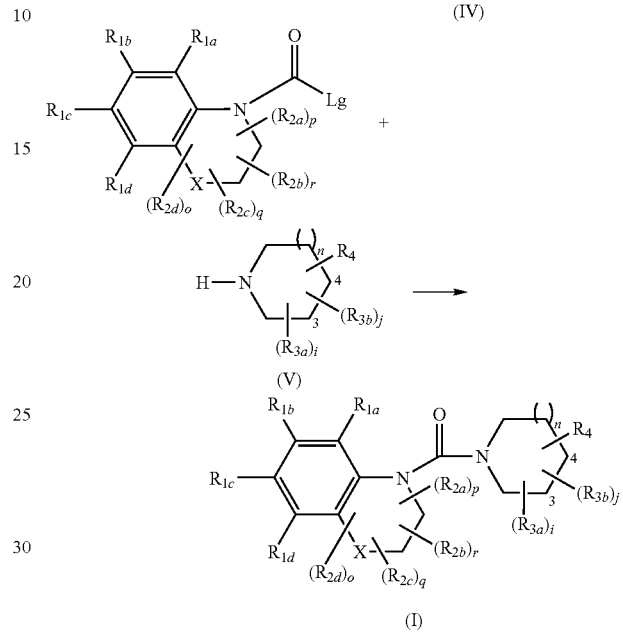

In Scheme 1, the compounds of formula (IV) can be prepared by reaction between the intermediates of formula (II) and a carbonyl of formula (III) exhibiting two leaving groups Lg (for example, a chlorine atom, a trichloromethoxy group, a para-nitrophenyl group, an imidazole group or a methylimidazolium group) in the presence of a base, such as triethylamine or diisopropylamine, in a solvent, such as dichloromethane or tetrahydrofuran, at a temperature varying from ambient temperature to 80° C. The compounds of formula (I) are obtained by coupling between activated derivatives (IV) and amines (V) in the presence or absence of a base, such as triethylamine or potassium carbonate, in a solvent, such as tetrahydrofuran, dichloromethane, acetonitrile or water, at a temperature varying from ambient temperature to 100° C.

The heterocycles of general formula (II) are available commercially or can be prepared by methods described in the literature ("Comprehensive Heterocyclic Chemistry", Katritzky et al., $2^{nd}$ Edition (Pergamon Press); Kuwabe, S., Torraca, K. E., Buchwald, S. L., JACS. (2001), 123(49), 12202-12206; Coudert, G., Guillaumet, G., Loubinoux, B., Synthesis, 7, 541-543; Hoffman, W. W., Kraska, A. R., Eur. Pat. Appl. (1985), EP 130 795 A2).

The heterocycles of general formula (V) are available commercially or can be prepared by methods described in the literature ("Comprehensive Heterocyclic Chemistry", Katritzky et al., $2^{nd}$ Edition (Pergamon Press); Buffat, Maxime G. P., Tetrahedron (2004), 60(8), 1701-1729; Laschat, S., Dickner, T., Synthesis (2000), (13), 1781-1813; Y. Terao, H. Kotaki, N. Imai, K. Achiwa, Chem. Pharm. Bull. (1985), 33 (7), 2762-2766; K. Shankaran et al., Bioorg. Med. Chem. Lett. (2004), (14), 3419-3424).

Scheme 2 details a synthesis of the compounds of formula (I) in which $R_4$ is placed in the 4-position of the carbon ring and represents an aryl or heteroaryl group as defined above; these compounds are referred to hereinafter as compounds of formula (VI).

Scheme 2:

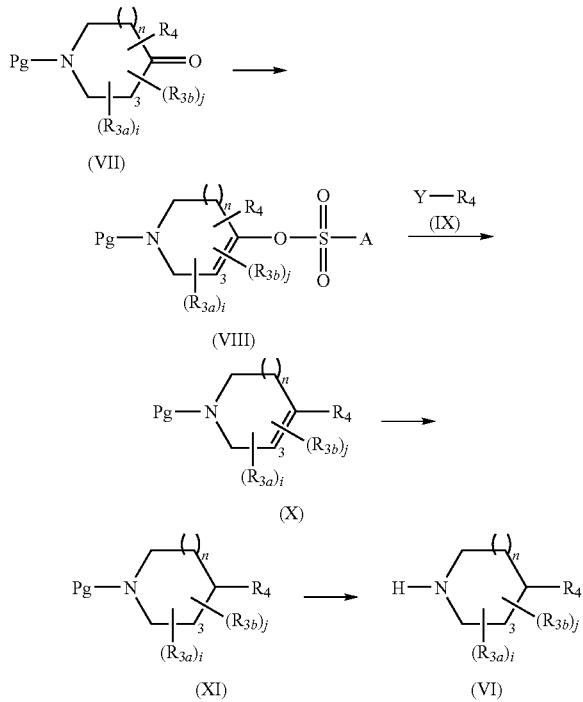

In Scheme 2, the heterocycles (VIII), the amine functional group of which is protected by a protective group Pg (for example, a Boc or Fmoc group), exhibiting a vinyl sulfonate-A group (for example, A can be a trifluoromethyl group or a nonafluorobutyl group) can be prepared by conversion of the ketones (VII) with a sulfonating agent, such as trifluoromethanesulfonic anhydride or N-phenyltrifluoromethanesulfonimide, in the presence of a base, such as lithium diisopropylamide or lithium hexamethyldisilazane, in a solvent, such as tetrahydrofuran or ethylene glycol dimethyl ether, at a temperature varying from −78° C. to ambient temperature. The heterocycles (X) are obtained by organometallic coupling between a compound (VIII) and a compound (IX), where Y is a boron derivative (for example, a boronic acid or a boronic ester), a tin derivative (for example, a tri(n-butyl)tin group) or a halogen atom (for example, bromine or iodine), in the presence of an appropriate metal derivative (for example, palladium, zinc or copper derivatives) in the presence or absence of a base, such as potassium carbonate, potassium fluoride or sodium phosphate, in a solvent or mixture of solvents, such as dioxane, ethylene glycol dimethyl ether, toluene or water, at a temperature varying from ambient temperature to 120° C.

The double bond of the heterocycles (X) is subsequently hydrogenated with an appropriate metal catalyst in methanol or ethanol to result in the derivatives (XI). In a final stage, the amines of formula (VI) are obtained by deprotection of the amine functional group of the compounds of formula (XI) by methods known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10° C. to 100° C.

Scheme 3 presents an alternative route for the preparation of the compounds of formula (I) in which $R_4$ is placed in the 4-position of the carbon ring and represents an aryl or heteroaryl group as defined above; these compounds are referred to hereinafter as compounds of formula (XII). In the case where X represents a nitrogen atom, it has to be substituted either by an $R_{2a,b}$ group (other than H) or by a protective group Pg as defined above.

Scheme 3 (Method 2):

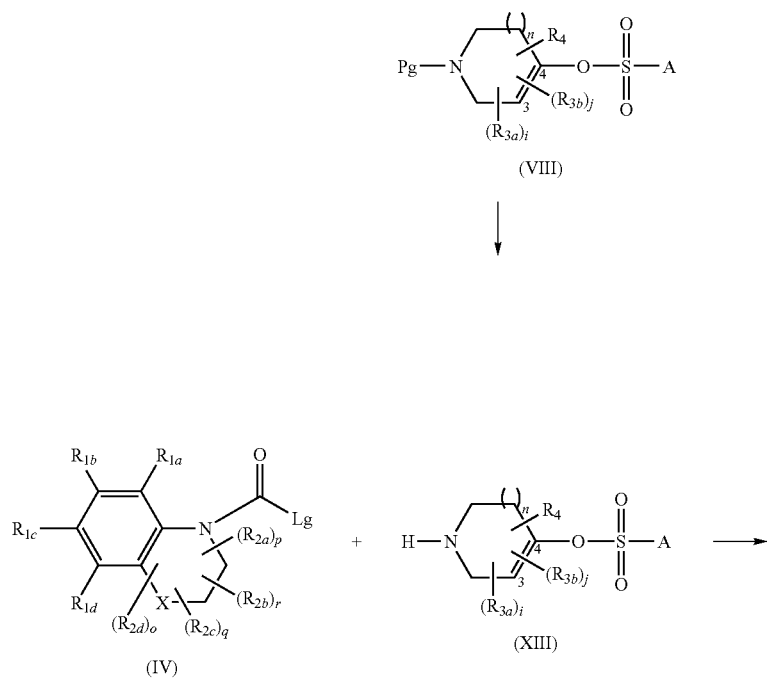

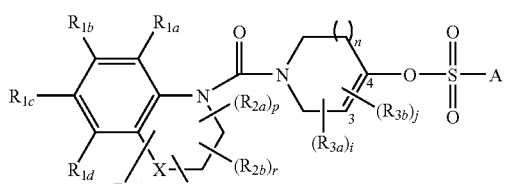
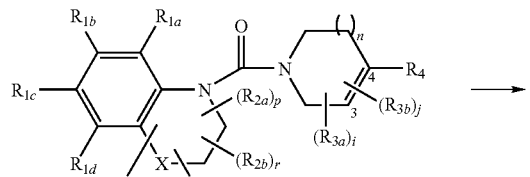

(XIV)    (XV)

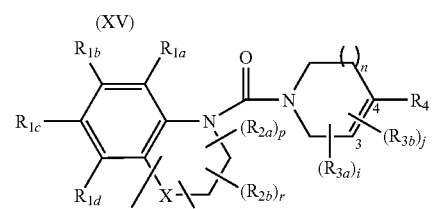

(XII)

In Scheme 3, the amines (XIII) are obtained by deprotection of the amine functional group of the compounds of formula (VIII) by methods chosen from those known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10 to 100° C. The compounds of formula (XIV) are obtained by coupling between the activated derivatives (IV) and the amines (XIII) in the presence or absence of a base, such as triethylamine or potassium carbonate, in a solvent, such as tetrahydrofuran, dichloromethane, acetonitrile or water, at a temperature varying between ambient temperature and 100° C. In the following stage, the heterocycles (XV) are obtained by organometallic coupling between a compound (XIV) and a compound (IX), where Y is a boron derivative (for example, a boronic acid or a boronic ester), a tin derivative (for example, a tri(n-butyl)tin group) or a halogen atom (for example, bromine or iodine), in the presence of an appropriate metal derivative (for example, palladium, zinc or copper derivatives) and in the presence or absence of a base, such as potassium carbonate, potassium fluoride or sodium phosphate, in a solvent or mixture of solvents, such as dioxane, ethylene glycol dimethyl ether, toluene or water, at a temperature varying from ambient temperature to 120° C. In a final stage, the double bond of the heterocycles (XV) is subsequently hydrogenated with an appropriate metal in methanol or ethanol to result in the derivatives (XII).

Scheme 4 presents a route for the synthesis of the compounds of formula (I) in which i represents 1 and $R_{3a}$ is a CN group placed in the 4-position and $R_4$ is placed in the 4-position of the carbon ring and represents an aryl or heteroaryl group as defined above; these compounds are referred to hereinafter as compounds of formula (XVI). In the case where X represents a nitrogen atom, it has to be substituted either by an $R_{2a,b,c,d}$ group (other than H) or by a protective group Pg as defined above.

Scheme 4 (Method 3):

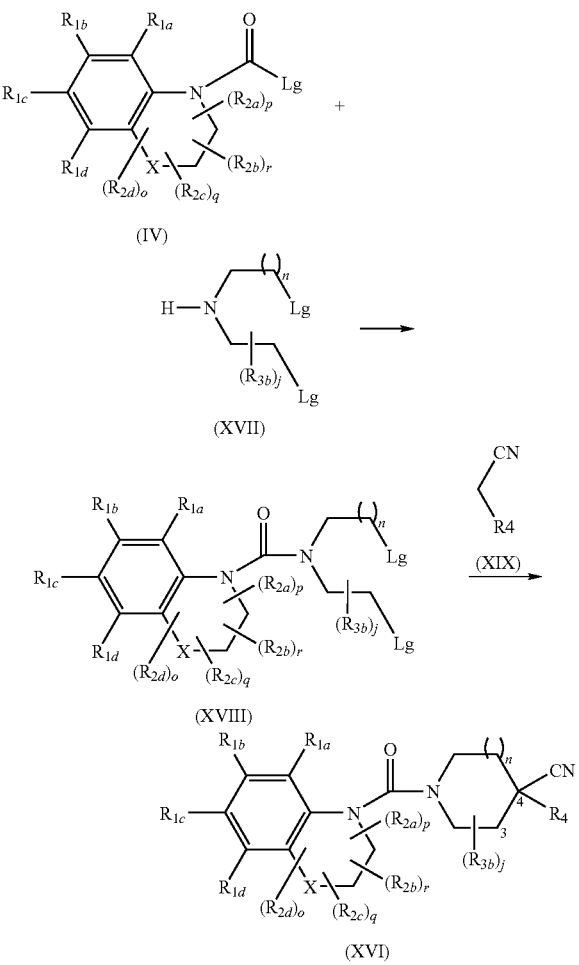

In Scheme 4, the compounds of formula (XVIII) are obtained by coupling between the activated derivatives (IV) and the amines (XVII) exhibiting two leaving groups Lg (for example chlorine atoms or mesyl or tosyl groups) in the presence or absence of a base, such as triethylamine or potassium carbonate, in a solvent, such as tetrahydrofuran, dichloromethane or acetonitrile, at a temperature varying from ambient temperature to 100° C. In the final stage, the compounds (XVI) are obtained by the reaction of the nitriles (XIX) with the derivatives (XVIII) in the presence of a base, such as sodium hydride or lithium diisopropylamide or hexamethyldisilazane, in a solvent, such as tetrahydrofuran, at a temperature varying from −5° C. to 80° C.

Scheme 5 presents an alternative route for the synthesis of the compounds of formula (I) in which i represents 1, $R_{3a}$ is a CN group placed in the 4-position and $R_4$ is placed in the 4-position of the carbon ring and represents an alkyl or cycloalkyl group as defined above; these compounds are referred to hereinafter as compounds of formula (XVI)'. In the case where X represents a nitrogen atom, it has to be substituted either by an $R_{2a,b,c,d}$ group (other than H) or by a protective group Pg as defined above.

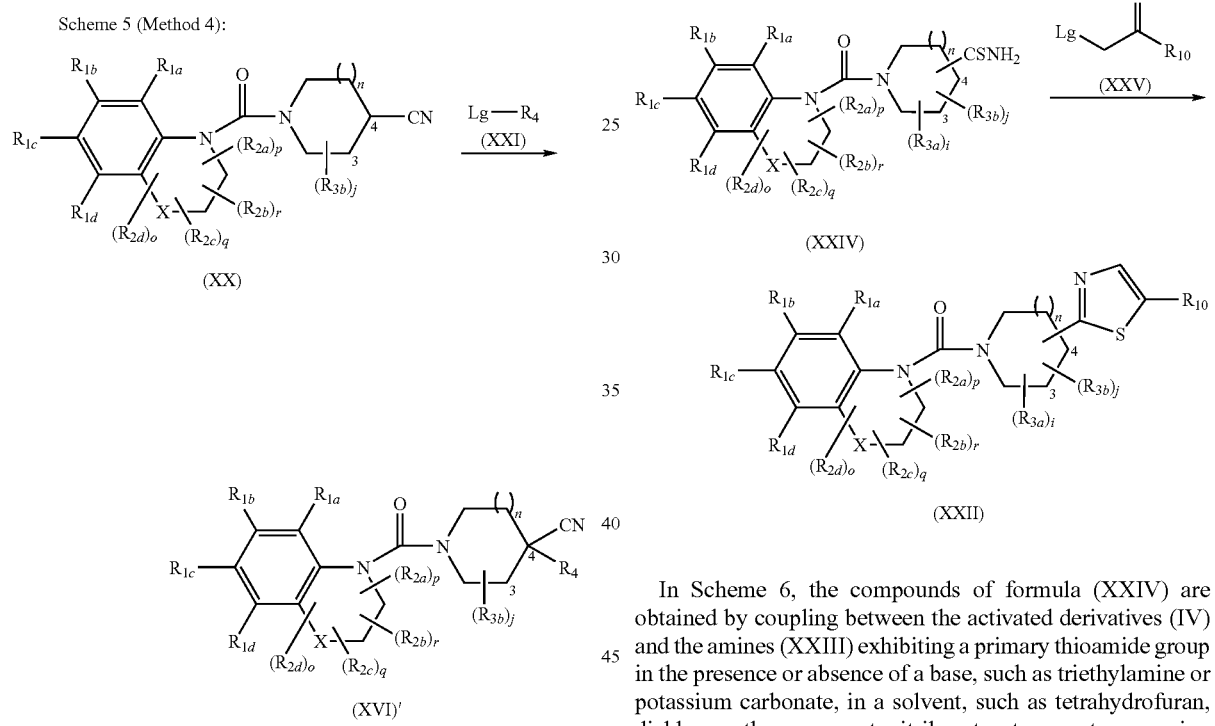

In Scheme 5, the compounds of formula (XVI)' are obtained by alkylation of the compounds (XX) with the compounds (XXI) exhibiting a leaving group Lg (for example, a chlorine atom or a mesyl or tosyl group) in the presence of a base, such as sodium hydride, lithium diisopropylamide, lithium hexamethyldisilazane or lithium amide, in a solvent, such as tetrahydrofuran, at a temperature varying from −78° C. to ambient temperature.

Scheme 6 presents a route for the preparation of the compounds of formula (I) in which $R_4$ is a thiazole group substituted by an $R_{10}$ group where $R_{10}$ represents a hydrogen atom, a $(C_1-C_5)$alkyl group or an aryl group which is optionally substituted; these compounds are referred to hereinafter as compounds of formula (XXII). In the case where X represents a nitrogen atom, it has to be substituted either by an $R_{2a,b,c,d}$ group (other than H) or by a protective group Pg as defined above.

In Scheme 6, the compounds of formula (XXIV) are obtained by coupling between the activated derivatives (IV) and the amines (XXIII) exhibiting a primary thioamide group in the presence or absence of a base, such as triethylamine or potassium carbonate, in a solvent, such as tetrahydrofuran, dichloromethane or acetonitrile, at a temperature varying from ambient temperature to 100° C. In the final stage, the compounds (XXII) are obtained by the reaction of the thioamides (XXIV) with the oxo derivatives (XXV) exhibiting a leaving group Lg (for example, a chlorine or bromine atom) in the alpha position, where $R_{10}$ represents a hydrogen atom, an alkyl group or an aryl group which is optionally substituted, in the presence of a base, such as triethylamine or diisopropylethylamine, in a solvent, such as tetrahydrofuran or acetonitrile, at a temperature varying from ambient temperature to 80° C.

Scheme 7 presents a route for the preparation of the compounds of formula (I) in which $R_4$ is a 1,2,4-oxadiazole group substituted by an $R_{11}$ group where $R_{11}$ represents a $(C_1-C_5)$ alkyl group or an aryl group which is optionally substituted; these compounds are referred to hereinafter as compounds of formula (XXVI). In the case where X represents a nitrogen atom, it has to be substituted either by an $R_{2a,b,c,d}$ group (other than H) or by a protective group Pg as defined above.

Scheme 7 (Method 6):

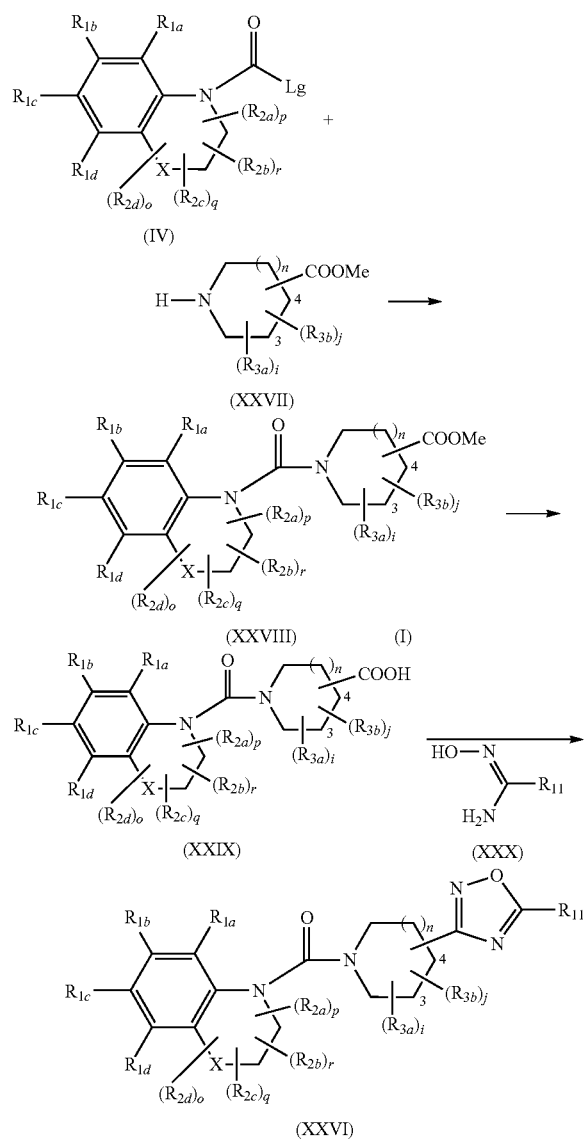

Scheme 8 (Method 7):

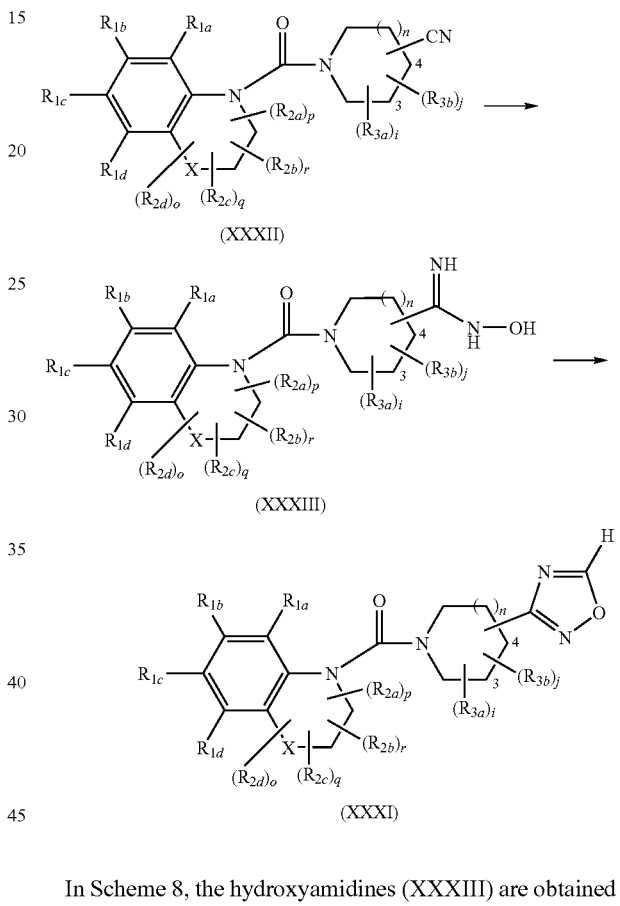

such as dimethylformamide, tetrahydrofuran or acetonitrile, at a temperature varying between ambient temperature and 100° C.

Scheme 8 presents a route for the synthesis of the compounds of formula (I) in which $R_4$ is a 1,2,4-oxadiazole group; these compounds are referred to hereinafter as compounds of formula (XXXI). In the case where X represents a nitrogen atom, it has to be substituted either by an $R_{2a,b,c,d}$ group (other than H) or by a protective group Pg as defined above.

In Scheme 7, the compounds of formula (XXVIII) are obtained by coupling between the activated derivatives (IV) and the amines (XXVII) exhibiting an ester group in the presence or absence of a base, such as triethylamine or potassium carbonate, in a solvent, such as tetrahydrofuran, dichloromethane or acetonitrile, at a temperature varying from ambient temperature to 100° C. The following stage consists of the saponification of the ester functional group of the compounds (XXVIII) to give an acid group using sodium hydroxide, potassium hydroxide or lithium hydroxide in a solvent, such as an alcohol or water, at a temperature varying from ambient temperature to 100° C., to result in the acids (XXIX). In the final stage, the compounds (XXIX) are obtained by the reaction of the acids (XXVI) with the hydroxyamidine derivatives (XXX), where $R_{11}$ represents an alkyl group or an aryl group which is optionally substituted, in the presence of a coupling agent, such as O-benzotriazol-1-yl-N,N,N',N'-tetramethyluronium tetrafluoroborate, in the presence or absence of 1-hydroxybenzotriazole, of a base, such as triethylamine or diisopropylethylamine, in a solvent, In Scheme 8, the hydroxyamidines (XXXIII) are obtained by reaction of the nitriles (XXXII) with hydroxylamine in the presence or absence of a base, such as triethylamine, in a solvent, such as methanol or ethanol, at a temperature varying between ambient temperature and 100° C. The oxadiazoles (XXXI) are obtained by condensation of the hydroxyamidines (XXXIII) with a formic acid derivative, such as triethyl orthoformate, in the presence or absence of a solvent, such as ethanol, at a temperature of between ambient temperature and 100° C.

Scheme 9 presents a route for the synthesis of the compounds of formula (I) in which $R_4$ is an imidazole group substituted by an $R_{11}$ group, where $R_{11}$ represents a ($C_1$-$C_5$) alkyl group or a benzyl group which is optionally substituted; these compounds are referred to hereinafter as compounds of formulae (XXXIV) and (XXXV). In the case where X represents a nitrogen atom, it has to be substituted either by an $R_{2a,b,c,d}$ group (other than H) or by a protective group Pg as defined above.

Scheme 9 (Method 8):

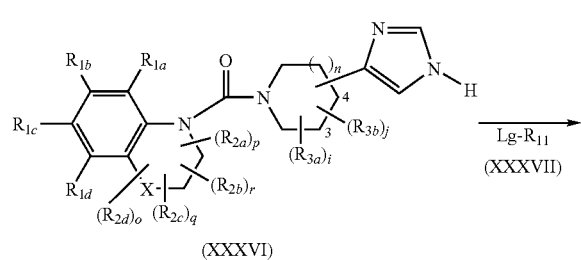

(XXXVI)

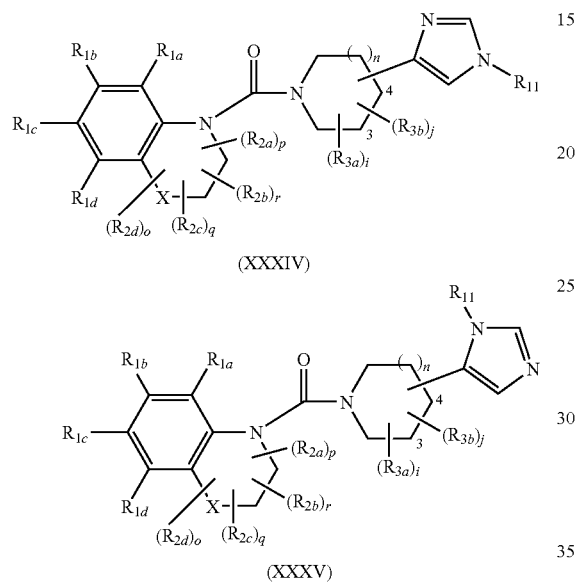

(XXXIV)

(XXXV)

In Scheme 9, the mixture of the substituted imidazoles (XXXIV) and (XXXV) is obtained by alkylation of the imidazoles (XXXVI) with alkylating agents (XXXVII) exhibiting a leaving group Lg (for example, an iodine atom, a bromine atom or a mesyl or tosyl group), where $R_{11}$ represents a $(C_1-C_5)$alkyl group or a benzyl group which is optionally substituted, in the presence of a base, such as triethylamine or potassium carbonate, in a solvent, such as dimethylformamide or tetrahydrofuran, at a temperature varying from 0° C. to 80° C.

Scheme 10 presents a route for the synthesis of the compounds of formula (I) in which p represents 1 and X is a nitrogen atom substituted by the $R_{2a}$ group; these compounds are referred to hereinafter as compounds of formula (XXXVIII).

Scheme 10 (Method 9):

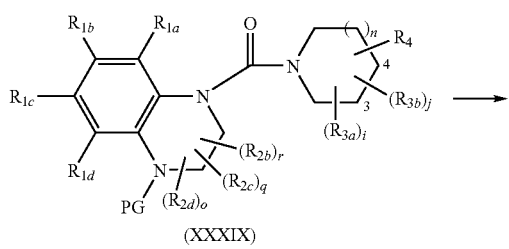

(XXXIX)

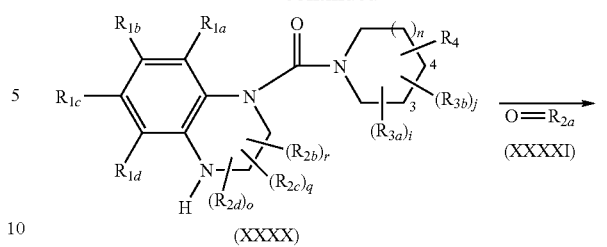

(XXXX)

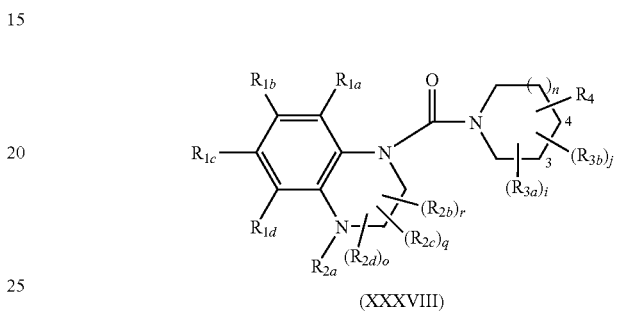

(XXXVIII)

In Scheme 10, the quinoxalines (XXXX) are obtained by deprotection of the amine functional group of the compounds of formula (XXXIX) by methods chosen from those known to a person skilled in the art. These methods comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10 to 100° C. In a final stage, the substituted quinoxalines of formula (XXXVIII) are obtained by reductive amination carried out by bringing together the compounds of formula (XXXX) and a derivative of the $R_{2a}$ group of aldehyde or ketone type using a reducing agent, such as sodium borohydride, sodium triacetoxyborohydride or sodium cyanoborohydride, in the presence or absence of a Brönsted acid (such as hydrochloric acid) or Lewis acid (such as titanium tetraisopropoxide) in a solvent, such as dichloroethane, dichloromethane, acetic acid or methanol, at temperatures of between −10° C. and 30° C.

Scheme 11 presents a route for the synthesis of the compounds of formula (I) in which X is a nitrogen atom, p represents 1, $R_{2a}$ is a CO—N($R_{12}$,$R_{13}$) group which substitutes X, and $R_{12}$ and $R_{13}$ represent $R_6$ and $R_7$ as defined in the formula (I); these compounds are referred to hereinafter as compounds of formula (XXXXII).

Scheme 11 (Method 10):

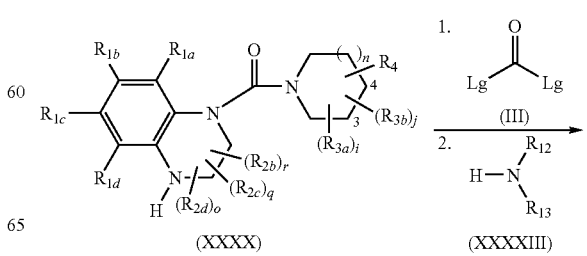

(XXXX)   (XXXXIII)

-continued (XXXXII)

In Scheme 11, in order to result in ureas (XXXXII), the quinoxalines (XXXX) react, in a first step, with a carbonyl of formula (III) exhibiting two leaving groups Lg (for example, a chlorine atom, a trichloromethoxy group, a para-nitrophenyl group or an imidazole or methylimidazolium group) in the presence of a base, such as triethylamine or diisopropylamine, in a solvent, such as dichloromethane or tetrahydrofuran, at a temperature varying from ambient temperature to 80° C. Then, in a second step, the ureas (XXXXII) are obtained by reacting with the amines (XXXXIII) in the presence or absence of a base, such as triethylamine or potassium carbonate, in a solvent, such as tetrahydrofuran, dichloromethane, acetonitrile or water, at a temperature varying from ambient temperature to 100° C.

Scheme 12 presents a route for the synthesis of the compounds of formula (I) in which X is a nitrogen atom, p represents 1, $R_{2a}$ is a CO—$OR_{14}$ group which substitutes X, and $R_{14}$ represents $R_5$ as defined in the formula (I); these compounds are referred to hereinafter as compounds of formula (XXXXIV).

Scheme 12 (Method 11):

(XXXX)

(XXXXV)

(XXXXIV)

In Scheme 12, in order to result in the carbamates (XXXXIV), the quinoxalines (XXXX) react first with a carbonyl of formula (III) exhibiting two leaving groups Lg (for example, a chlorine atom, a trichloromethoxy group, a para-nitrophenyl group or an imidazole or methylimidazolium group) in the presence of a base, such as triethylamine or diisopropylamine, in a solvent, such as dichloromethane or tetrahydrofuran, at a temperature varying from ambient temperature to 80° C.; then, in a second step, with the alcohols (XXXXV) in the presence or absence of a base, such as triethylamine or potassium carbonate, in a solvent, such as tetrahydrofuran, dichloromethane, acetonitrile or water, at a temperature varying from ambient temperature to 100° C., in order to result in the carbamates (XXXXIV).

Scheme 13 presents a route for the synthesis of the compounds of formula (I) in which X is a nitrogen atom, p represents 1, $R_{2a}$ is a $COR_{15}$ group which substitutes X, and $R_{15}$ represents $R_5$ as defined in the formula (I); these compounds are referred to hereinafter as compounds of formula (XXXXVI).

Scheme 13 (Method 12):

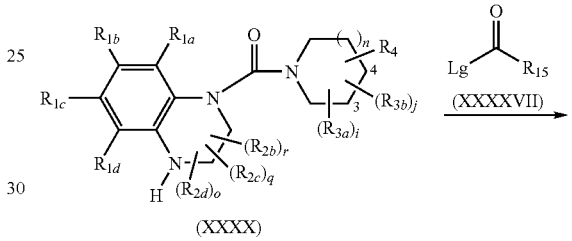

(XXXX)

(XXXXVI)

In Scheme 13, in order to result in the amides (XXXXVI), the quinoxalines (XXXX) react with an acid derivative of formula (XXXXVII) exhibiting a leaving group Lg (for example, a chlorine atom, a trichloromethoxy group, a para-nitrophenyl group or an imidazole or methylimidazolium group) in the presence of a base, such as triethylamine or diisopropylamine, in a solvent, such as dichloromethane or tetrahydrofuran, at a temperature varying from ambient temperature to 80° C.

Scheme 14 presents a route for the synthesis of the compounds of formula (I) in which one of the $R_1$ groups is a —COOH group (for example placed hereinafter in the $R_{1c}$ position) and of the compounds of formula (IC) in which one of the $R_1$ groups is a —$CH_2OH$ group; these compounds are referred to hereinafter as compounds of formula (XXXX-VIII).

Scheme 14 (Method 13):

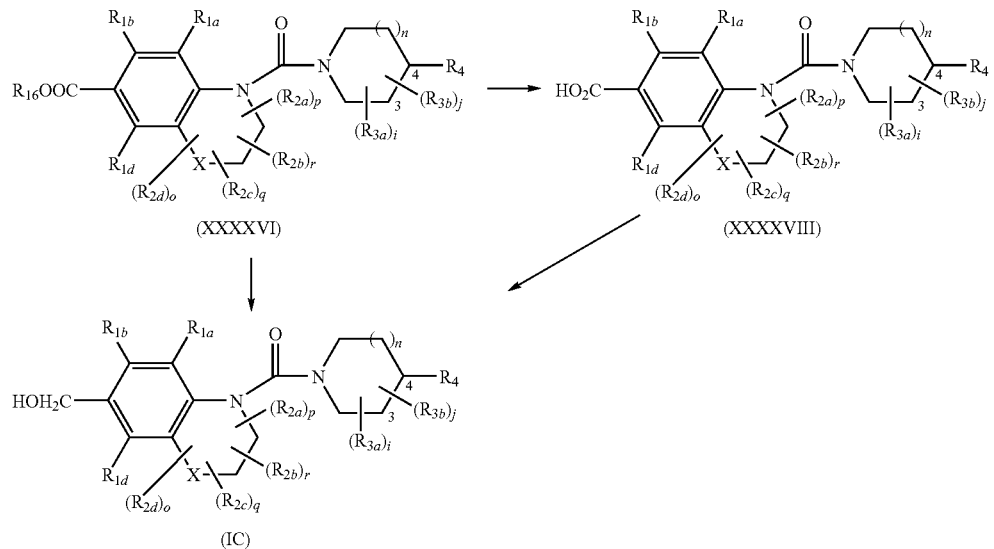

The compounds of formula (XXXXVIII) can be synthesized by saponification of the esters of formula (XXXXVI), for example in the presence of sodium hydroxide or lithium hydroxide, in a solvent, such as methanol, tetrahydrofuran or water, or a mixture of these solvents. The compounds of formula (IC) are obtained by reduction of the acids (XXXXVIII) or the esters of formula (XXXXVI) using reducing agents, such as lithium aluminum hydride or, after formation of a mixed anhydride in the presence of isobutyl chloroformate and of triethylamine in tetrahydrofuran or dioxane, sodium borohydride in methanol or ethanol at temperatures varying from −40° C. to 10° C.

Scheme 15 presents two access routes to the synthetic intermediates of formula (C) in which $R_{17}$ is a hydrogen atom or a $(C_1-C_5)$alkoxy or $(C_1-C_5)$haloalkyl group and L a linker (single bond, $(C_1-C_5)$alkoxy group, $(C_1-C_5)$alkyl group) and $R_{16}$ is defined as above.

Scheme 15

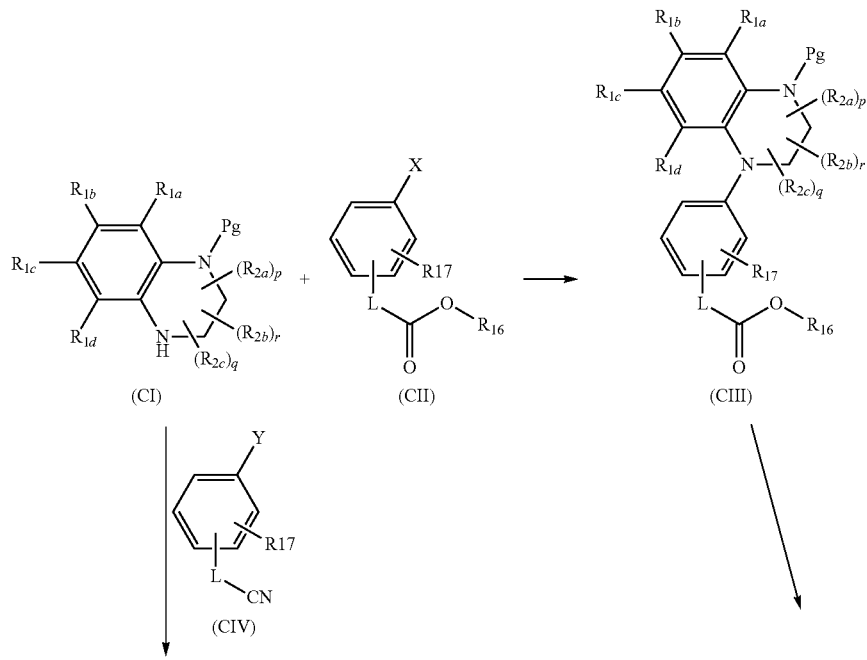

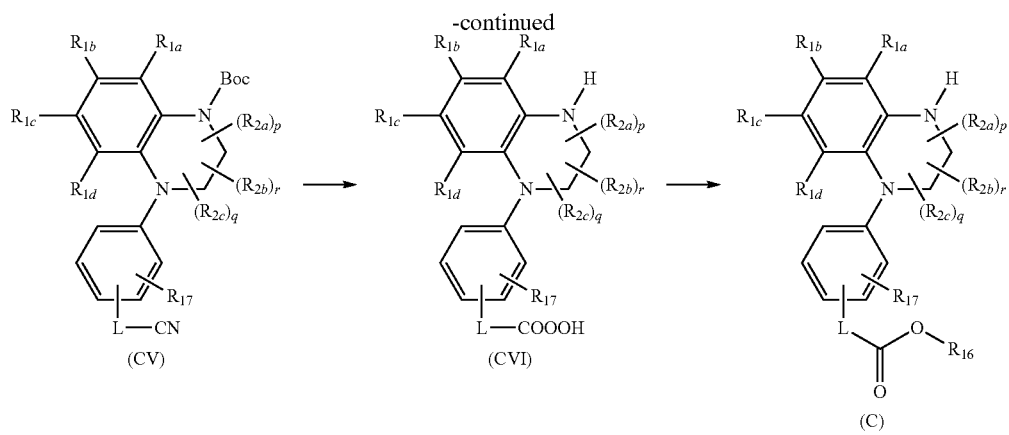

In Scheme 15, the compounds of formula (CIII) can be prepared by coupling between a monoprotected tetrahydroquinoxaline of formula (CI) and a derivative (CII) exhibiting a group X (for example, a halogen or a tosylate, triflate or nanoflate group) in the presence of an organometallic entity, such as a palladium derivative, in the presence or absence of a phosphine, such as tri(tert-butyl)phosphine or triphenylphosphine, in the presence of a base, such as potassium carbonate, potassium fluoride, potassium tert-butoxide or potassium phosphate, in a solvent or mixture of solvents, such as dioxane, ethylene glycol dimethyl ether, toluene, tetrahydrofuran or water, at a temperature varying from ambient temperature to 100° C. The amines (C) are obtained by deprotection of the amine functional group of the compounds of formula (CIII) by methods chosen from those known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10 to 100° C. An alternative approach to the synthesis of the intermediates (C) consists in carrying out a nucleophilic aromatic substitution reaction between the monoprotected tetrahydroquinoxaline (CI), where the protective group is a "Boc" group, and an aromatic cyano derivative (CIV), in which Y is a halogen atom (for example fluorine), in the presence of a base, such as potassium tert-butoxide or sodium hexamethyldisilazane, in a solvent, such as N-methylpyrrolidinone or dimethylformamide, at a temperature varying from ambient temperature to 100° C. The cyano functional group of the compounds (CV) is subsequently hydrolyzed in an acidic medium using, for example, a solution of concentrated hydrochloric acid in a solvent, such as water, at a temperature varying from ambient temperature to 100° C., to result in the acids (CVI) from which the "Boc" protective group has been simultaneously removed. Finally, the ester (C) is obtained by esterification of the acid derivative (CVI) with an alcohol $HOR_{16}$ under conventional peptide coupling conditions, using, for example, as coupling agent, dicyclohexylcarbodiimide, 1-(3-dimethylaminopropyl)-3-ethylcarbodiimide hydrochloride or bromotrispyrrolidinophosphonium hexafluorophosphate, in the presence or absence of hydroxybenzotriazole, and using, as organic base, triethylamine or diisopropylethylamine in a solvent, such as dioxane, dichloromethane or acetonitrile.

Scheme 16 presents a route for the synthesis of the compounds of formula (CVII) which correspond to compounds of formula (I) in which $R_{2d}$ comprises $L_2$, which is a linker (single bond or $(C_1-C_5)$alkyl group), and L and $R_{17}$ are defined as above.

Scheme 16 (Method 14)

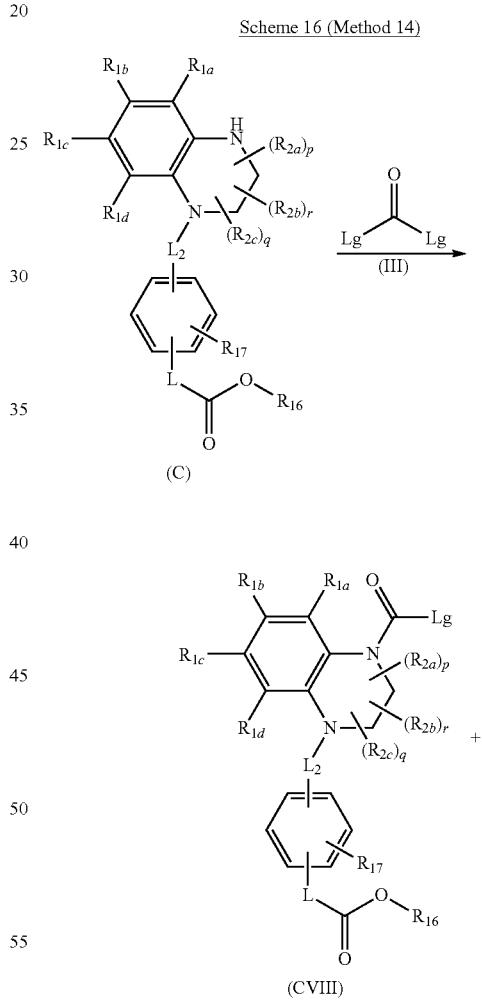

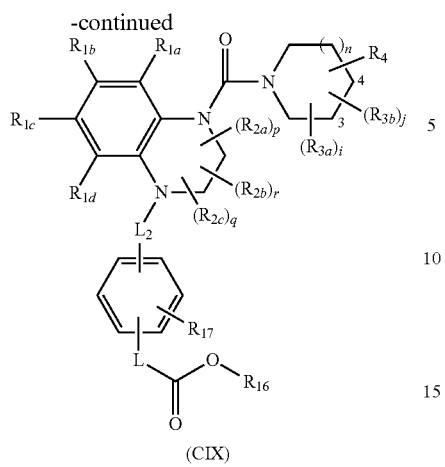

(CIX)

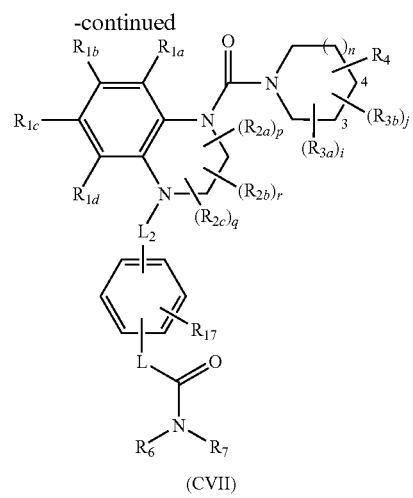

(CVII)

In Scheme 16, the compounds of formula (CVIII) can be prepared by reaction between the intermediates of formula (C) and a carbonyl of formula (III) exhibiting two leaving groups Lg (for example, a chlorine atom, a trichloromethoxy group, a para-nitrophenyl group or an imidazole or methylimidazolium group) in the presence of a base, such as triethylamine or diisopropylamine, in a solvent, such as dichloromethane or tetrahydrofuran, at a temperature varying from ambient temperature to 80° C. The compounds of formula (CIX) are obtained by coupling between the activated derivatives (CVIII) and the amines (V) in the presence or absence of a base, such as triethylamine or potassium carbonate, in a solvent, such as tetrahydrofuran, dichloromethane, acetonitrile or water, at a temperature varying from ambient temperature to 100° C. The ester functional group of the compounds (CIX) is subsequently saponified to give an acid functional group using sodium hydroxide, potassium hydroxide or lithium hydroxide in a solvent or a mixture of solvents, such as an alcohol, water or tetrahydrofuran, at a temperature varying from ambient temperature to 100° C., in order to result in the acids (CX). In the final stage, the compounds (CVII) can be prepared by condensation between the acid intermediates of formula (CX) and an amine (CXI) under conventional peptide coupling conditions, using, for example, as coupling agent, dicyclohexylcarbodiimide, 1-(3-dimethylaminopropyl)-3-ethylcarbodiimide hydrochloride or bromotrispyrrolidinophosphonium hexafluorophosphate, in the presence or absence of hydroxybenzotriazole, and using, as organic base, triethylamine or diisopropylethylamine in a solvent or mixture of solvents, such as dioxane, dichloromethane or acetonitrile.

Scheme 17 presents an alternative route for the synthesis of the intermediates of formula (XV) as defined above.

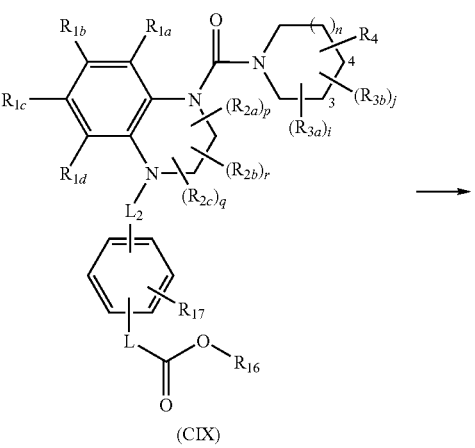

(CIX)

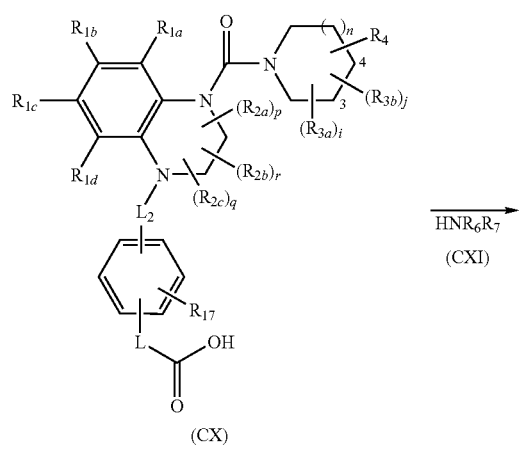

(CX)

HNR$_6$R$_7$
(CXI)

Scheme 17:

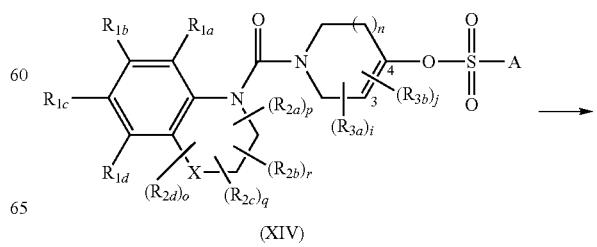

(XIV)

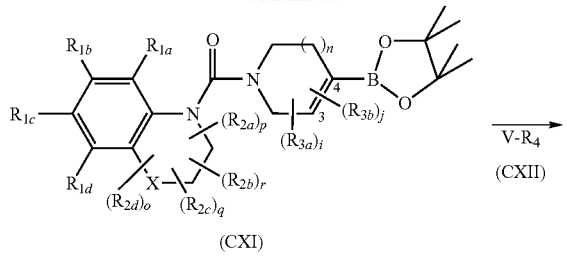

(CXI)

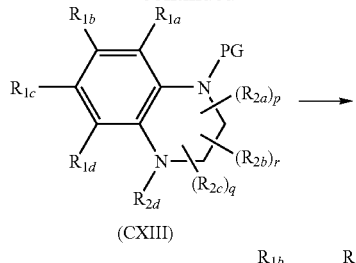

(CXIII)

(CXV)

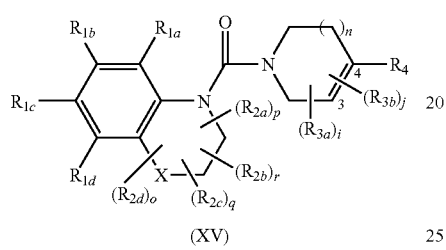

(XV)

In Scheme 17, the compounds of formula (CXI) can be prepared by conversion of the sulfonic ester functional group of the compounds (XIV) to a boronic ester derivative (CXI) by a reaction with bis(pinacolato)diboron in the presence of a palladium complex, such as 1,1'-bis(diphenylphosphino)ferrocenedichloropalladium(II), in the presence of a base, such as potassium acetate or lithium chloride, in a solvent or mixture of solvents, such as dichloromethane, dioxane or dimethyl sulfoxide, at a temperature varying from ambient temperature to 100° C. In a second stage, the derivatives (XV) can be obtained by a coupling reaction between the derivative (CXI) and a compound (CXII) exhibiting a group V (for example, a halogen, a triflate or a nonaflate) in the presence of an organometallic entity, such as a palladium derivative, in the presence or absence of a phosphine, such as tricyclohexylphosphine or triphenylphosphine, in the presence of a base, such as sodium carbonate, potassium carbonate or potassium fluoride, in a solvent or mixture of solvents, such as dioxane, dimethylformamide, ethylene glycol dimethyl ether, tetrahydrofuran or water, at a temperature varying from ambient temperature to 100° C.

Scheme 18 presents an alternative route for the synthesis of the compounds of formula (XXXVIII) in which $R_{2d}$ is a ($C_1$-$C_5$)alkyl, aryl($C_1$-$C_5$)alkyl or heteroaryl($C_1$-$C_5$)alkyl group (it being possible for the aryl or heteroaryl groups optionally to be substituted).

Scheme 18 (Method 15):

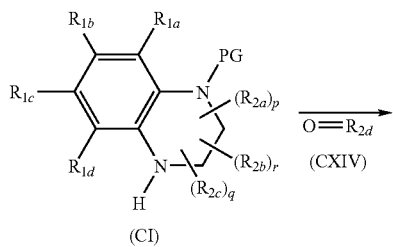

(CI)

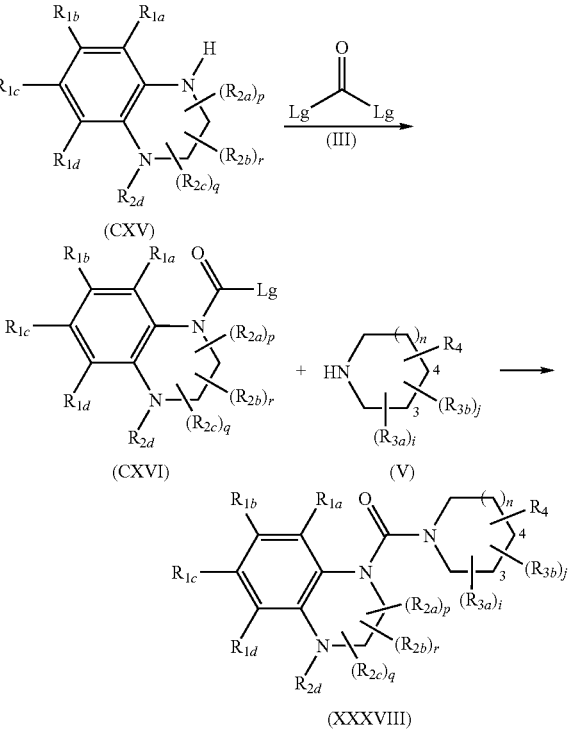

The substituted tetrahydroquinoxalines of formula (CXIII) are obtained by reductive amination, carried out by bringing the compounds of formula (CI) into contact with a derivative of the $R_{2d}$ group of aldehyde or ketone type (CXIV) while using a reducing agent, such as sodium borohydride, sodium triacetoxyborohydride or sodium cyanoborohydride, in the presence or absence of a Brönsted acid (such as hydrochloric acid) or a Lewis acid (such as titanium tetraisopropoxide) in a solvent, such as dichloroethane, dichloromethane, acetic acid or methanol, at temperatures of between −10° C. and 30° C. The amines (CXV) are obtained by deprotection of the amine functional group of the compounds of formula (CXIII) by methods chosen from those known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10 to 100° C. In a following stage, the compounds of formula (CXVI) can be prepared by reaction between intermediates of formula (CXV) and a carbonyl of formula (III) exhibiting two leaving groups Lg (for example, a chlorine atom, a trichloromethoxy group, a para-nitrophenyl group, or an imidazole or methylimidazolium group) in the presence of a base, such as triethylamine or diisopropylamine, in a solvent, such as dichloromethane or tetrahydrofuran, at a temperature varying from ambient temperature to 80° C. The compounds of formula (XXXVIII) are obtained by coupling between the activated derivatives (CXVI) and the amines (V) in the presence or absence of a base, such as triethylamine or potassium carbonate in a solvent, such as tetrahydrofuran, dichloromethane, acetonitrile or water, at a temperature varying from ambient temperature to 100° C.

Scheme 19 presents a route for the synthesis of the intermediates of formula (CXVII) where the carbon atom which carries the spiro cyclopropyl group is not adjacent to the nitrogen atom of the tetrahydroquinoline.

Scheme 19:

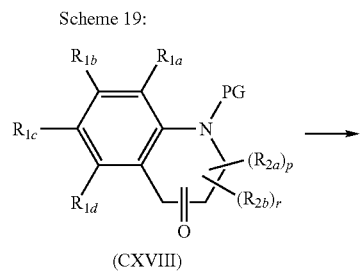

(CXVIII)

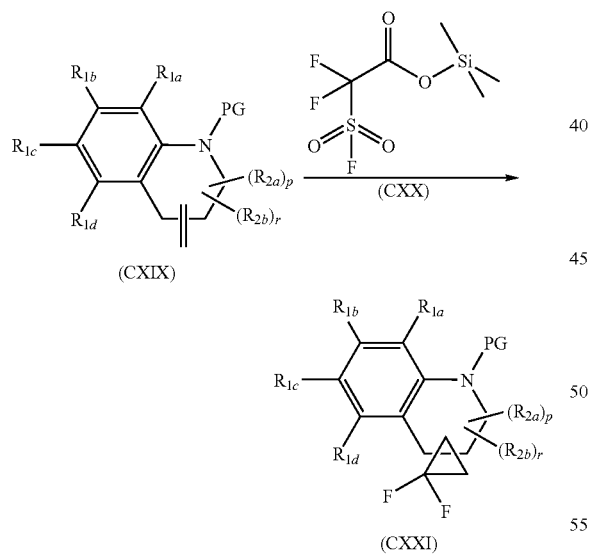

(CXIX)

(CXXI)

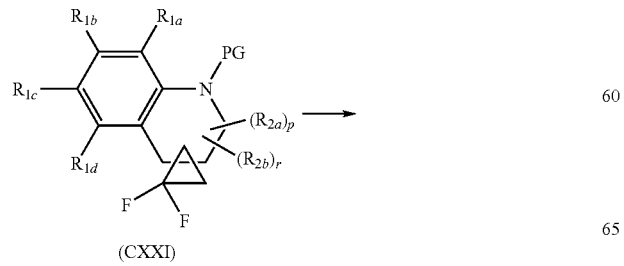

(CXXI)

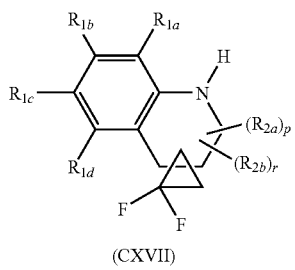

(CXVII)

The compounds (CXIX) can be obtained by conversion of the ketone functional group of the intermediate (CXVIII) to an ethylenic derivative using, for example, a Wittig reaction with methyltriphenylphosphonium bromide in the presence of a base, such as potassium tert-butoxide, in a solvent, such as ether. The spirocyclopropane derivatives (CXXI) can subsequently be obtained by the use of trimethylsilyl fluorosulfonyldifluoroacetate (CXX) in the presence of a fluorine source, such as sodium fluoride, in a solvent, such as toluene, at a temperature varying from ambient temperature to 100° C. The amines (CXVII) are obtained by deprotection of the amine functional group of the compounds of formula (CXXI) by methods chosen from those known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10 to 100° C.

Scheme 20 presents a route for the synthesis of the intermediates of formula (CXXIII) where the difluorovinyl group is not adjacent to the nitrogen atom of the tetrahydroquinoline.

Scheme 20:

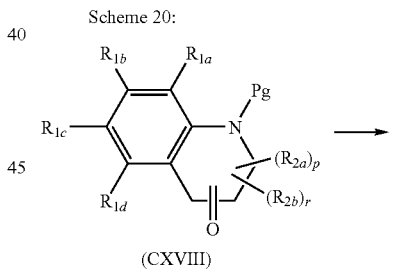

(CXVIII)

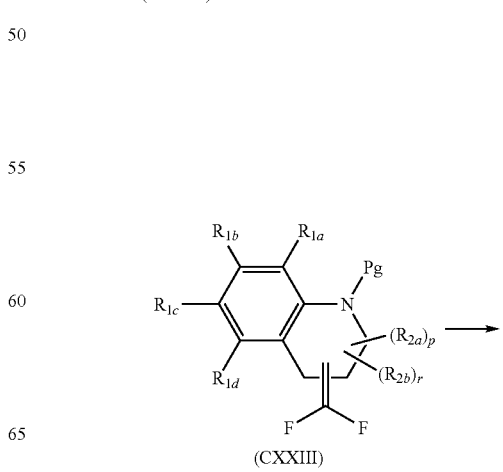

(CXXIII)

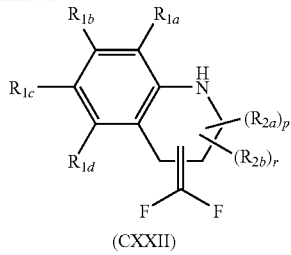

The compounds (CXXIII) can be obtained by conversion of the ketone functional group of the intermediate (CXVIII) to a difluoroethylenic derivative using, for example, a Wittig reaction with tri(n-butyl)phosphine and sodium chlorodifluoroacetate in a solvent, such as N-methylpyrrolidinone, at a temperature varying from ambient temperature to 160° C. The amines (CXVII) are obtained by deprotection of the amine functional group of the compounds of formula (CXXI) by methods chosen from those known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10 to 100° C.

Scheme 21 details a racemic synthesis of pyrrolidine of formula (CXXXI) in which $R_3$ cannot be carried by the same carbon as Ar, and also the separation of the two enantiomers (CXXIV) and (CXXV), Ar being an optionally substituted aryl or heteroaryl group and $R_3$ being as defined above.

Scheme 21:

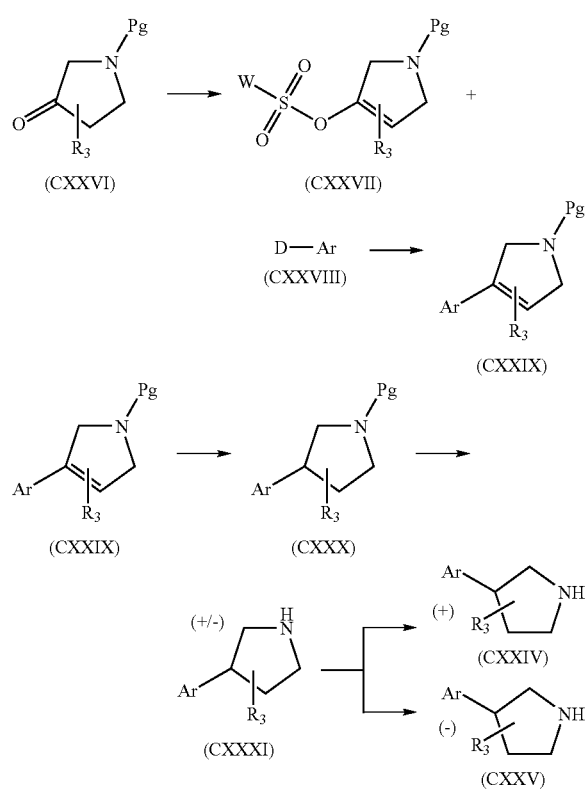

In Scheme 21, the heterocycles (CXXVII), the amine functional group of which is protected by a protective group Pg (for example, a Boc or Fmoc group), exhibiting a vinyl sulfonate-W group (for example, W can be a trifluoromethyl group or a nonafluorobutyl group) can be prepared by conversion of the ketones (CXXVI) with a sulfonating agent, such as trifluoromethanesulfonic anhydride or N-phenyltrifluoromethanesulfonimide, in the presence of a base, such as lithium diisopropylamide or lithium hexamethyldisilazane, in a solvent, such as tetrahydrofuran or ethylene glycol dimethyl ether, at a temperature varying from −78° C. to ambient temperature. The heterocycles (CXXIX) are obtained by organometallic coupling between a derivative (CXXVII) and a compound (CXXVIII), where D is a boron derivative (for example, a boronic acid or a boronic ester), a tin derivative (for example, a tri(n-butyl)tin group) or a halogen atom (for example, bromine or iodine), in the presence of an appropriate metal derivative (for example, palladium, zinc or copper derivatives) in the presence or absence of a base, such as potassium carbonate, potassium fluoride or sodium phosphate, in a solvent or mixture of solvents, such as dioxane, ethylene glycol dimethyl ether, toluene or water, at a temperature varying from ambient temperature to 120° C. In the case where the Ar group is a pyrazole, if the free NH functional group of the heterocycle is present, it can optionally be protected by a protective group (for example, a Boc group) before carrying out the coupling reaction catalyzed by an organometallic entity. Generally, during the coupling reaction, the protective group (especially if it is a Boc group) is partially or completely removed from the pyrazole ring. The double bond of the heterocycles (CXXIX) is subsequently hydrogenated with an appropriate metal catalyst in methanol or ethanol to result in the derivatives (CXXX). In a final synthetic stage, the amines of formula (CXXXI) are obtained by deprotection of the amine functional group of the compounds of formula (CXXX) by methods known to a person skilled in the art. They comprise, inter alia, the use of trifluoroacetic acid or hydrochloric acid in dichloromethane, dioxane, tetrahydrofuran or diethyl ether, in the case of protection by a Boc group, and piperidine, for a Fmoc group, at temperatures varying from −10° C. to 100° C.

The mixture of the two enantiomers (CXXIV) and (CXXV) can be separated using methods known to a person skilled in the art, in particular by supercritical or high-pressure chromatography on a chiral stationary phase, such as an amylose tris(3,5-dimethylphenylcarbamate) derivative deposited on a spherical silica support, or by recrystallization in the presence of an optically active acid, such as tartaric acid or camphorsulfonic acid.

In Schemes 1 to 21, the starting compounds and the reactants, when their method of preparation is not described, are available commercially or are described in the literature or else can be prepared according to methods which are described therein or which are known to a person skilled in the art. Generally, the derivatives with an acid group can also be obtained conventionally by hydrolysis of the corresponding cyano groups.

According to another of its aspects, another subject matter of the invention is the compounds of formulae (XIV), (XV), (XVIII), (XXIV), (XXIX), (XXVIII), (XXXIII), (C), (CIX), (CX), (CXVII) and (CXXII). These compounds are of use as intermediates in the synthesis of the compounds of formula (I).

EXAMPLES

The following examples describe the preparation of some compounds in accordance with the invention. These examples are not limiting and serve only to illustrate the

Example 1

1'-(3,4-Dihydroquinolin-1(2H)-ylcarbonyl)spiro[indene-1,4'-piperidine] (Compound No. 15)

1.1: 4-Nitrophenyl 3,4-dihydroquinoline-1(2H)-carboxylate 10 g of 1,2,3,4-tetrahydroquinoline, 10.46 ml of triethylamine, 270 ml of tetrahydrofuran and then 15.13 g of paranitrophenyl chloroformate are introduced into a 1 l round-bottomed flask. The reaction medium is stirred at ambient temperature for two hours and then filtered. The solvent is evaporated under reduced pressure and the residue is taken up in dichloromethane and washed with a 2N aqueous hydrochloric acid solution and then twice with water. The organic phase is dried over magnesium sulfate and the solvent is evaporated under reduced pressure to result in 21.5 g of 4-nitrophenyl 3,4-dihydroquinoline-1(2H)-carboxylate.

M+H$^+$=299.5

1.2: 1'-(3,4-Dihydroquinolin-1(2H)-ylcarbonyl)spiro[indene-1,4'-piperidine]

0.4 g of 4-nitrophenyl 3,4-dihydroquinoline-1(2H)-carboxylate, 0.357 g of 4-spiroindene-piperidine hydrochloride, 0.28 ml of triethylamine and 2 ml of water are introduced into a 10 ml glass tube. The tube is sealed and then heated at 150° C. under microwave irradiation for 50 minutes. Dichloromethane is added. The organic phase is dried over magnesium sulfate and the solvent is evaporated under reduced pressure. The residue is chromatographed on silica gel with a heptane/ethyl acetate gradient from 9/1 to 0/1. 0.393 g of 1'-(3,4-dihydroquinolin-1(2H)-ylcarbonyl)spiro[indene-1,4'-piperidine] is obtained.

Melting point=130-133° C.; M+H$^+$=345.3

$^1$H NMR (CDCl$_3$, 200 MHz), δ (ppm): 1.34 (m, 2H); 1.95-2.15 (m, 2H); 2.8 (t, 2H); 3.15 (dt, 2H); 3.7 (t, 2H); 4.0 (m, 2H); 6.8 (d, 1H); 6.9 (d, 1H); 6.91-7 (m, 1H); 7.1-7.4 (m, 7H).

Example 2

1-(3,4-Dihydroquinolin-1(2H)-ylcarbonyl)-4-phenylpiperidine-4-carbonitrile (Compound No. 17)

2.1: 3,4-Dihydroquinoline-1(2H)-carbamic Acid Chloride 4.9 g of triphosgene are added to a solution of 5.5 g of 1,2,3,4-tetrahydroquinoline and 6.4 ml of triethylamine in 213 ml of dichloromethane at 0° C. The reaction mixture is stirred for 3 h and is then poured onto a mixture of water and ice. A saturated aqueous sodium hydrogencarbonate solution and dichloromethane are added. The aqueous phase is extracted with dichloromethane. The organic phases are combined, washed with water and with a saturated aqueous sodium chloride solution and dried over sodium sulfate and then the solvent is evaporated under reduced pressure to result in 7.8 g of 3,4-dihydroquinoline-1(2H)-carbonyl chloride.

M+H$^+$=196.4

2.2: N,N-bis(2-Chloroethyl)-3,4-dihydroquinoline-1(2H)-carboxamide

A solution of 7 g of 3,4-dihydroquinoline-1(2H)-carbamic acid chloride in 180 ml of acetonitrile is introduced into a 500 ml round-bottomed flask. 9.6 g of bis(2-chloroethyl)amine hydrochloride and 14.83 g of potassium carbonate are subsequently added and the reaction mixture is stirred for 18 h. The acetonitrile is evaporated under reduced pressure and water and ethyl acetate are subsequently added. The aqueous phase is extracted with ethyl acetate and then the organic phases are combined, washed with water and dried over sodium sulfate and then the solvent is evaporated under reduced pressure. The residue is chromatographed on silica gel with a dichloromethane/methanol gradient from 1/0 to 95/5. 2.91 g of N,N-bis(2-chloroethyl)-3,4-dihydroquinoline-1(2H)-carboxamide are obtained.

M+H$^+$=301.3; 303.4

2.3: 1-(3,4-Dihydroquinolin-1(2H)-ylcarbonyl)-4-phenylpiperidine-4-carbonitrile 0.29 ml of phenylacetonitrile in 6 ml of tetrahydrofuran is introduced into a 25 ml three-necked flask. 0.38 g of sodium hydride is subsequently added at 0° C. The reaction medium is stirred at ambient temperature for 30 min and then, at 0° C., 0.5 g of N,N-bis(2-chloroethyl)-3,4-dihydroquinoline-1(2H)-carboxamide is added. The reaction mixture is brought to reflux for 3 h and then ice, water and ethyl acetate are added. The aqueous phase is extracted with ethyl acetate and then the organic phases are combined, washed with water and dried over sodium sulfate and then the solvent is evaporated under reduced pressure. The residue is chromatographed on silica gel with a heptane/methanol gradient from 1/0 to 95/5. 2.91 g of 1-(3,4-dihydroquinolin-1(2H)-ylcarbonyl)-4-phenylpiperidine-4-carbonitrile are obtained.

Melting point=53-59° C., M+H$^+$=346.3

$^1$H NMR (CDCl$_3$, 200 MHz), δ (ppm): 1.7-1.92 (m, 6H); 2.6 (t, 2H); 3.05 (dt, 2H); 3.48 (t, 2H); 3.8 (m, 2H); 6.78 (t, 1H); 6.84-7 (m, 3H); 7.11-7.31 (m, 5H).

Example 3

4-[(3-(Pyridin-3-yl)pyrrolidin-1-yl)carbonyl]-3,4-dihydro-2H-1,4-benzoxazine Hydrochloride (Compound No. 26)

3.1: 4-Nitrophenyl 2,3-dihydro-4H-1,4-benzoxazine-4-carboxylate 1 g of 3,4-dihydro-2H-1,4-benzoxazine, 1.03 ml of triethylamine, 27 ml of tetrahydrofuran and then 1.5 g of paranitrophenyl chloroformate are introduced into a 100 ml round-bottomed flask. The reaction mixture is stirred at ambient temperature for three hours and then filtered. The solvent is evaporated under reduced pressure and the residue is taken up in dichloromethane and washed with a 2N aqueous hydrochloric acid solution and then twice with water. The organic phase is dried over magnesium sulfate and the solvent is evaporated under reduced pressure to result in 2.1 g of 4-nitrophenyl 2,3-dihydro-4H-1,4-benzoxazine-4-carboxylate.
M+H$^+$=301

3.2: 4-[(3-(Pyridin-3-yl)pyrrolidin-1-yl)carbonyl]-3,4-dihydro-2H-1,4-benzoxazine 0.2 g of 4-nitrophenyl 2,3-dihydro-4H-1,4-benzoxazine-4-carboxylate, 0.1 g of 3-(pyrrolidin-3-yl)pyridine and 1.5 ml of water are introduced into a 10 ml glass tube. The tube is sealed and then heated at 100° C. under microwave irradiation for 35 minutes. Dichloromethane is added. The organic phase is dried over magnesium sulfate and the solvent is evaporated under reduced pressure. The residue is chromatographed on silica gel with a dichloromethane/methanol gradient from 1/0 to 95/5. 0.19 g of 4-[(3-(pyridin-3-yl)pyrrolidin-1-yl)carbonyl]-3,4-dihydro-2H-1,4-benzoxazine is obtained.
M+H$^+$=310

3.3: 4-[(3-(Pyridin-3-yl)pyrrolidin-1-yl)carbonyl]-3,4-dihydro-2H-1,4-benzoxazine Hydrochloride 5.82 ml of a 0.2N solution of hydrochloric acid in ether are added to a 25 ml round-bottomed flask comprising 0.18 g of 4-[(3-(pyridin-3-yl)pyrrolidin-1-yl)carbonyl]-3,4-dihydro-2H-1,4-benzoxazine. Stirring is maintained for 10 min. After evaporating, the residue is taken up in ether. The precipitate is filtered off and then dried under vacuum. 0.12 g of 4-[(3-(pyridin-3-yl)pyrrolidin-1-yl)carbonyl]-3,4-dihydro-2H-1,4-benzoxazine hydrochloride is obtained.

Melting point=60-90° C., M+H$^+$=310.4
$^1$H NMR (d$_6$-DMSO, 200 MHz), δ (ppm): 1.9-2.18 (m, 1H); 2.2-2.4 (m, 1H); 3.3-3.9 (m, 7H); 4.08-4.4 (m, 2H); 6.7-6.9 (m, 3H); 7-7.12 (m, 1H); 7.9 (dd, 1H); 8.4 (d, 1H); 8.7 (d, 1H); 8.8 (d, 1H).

Example 4

1-({4-[3-(2,6-Dichlorophenyl)-1,2,4-oxadiazol-5-yl]piperidin-1-yl}carbonyl)-1,2,3,4-tetrahydroquinoline (Compound No. 25)

4.1: 1(1H-Imidazol-1-ylcarbonyl)-1,2,3,4-tetrahydroquinoline 15.4 g of 1,1'-carbonyldiimidazole, 125 ml of tetrahydrofuran and 9.43 ml of 1,2,3,4-tetrahydroquinoline are introduced into a 500 ml round-bottomed flask. The reaction medium is brought to reflux for 20 hours. The solvent is evaporated under reduced pressure and the residue is taken up in ethyl acetate and then washed with water. The organic phase is dried over sodium sulfate and the solvent is evaporated under reduced pressure to result in 16.04 g of 1-(1H-imidazol-1-ylcarbonyl)-1,2,3,4-tetrahydroquinoline.
M+H$^+$=228

4.2: 1-(3,4-Dihydroquinolin-1(2H)-ylcarbonyl)-3-methyl-1H-imidazol-3-ium Iodide 13.3 g of 1-(1H-imidazol-1-ylcarbonyl)-1,2,3,4-tetrahydroquinoline, 133 ml of acetonitrile and 14.6 ml of iodomethane are introduced into a 500 ml round-bottomed flask. The reaction mixture is stirred for 20 h and then the solvent is evaporated under reduced pressure to result in 23 g of 1-(3,4-dihydroquinolin-1(2H)-ylcarbonyl)-3-methyl-1H-imidazol-3-ium iodide.
M+H$^+$=242

4.3: Ethyl 1-(3,4-dihydroquinolin-1(2H)-ylcarbonyl)piperidine-4-carboxylate 16.5 g of 1-(3,4-dihydroquinolin-1(2H)-ylcarbonyl)-3-methyl-1H-imidazol-3-ium iodide, 224 ml of dichloromethane and 8.45 g of ethyl isonipecotate, followed by 31.22 ml of triethylamine, are introduced into a 500 ml round-bottomed flask. The reaction medium is stirred at ambient temperature for 20 hours. The solvent is evaporated under reduced pressure and the residue is taken up in ethyl acetate and then washed with water. The organic phase is dried over sodium sulfate and the solvent is evaporated under reduced pressure to result in 15.2 g of ethyl 1-(3,4-dihydroquinolin-1(2H)-ylcarbonyl)piperidine-4-carboxylate.
M+H$^+$=317

4.4: 1-(3,4-Dihydroquinolin-1(2H)-ylcarbonyl)piperidine-4-carboxylic Acid 11.2 g of ethyl 1-(3,4-dihydroquinolin-1(2H)-ylcarbonyl)piperidine-4-carboxylate, 443 ml of ethanol and 163 ml of 1N aqueous sodium hydroxide solution are introduced into a 1 l round-bottomed flask. The reaction medium is heated at 50° C. for 4 h 30. The ethanol is evaporated under reduced pressure and a 1N aqueous hydrochloric acid solution is subsequently added. The precipitate is filtered off, washed with water and then dried under reduced pressure. 9.5 g of 1-(3,4-dihydroquinolin-1(2H)-ylcarbonyl)piperidine-4-carboxylic acid are obtained.
M+H$^+$=289

4.5: 1-({4-[3-(2,6-Dichlorophenyl)-1,2,4-oxadiazol-5-yl]piperidin-1-yl}carbonyl)-1,2,3,4-tetrahydroquinoline 0.3 g of 1-(3,4-dihydroquinolin-1(2H)-ylcarbonyl)piperidine-4-carboxylic acid, 11 ml of dimethylformamide, 0.67 g of O-benzotriazol-1-yl-N,N,N',N'-tetramethyluronium tetrafluoroborate, 0.028 g of 1-hydroxybenzotriazole, 0.91 ml of diisopropylethylamine and then 0.32 g of 2,6-dichloro-N'-hydroxybenzenecarboximidamide are introduced into a 100 ml round-bottomed flask. The reaction medium is stirred at ambient temperature for 1 h 30 and then heated at 95° C. for 20 hours. Water is added and the mixture is extracted with ethyl acetate. The organic phase is washed three times with water and dried over sodium sulfate and the solvent is evaporated under reduced pressure. The residue is chromatographed on silica gel with a heptane/ethyl acetate gradient from 0/1 to 1/1. 0.18 g of 1-({4-[3-(2,6-dichlorophenyl)-1,2,4-oxadiazol-5-yl]piperidin-1-yl}carbonyl)-1,2,3,4-tetrahydroquinoline is obtained.

Melting point=63-68° C., M+H$^+$=457
$^1$H NMR (d$_6$-DMSO, 200 MHz), δ (ppm): 1.6-1.92 (m, 4H); 1.98-2.14 (m, 2H); 2.72 (t, 2H); 3.1 (dt, 2H); 3.32-3.56 (m, 3H); 3.7 (dt, 2H); 6.75-7.1 (m, 4H); 7.58-7.3 (m, 3H).

Example 5

1-[(4-(Pyridin-4-yl)piperidin-1-yl)carbonyl]-1,2,3,4-tetrahydroquinoline Hydrochloride (Compound No. 4)

5.1: tert-Butyl 4-{[(trifluoromethyl)sulfonyl]oxy}-3,6-dihydropyridine-1(2H)-carboxylate 5.52 ml of a 2.5N solution of n-butyllithium in hexane are added dropwise, in a 250 ml three-necked flask under nitrogen, to a solution of 2.11 ml of diisopropylamine in 20 ml of tetrahydrofuran cooled to −78° C. After stirring for ½ hour, 2.5 g of 1(N)-boc-4-piperidone in tetrahydrofuran (10 ml) are added at 0° C. Finally, still at 0° C., 4.71 g of N-phenyltrifluoromethanesulfonimide are added. After stirring at ambient temperature for 2 hours, the tetrahydrofuran is evaporated and the product is purified by rapid filtration through alumina using a heptane/ethyl acetate 9/1 mixture as eluent. 3.35 g of tert-butyl 4-{[(trifluoromethyl)sulfonyl]oxy}-3,6-dihydropyridine-1(2H)-carboxylate are obtained.

$^1$H NMR (CDCl$_3$, 200 MHz), δ (ppm): 1.44 (s, 9H); 2.41 (m, 2H); 3.6 (t, 2H, J=5.7 Hz); 4.0 (m, 2H); 5.74 (s, 1H).

5.2: tert-Butyl 3,6-dihydro-4,4'-bipyridine-1(2H)-carboxylate 1 g of tert-butyl 4-{[(trifluoromethyl)sulfonyl]oxy}-3,6-dihydropyridine-1(2H)-carboxylate, 0.256 g of lithium chloride, 1.418 g of potassium carbonate, 1.05 g of 4-(4,4,5,5-tetramethyl-1,3,2-dioxaborolan-2-yl)pyridine and 0.209 g of tetrakis(triphenylphosphine)palladium are introduced into 15 ml of 1,2-dimethoxyethane in a 100 ml three-necked flask under nitrogen; the mixture is brought to reflux for 1 h 30. The mixture is allowed to return to ambient temperature, 100 ml of water are added and the aqueous phase is extracted with 3 times 80 ml of ethyl acetate. The organic phases are combined and dried over sodium sulfate and the solvent is evaporated under reduced pressure. The residue is chromatographed on silica gel with a dichloromethane to dichloromethane/methanol/aqueous ammonia 90/10/1 elution gradient. 0.821 g of tert-butyl 3,6-dihydro-4,4'-bipyridine-1(2H)-carboxylate is obtained.

$^1$H NMR (CDCl$_3$, 200 MHz), δ (ppm): 1.44 (s, 9H); 2.4 (m, 2H); 3.6 (t, 2H, J=5.7 Hz); 4.0 (m, 2H); 5.95 (bs, 1H); 8.45 (m, 1H); 7.4-7.7 (m, 3H).

5.3: tert-Butyl 4-(pyridin-4-yl)piperidine-1-carboxylate 0.336 g of 5% Pd/C is added to 0.821 g of tert-butyl 3,6-dihydro-4,4'-bipyridine-1(2H)-carboxylate, dissolved in 65 ml of methanol, in a high-pressure reactor under nitrogen. The reaction mixture is placed under a pressure of 3 atmospheres of hydrogen at 25° C. and stirred mechanically for 1 h. The palladium is filtered off on Whatman paper (registered trademark) and is washed with methanol. The solvent is evaporated and the residue is then chromatographed on silica gel, heptane/ethyl acetate (8/2) to heptane/ethyl acetate (1/1) elution gradient. 0.552 g of tert-butyl 4-(pyridin-4-yl)piperidine-1-carboxylate is obtained.

M+H$^+$=263

5.4: 4-(Piperidin-4-yl)pyridine 1.54 ml of a 4N solution of hydrochloric acid in dioxane are added dropwise using a dropping funnel to a 25 ml round-bottomed flask comprising 0.552 g of tert-butyl 4-(pyridin-4-yl)piperidine-1-carboxylate. Stirring is maintained for 1 hour. The product is subsequently concentrated under vacuum and then treated with a 1N aqueous sodium hydroxide solution. The aqueous phase is extracted 3 times with dichloromethane. The organic phase is dried over sodium sulfate and concentrated under reduced pressure. 0.341 g of 4-(piperidin-4-yl)pyridine is obtained.

$^1$H NMR (CDCl$_3$, 200 MHz), δ (ppm): 1.9-2.2 (m, 8H); 3 (m, 1H); 3.3 (m, 1H); 7.1 (d, 2H), 8.45 (d, 2H).

5.5: 1-[(4-(Pyridin-4-yl)piperidin-1-yl)carbonyl]-1,2,3,4-tetrahydroquinoline 0.12 g of 1,2,3,4-tetrahydroquinoline, 9 ml of dichloromethane and 0.16 ml of triethylamine are placed in a 50 ml round-bottomed flask under nitrogen atmosphere. 0.09 g of triphosgene is added at 0° C. and then the reaction mixture is left stirring at ambient temperature for 18 h. 0.147 g of 4-(piperidin-4-yl)pyridine is subsequently added and the reaction mixture is stirred for 60 h and then refluxed for 12 h. 20 ml of a saturated aqueous sodium hydrogencarbonate solution are added and then the aqueous phase is extracted three times with dichloromethane. The organic phases are combined and dried over sodium sulfate and the solvent is evaporated under reduced pressure. The residue is chromatographed on silica gel with a dichloromethane/methanol 95/5 mixture. 0.11 g of 1-[(4-(pyridin-4-yl)piperidin-1-yl)carbonyl]-1,2,3,4-tetrahydroquinoline is obtained.

M+H$^+$=322.2

5.6: 1-[(4-(Pyridin-4-yl)piperidin-1-yl)carbonyl]-1,2,3,4-tetrahydroquinoline Hydrochloride 0.11 g of 1-[(4-(pyridin-4-yl)piperidin-1-yl)carbonyl]-1,2,3,4-tetrahydroquinoline, dissolved in 3 ml of dichloromethane, is introduced into a 25 ml round-bottomed flask. 3.5 ml of a 0.2N solution of hydrochloric acid in ether are subsequently added. Stirring is maintained for 10 min. After evaporating, the residue is taken up in ethyl acetate. The precipitate is filtered off then dried under vacuum. 0.09 g of 1-[(4-(pyridin-4-yl)piperidin-1-yl)carbonyl]-1,2,3,4-tetrahydroquinoline hydrochloride is obtained.

Melting point=198° C., M+H$^+$=322.2

$^1$H NMR (d$_6$-DMSO, 200 MHz), δ (ppm): 1.5-2 (m, 6H); 2.6-3.2 (m, 5H); 3.5 (t, 2H); 3.8-4 (m, 2H); 6.75-7.2 (m, 4H); 7.9 (d, 2H); 8.8 (d, 2H).

Example 6

1-Butyl-4-[(3-(pyridin-3-yl)pyrrolidin-1-yl)carbonyl]-1,2,3,4-tetrahydroquinoxaline Hydrochloride (Compound No. 119)

6.1: tert-Butyl 4-[(3-(pyridin-3-yl)pyrrolidin-1-yl)carbonyl]-3,4-dihydroquinoxaline-1(2H)-carboxylate 2.75 g of the tert-butyl ester of 3,4-dihydro-1(2H)-quinoxalinecarbamic acid, 117 ml of dichloromethane and 5.8 ml of diisopropylethylamine are placed in a 500 ml round-bottomed flask under a nitrogen atmosphere. 1.74 g of triphosgene are added at 0° C. and then the reaction mixture is left stirring at ambient temperature for three hours. 2 ml of diisopropylethylamine and 1.83 g of 3-(pyrrolidin-3-yl)pyridine are subsequently added and the reaction mixture is stirred for eighteen hours. 200 ml of a saturated aqueous sodium hydrogencarbonate solution are added and then the aqueous phase is extracted three times with dichloromethane. The organic phases are combined and dried over sodium sulfate and the solvent is evaporated under reduced pressure. The residue is chromatographed on silica gel with a dichloromethane/methanol 95/5 mixture. 3.72 g of tert-butyl 4-[(3-(pyridin-3-yl)pyrrolidin-1-yl)carbonyl]-3,4-dihydroquinoxaline-1(2H)-carboxylate are obtained.

M+H$^+$=409.3

6.2: 1-[(3-(Pyridin-3-yl)pyrrolidin-1-yl)carbonyl]-1,2,3,4-tetrahydroquinoxaline 3.72 g of tert-butyl 4-[(3-(pyridin-3-yl)pyrrolidin-1-yl)carbonyl]-3,4-dihydroquinoxaline-1(2H)-carboxylate, dissolved in 18.2 ml of dioxane, are introduced into a 250 ml round-bottomed flask. 34.1 ml of a 4N solution of hydrochloric acid in dioxane are subsequently added. Stirring is maintained for three hours. After evaporating, the residue is taken up in dichloromethane and a saturated aqueous sodium hydrogencarbonate solution and then the aqueous phase is extracted three times with dichloromethane. The organic phases are combined and dried over sodium sulfate and the solvent is evaporated under reduced pressure. 2.6 g of 1-[(3-(pyridin-3-yl)pyrrolidin-1-yl)carbonyl]-1,2,3,4-tetrahydroquinoxaline are obtained.

M+H$^+$=309.3

6.3: 1-Butyl-4-[(3-(pyridin-3-yl)pyrrolidin-1-yl)carbonyl]-1,2,3,4-tetrahydroquinoxaline 0.2 g of 1-[(3-(pyridin-3-yl)pyrrolidin-1-yl)carbonyl]-1,2,3,4-tetrahydroquinoxaline, dissolved in 22 ml of dichloromethane, is introduced into a 100 ml round-bottomed flask. 0.29 ml of N-butyraldehyde is subsequently added, followed by 0.27 g of sodium triacetoxyborohydride, and the reaction mixture is stirred for eighteen hours. A saturated aqueous sodium hydrogencarbonate solution is added and then the aqueous phase is extracted three times with dichloromethane. The organic phases are combined and dried over sodium sulfate and the solvent is evaporated under reduced pressure. The residue is chromatographed on silica gel with a dichloromethane/methanol 95/5 mixture. 0.032 g of 1-butyl-4-[(3-(pyridin-3-yl)pyrrolidin-1-yl)carbonyl]-1,2,3,4-tetrahydroquinoxaline is obtained.

M+H$^+$=365.3

6.4: 1-Butyl-4-[(3-(pyridin-3-yl)pyrrolidin-1-yl)carbonyl]-1,2,3,4-tetrahydroquinoxaline Hydrochloride 0.032 g of 1-butyl-4-[(3-(pyridin-3-yl)pyrrolidin-1-yl)carbonyl]-1,2,3,4-tetrahydroquinoxaline, dissolved in 0.9 ml of dichloromethane, is introduced into a 10 ml round-bottomed flask. 0.45 ml of a 0.2N solution of hydrochloric acid in ether is subsequently added. Stirring is maintained for ten minutes. After evaporating, 0.030 g of 1-butyl-4-[(3-(pyridin-3-yl)pyrrolidin-1-yl)carbonyl]-1,2,3,4-tetrahydroquinoxaline hydrochloride is obtained.

Melting point=191° C., M+H$^+$=365.3

$^1$H NMR (d$_6$-DMSO, 200 MHz), δ (ppm): 0.86 (t, 3H); 1.17-1.39 (m, 1H); 1.39-1.6 (m, 1H); 1.9-2.35 (m, 1H); 3.1-3.9 (m, 14H); 6.43-6.54 (m, 1H); 6.6-6.69 (m, 1H); 6.75-6.88 (m, 1H); 7.97 (dd, 1H); 8.45 (dd, 1H); 8.77 (dd, 1H); 8.82 (dd, 1H).

Example 7

N,N-Dimethyl-4-[(3-(pyridin-3-yl)pyrrolidin-1-yl)carbonyl]-3,4-dihydroquinoxaline-1(2H)-carboxamide Hydrochloride (Compound No. 110)

7.1: N,N-Dimethyl-4-[(3-(pyridin-3-yl)pyrrolidin-1-yl)carbonyl]-3,4-dihydroquinoxaline-1(2H)-carboxamide 0.25 g of 1-[(3-(pyridin-3-yl)pyrrolidin-1-yl)carbonyl]-1,2,3,4-tetrahydroquinoxaline, 8.1 ml of dichloromethane and 0.5 ml of diisopropylethylamine are placed in a 50 ml round-bottomed flask under a nitrogen atmosphere. 0.12 g of triphosgene is added at 0° C. and then the reaction mixture is left stirring at ambient temperature for one and a half hours. 0.5 ml of diisopropylethylamine and 2.03 ml of a 2N solution of dimethylamine in tetrahydrofuran are subsequently added and the reaction mixture is stirred for eighteen hours. Water is added and then the aqueous phase is extracted three times with dichloromethane. The organic phases are combined and dried over sodium sulfate and the solvent is evaporated under reduced pressure. The residue is chromatographed on silica gel with a dichloromethane/methanol 90/10 mixture. 0.22 g of N,N-dimethyl-4-[(3-(pyridin-3-yl)pyrrolidin-1-yl)carbonyl]-3,4-dihydroquinoxaline-1(2H)-carboxamide is obtained.

M+H$^+$=380.3

7.2: N,N-Dimethyl-4-[(3-(pyridin-3-yl)pyrrolidin-1-yl)carbonyl]-3,4-dihydroquinoxaline-1(2H)-carboxamide Hydrochloride 0.157 g of N,N-dimethyl-4-[(3-(pyridin-3-yl)pyrrolidin-1-yl)carbonyl]-3,4-dihydroquinoxaline-1(2H)-carboxamide, dissolved in 8.1 ml of dichloromethane, is introduced into a 10 ml round-bottomed flask. 4.08 ml of a 0.1N solution of hydrochloric acid in ether are subsequently added. Stirring is maintained for ten minutes. After evaporating, 0.156 g of N,N-dimethyl-4-[(3-(pyridin-3-yl)pyrrolidin-1-yl)carbonyl]-3,4-dihydroquinoxaline-1(2H)-carboxamide hydrochloride is obtained.

Melting point=181° C., M+H$^+$=380.3

$^1$H NMR (d$_6$-DMSO, 200 MHz), δ (ppm): 1.87-2.15 (m, 1H); 2.15-2.33 (m, 1H); 2.75 (s, 6H); 3.2-3.9 (m, 9H); 6.8-6.98 (m, 3H); 7-7.1 (m, 1H); 7.85 (dd, 1H); 8.35 (dd, 1H); 8.7 (dd, 1H); 8.75 (dd, 1H).

Example 8

Methyl 4-[(3-(pyridin-3-yl)pyrrolidin-1-yl)carbonyl]-3,4-dihydroquinoxaline-1(2H)-carboxylate (Compound No. 118)

0.25 g of 1-[(3-(pyridin-3-yl)pyrrolidin-1-yl)carbonyl]-1,2,3,4-tetrahydroquinoxaline, 8.1 ml of dichloromethane and 0.3 ml of diisopropylethylamine are placed in a 50 ml round-bottomed flask under a nitrogen atmosphere. 0.12 g of triphosgene is added at 0° C. and then the reaction mixture is left stirring at ambient temperature for three hours. 0.5 ml of diisopropylethylamine and 0.33 ml of methanol are subsequently added and the reaction mixture is stirred for twenty-four hours. A saturated aqueous sodium hydrogencarbonate solution and dichloromethane are added. The aqueous phase is extracted three times with dichloromethane. The organic phases are combined, washed with water and with a saturated aqueous sodium chloride solution and dried over sodium sulfate and then the solvent is evaporated under reduced pressure. The residue is chromatographed on silica gel with a dichloromethane/methanol 95/5 mixture. 0.112 g of methyl 4-[(3-(pyridin-3-yl)pyrrolidin-1-yl)carbonyl]-3,4-dihydroquinoxaline-1(2H)-carboxylate is obtained.

Melting point=83° C.

$^1$H NMR (d$_6$-DMSO, 200 MHz), δ (ppm): 1.8-2.1 (m, 1H); 2.1-2.3 (m, 1H); 3.1-3.5 (m, 5H); 3.6-3.9 (m, 4H); 3.7 (s, 3H); 6.85-7.1 (m, 2H); 7.35 (dd, 1H); 7.63-7.8 (m, 1H); 8.38-8.54 (m, 3H).

Example 9

1-Acetyl-4-[(3-(pyridin-3-yl)pyrrolidin-1-yl)carbonyl]-1,2,3,4-tetrahydroquinoxaline Hydrochloride (Compound No. 120)

9.1: 1-Acetyl-4-[(3-(pyridin-3-yl)pyrrolidin-1-yl)carbonyl]-1,2,3,4-tetrahydroquinoxaline 0.25 g of 1-[(3-(pyridin-3-yl)pyrrolidin-1-yl)carbonyl]-1,2,3,4-tetrahydroquinoxaline and 1.05 ml of acetic anhydride are placed in a 10 ml round-bottomed flask. The reaction medium is brought to reflux for two hours and then a solution of ammonia in water is added at 0° C. The aqueous phase is extracted three times with ethyl acetate. The organic phases are combined and dried over sodium sulfate and the solvent is evaporated under reduced pressure. The residue is chromatographed on silica gel with a dichloromethane/methanol 95/5 mixture. 0.284 g of 1-acetyl-4-[(3-(pyridin-3-yl)pyrrolidin-1-yl)carbonyl]-1,2,3,4-tetrahydroquinoxaline is obtained.

M+H$^+$=351.3

9.2: 1-Acetyl-4-[(3-(pyridin-3-yl)pyrrolidin-1-yl)carbonyl]-1,2,3,4-tetrahydroquinoxaline Hydrochloride 0.284 g of 1-acetyl-4-[(3-(pyridin-3-yl)pyrrolidin-1-yl)carbonyl]-1,2,3,4-tetrahydroquinoxaline, dissolved in 4.05 ml of a 0.2N solution of hydrochloric acid in ether, is introduced into a 25 ml round-bottomed flask. Stirring is maintained for ten minutes. After evaporating, 0.126 g of 1-acetyl-4-[(3-(pyridin-3-yl)pyrrolidin-1-yl)carbonyl]-1,2,3,4-tetrahydroquinoxaline hydrochloride is obtained.

Melting point=201° C., M+H$^+$=351.3

$^1$H NMR (d$_6$-DMSO, 200 MHz), δ (ppm): 1.9-3.9 (m, 2H); 2.14 (s, 3H); 3-4.1 (m, 9H); 6.9-7.2 (m, 4H); 7.93 (dd, 1H); 8.3 (dd, 1H); 8.7 (dd, 1H); 8.75 (dd, 1H).

Example 10

{4-[(3-(Pyridin-3-yl)pyrrolidin-1-yl)carbonyl]-3,4-dihydro-2H-1,4-benzoxazin-6-yl}methanol Hydrochloride (Compound No. 82)

10.1: Methyl 3-amino-4-hydroxybenzoate 100 ml of methanol are introduced into a 500 ml three-necked flask and then, at 0° C., 9.75 ml of acetyl chloride are added dropwise. 5 g of 3-amino-4-hydroxybenzoic acid are subsequently added at 0° C. and then the reaction medium is stirred at ambient temperature for eighteen hours. A saturated solution of sodium hydrogencarbonate in water is subsequently added at 0° C. and the mixture is extracted three times with ethyl acetate. The organic phases are combined and then dried over magnesium sulfate and the solvent is evaporated under reduced pressure to result in 5.16 g of methyl 3-amino-4-hydroxybenzoate.

M+H$^+$=168.2

10.2: Methyl 3,4-dihydro-2H-1,4-benzoxazine-6-carboxylate 5.16 g of methyl 3-amino-4-hydroxybenzoate are dissolved in 100 ml of dimethylformamide in a 500 ml round-bottomed flask. 17.06 g of potassium carbonate and then 7.98 ml of dibromoethane are subsequently added. The reaction medium is heated at 110° C. with stirring for five hours. After evaporating the solvent, water and ethyl acetate are added. The aqueous phase is extracted three times with ethyl acetate. The organic phases are combined and then dried over magnesium sulfate and the solvent is evaporated under reduced pressure. The residue is chromatographed on silica gel with a heptane/ethyl acetate 6/4 mixture. 3.61 g of methyl 3,4-dihydro-2H-1,4-benzoxazine-6-carboxylate are obtained.

M+H$^+$=194.3

10.3: Methyl 4-[(3-(pyridin-3-yl)pyrrolidin-1-yl)carbonyl]-3,4-dihydro-2H-1,4-benzoxazine-6-carboxylate 1.8 g of methyl 3,4-dihydro-2H-1,4-benzoxazine-6-carboxylate, 93.2 ml of dichloromethane and 4.62 ml of diisopropylethylamine are placed in a 250 ml round-bottomed flask under a nitrogen atmosphere. 1.38 g of triphosgene are added at 0° C. and then the reaction mixture is left stirring at ambient temperature for three hours. 1.62 ml of diisopropylethylamine and 1.45 g of 3-(pyrrolidin-3-yl)pyridine are subsequently added and the reaction mixture is stirred for eighteen hours. A saturated aqueous sodium hydrogencarbonate solution and dichloromethane are added. The aqueous phase is extracted three times with dichloromethane. The organic phases are combined, washed with water and with a saturated aqueous sodium chloride solution and dried over sodium sulfate and then the solvent is evaporated under reduced pressure. The residue is chroratographed on silica gel with a dichloromethane/methanol 95/5 mixture. 2.39 g of methyl 4-[(3-(pyridin-3-yl)pyrrolidin-1-yl)carbonyl]-3,4-dihydro-2H-1,4-benzoxazine-6-carboxylate are obtained.

Melting point=61° C., M+H$^+$=368.3

10.4: {4-[(3-(Pyridin-3-yl)pyrrolidin-1-yl)carbonyl]-3,4-dihydro-2H-1,4-benzoxazin-6-yl}methanol 0.4 g of methyl 4-[(3-(pyridin-3-yl)pyrrolidin-1-yl)carbonyl]-3,4-dihydro-2H-1,4-benzoxazine-6-carboxylate and 10 ml of dichloromethane are placed in a 100 ml round-bottomed flask under a nitrogen atmosphere. The temperature of the reaction medium is lowered to −78° C. and then 5.44 ml of a molar solution of diisopropylaluminum hydride in hexane are added. The reaction mixture is left stirring at −78° C. for eighteen hours. The reaction mixture is hydrolyzed with methanol, then an aqueous sodium hydroxide solution and subsequently with a saturated aqueous sodium hydrogencarbonate solution. The aqueous phase is extracted three times with dichloromethane. The organic phases are combined, washed with water and with a saturated aqueous sodium chloride solution and dried over sodium sulfate and then the solvent is evaporated under reduced pressure. The residue is chromatographed on silica gel with a dichloromethane/methanol 90/10 mixture. 0.21 g of {4-[(3-(pyridin-3-yl)pyrrolidin-1-yl)carbonyl]-3,4-dihydro-2H-1,4-benzoxazin-6-yl}methanol is obtained.

M+H$^+$=340.3

10.5: {4-[(3-(Pyridin-3-yl)pyrrolidin-1-yl)carbonyl]-3,4-dihydro-2H-1,4-benzoxazin-6-yl}methanol Hydrochloride 0.21 g of {4-[(3-(pyridin-3-yl)pyrrolidin-1-yl)carbonyl]-3,4-dihydro-2H-1,4-benzoxazin-6-yl}methanol, dissolved in 6.19 ml of a 0.1N solution of hydrochloric acid in ether, is introduced into a 50 ml round-bottomed flask. Stirring is maintained for ten minutes. After evaporating, the residue is triturated in ethyl ether and then the solid is filtered off in order to obtain, after drying under vacuum, 0.108 g of {4-[(3-(pyridin-3-yl)pyrrolidin-1-yl)carbonyl]-3,4-dihydro-2H-1,4-benzoxazin-6-yl}methanol hydrochloride.

Melting point=273° C., M+H$^+$=351.3

$^1$H NMR (d$_6$-DMSO, 200 MHz), δ (ppm): 1.9-2.2 (m, 1H); 2.2-2.45 (m, 1H); 3.3-4.4 (m, 9H); 4.32 (s, 3H); 6.68-6.88 (m, 2H); 7.01 (s, 1H); 7.83 (dd, 1H); 8.32 (dd, 1H); 8.7 (dd, 1H); 8.79 (dd, 1H).

Example 11

Sodium salt of 1-[(3-(pyridin-3-yl)pyrrolidin-1-yl)carbonyl]-1,2,3,4-tetrahydroquinoline-6-carboxylic Acid (Compound No. 79)

11.1: Methyl 1,2,3,4-tetrahydroquinoline-6-carboxylate Hydrochloride 0.93 g of 1,2,3,4-tetrahydroquinoline-6-carboxylic acid and 100 ml of methanol are placed in a 500 ml round-bottomed flask under a nitrogen atmosphere. 0.46 ml of thionyl chloride is added at 0° C. and then the reaction mixture is stirred at reflux for three hours. After evaporating the solvent, the residue is triturated in ethyl ether and then the solid obtained is filtered off and dried under vacuum. 1.13 g of methyl 1,2,3,4-tetrahydroquinoline-6-carboxylate hydrochloride are obtained.

M+H$^+$=192.3

11.2: Methyl 1-[(3-(pyridin-3-yl)pyrrolidin-1-yl)carbonyl]-1,2,3,4-tetrahydroquinoline-6-carboxylate 0.6 g of methyl 1,2,3,4-tetrahydroquinoline-6-carboxylate hydrochloride, 13.2 ml of dichloromethane and 2.54 ml of diisopropylethylamine are placed in a 100 ml round-bottomed flask under a nitrogen atmosphere. 0.31 g of triphosgene is added at 0° C. and then the reaction mixture is left stirring at ambient temperature for three hours. 0.39 g of 3-(pyrrolidin-3-yl)pyridine is subsequently added and the reaction mixture is stirred for eighteen hours. Water and dichloromethane are added. The aqueous phase is extracted three times with dichloromethane. The organic phases are combined, washed with water and with a saturated aqueous sodium sulfate solution and dried over sodium sulfate and then the solvent is evaporated under reduced pressure. The residue is chromatographed on silica gel with a dichloromethane/methanol 95/5 mixture. 0.675 g of methyl 1-[(3-(pyridin-3-yl)pyrrolidin-1-yl)carbonyl]-1,2,3,4-tetrahydroquinoline-6-carboxylate is obtained.

M+H$^+$=366.4

11.3: Sodium salt of 1-[(3-(pyridin-3-yl)pyrrolidin-1-yl)carbonyl]-1,2,3,4-tetrahydroquinoline-6-carboxylic Acid 0.2 g of methyl 1-[(3-(pyridin-3-yl)pyrrolidin-1-yl)carbonyl]-1,2,3,4-tetrahydroquinoline-6-carboxylate and 5.5 ml of a tetrahydrofuran/methanol/water (v/v/v=1/1/1) mixture are placed in a 50 ml round-bottomed flask. 0.046 g of lithium hydroxide is added and then the reaction mixture is left stirring at ambient temperature for eighteen hours and heated at 40° C. for two hours. The reaction mixture is subsequently poured onto 8 g of Dowex 50WX8 resin and the heterogeneous mixture is stirred until the product has disappeared from the liquid phase (monitoring by TLC). The resin is filtered off and then washed successively with water, tetrahydrofuran and acetonitrile. The compound is detached using a 2N solution of ammonia in methanol and the solvent is evaporated under reduced pressure. The residue is taken up in methanol and 0.95 ml of a 0.5M solution of sodium methoxide in methanol is added. The solvent is evaporated under reduced pressure and 0.176 g of sodium salt of 1-[(3-(pyridin-3-yl)pyrrolidin-1-yl)carbonyl]-1,2,3,4-tetrahydroquinoline-6-carboxylic acid is obtained.

Melting point=197-202° C., M+H$^+$=352.3

$^1$H NMR (CDCl$_3$, 200 MHz), δ (ppm): 1.5-2 (m, 1H); 2.1-2.4 (m, 3H); 3.1-3.7 (m, 5H); 6.5-6.67 (m, 1H); 7-7.18 (m, 1H); 7.5-7.72 (m, 2H); 8.23-8.4 (dd, 1H).

Example 12

[4-(4-(Methanesulfonyl)benzyl)-3,4-dihydro-2H-quinoxalin-1-yl][3-(1H-pyrazol-4-yl)pyrrolidin-1-yl]methanone (Compound No. 161)

0.3 g of 4-(4-(methanesulfonyl)benzyl)-3,4-dihydro-2H-quinoxaline is dissolved in 10 ml of dichloromethane and 0.1 ml of N-methylmorpholine. 0.118 g of triphosgene is added at 0° C. and then the reaction mixture is left stirring at ambient temperature for four hours. 0.208 g of 4-(pyrrolidin-3-yl)-1H-pyrazole dihydrochloride is subsequently added and the reaction mixture is stirred for eighteen hours. A saturated solution of sodium hydrogencarbonate in water and dichloromethane are added. The aqueous phase is extracted twice with dichloromethane. The organic phases are combined, washed with water and with a saturated aqueous sodium chloride solution and dried over magnesium sulfate and then the solvent is evaporated under reduced pressure. The residue is chromatographed on silica gel, a first time with a gradient of dichloromethane/methanol 1/0 to 85/5 mixture and then a second time with a gradient of dichloromethane/ethyl acetate/methanol 1/0/0 to 70/25/5 mixture. 0.064 g of [4-(4-(methanesulfonyl)benzyl)-3,4-dihydro-2H-quinoxalin-1-yl][3-(1H-pyrazol-4-yl)pyrrolidin-1-yl]methanone is obtained.

Melting point=239° C., M+H$^+$=466.3

$^1$H NMR (CDCl$_3$, 200 MHz), δ (ppm): 1.79-1.91 (m, 1H); 2.09-2.21 (m, 1H); 3.11-3.44 (m, 4H); 3.21 (s, 3H); 3.44-3.68 (m, 4H), 3.74-3.85 (m, 1H); 4.68 (s, 2H); 6.48-6.6 (m, 2H); 6.7-6.79 (m, 1H); 6.81-6.89 (m, 1H); 7.32-7.65 (bs, 1H); 7.51 (d, 2H); 7.89 (d, 2H).

Example 13

N-(Piperidin-1-yl)-4-{4-[3-(1H-pyrazol-4-yl)pyrrolidine-1-carbonyl]-3,4-dihydro-2H-quinoxalin-1-yl}benzamide (Example 172)

13.1: tert-Butyl 4-(4-cyanophenyl)-3,4-dihydroquinoxaline-1(2H)-carboxylate 1 g of 3,4-dihydro-2H-quinoxaline-1-carboxylic acid tert-butyl ester, 10 ml of N-methylpyrrolidinone, 0.57 g of 4-fluorobenzonitrile and 0.96 g of potassium tert-butoxide are introduced into a 20 ml glass tube. The reaction medium is stirred for 5 min, water is added and extraction is carried out 3 times with diethyl ether. The organic phases are combined, washed with water and then with a saturated aqueous sodium chloride solution, dried over sodium sulfate and concentrated under reduced pressure. The residue is chromatographed on silica gel eluted with a gradient of ethyl acetate from 3.5% to 35% in heptane. 0.9 g of tert-butyl 4-(4-cyanophenyl)-3,4-dihydroquinoxaline-1(2H)-carboxylate is obtained.

M+H$^+$=336

13.2: 4-(3,4-Dihydroquinoxalin-1(2H)-yl)benzoic Acid 3.2 g of tert-butyl 4-(4-cyanophenyl)-3,4-dihydroquinoxaline-1(2H)-carboxylate and 30 ml of concentrated hydrochloric acid are introduced into a glass tube. The tube is sealed and then heated to 100° C. under microwave irradiation for 2 times 1 hour. After cooling, the precipitate is filtered off, rinsed with water and dried under vacuum at 40° C. 3.0 g of 4-(3,4-dihydroquinoxalin-1(2H)-yl)benzoic acid are obtained. 1N sodium hydroxide solution is added to the filtrate at 4° C. to basic pH and then extraction is carried out with dichloromethane. Citric acid is added to the aqueous phase to pH=3-4 and extraction is carried out 3 times with dichloromethane. The organic phases are combined, dried over sodium sulfate and concentrated under reduced pressure. The residue is chromatographed on silica gel eluted with a gradient of methanol from 1% to 2% in dichloromethane. An additional amount of 0.8 g of 4-(3,4-dihydroquinoxalin-1(2H)-yl)benzoic acid is thus obtained.

M+H$^+$=255

13.3: Methyl 4-(3,4-dihydroquinoxalin-1(2H)-yl)benzoate 3.8 g of 4-(3,4-dihydroquinoxalin-1(2H)-yl)benzoic acid and 70 ml of methanol are introduced into a 250 ml round-bottomed flask equipped with a magnetic stirrer. 4.4 ml of 97% sulfuric acid are added dropwise and the reaction medium is stirred at ambient temperature for 18 h. The methanol is partially evaporated. The remaining solution is poured onto a water-plus-ice mixture, neutralized by slow addition of sodium hydrogencarbonate and extracted 3 times with ethyl acetate. The organic phases are combined, washed with water and with a saturated sodium chloride solution, dried over sodium sulfate and concentrated under reduced pressure. The residue is chromatographed on silica gel eluted with a gradient of ethyl acetate from 10% to 20% in heptane. 2.8 g of methyl 4-(3,4-dihydroquinoxalin-1(2H)-yl)benzoate are obtained.

M+H$^+$=269

13.4: Methyl 4-[4-{[3-(1H-pyrazol-4-yl)pyrrolidin-1-yl]carbonyl}-3,4-dihydroquinoxalin-1(2H)-yl]benzoate 2.7 g of methyl 4-(3,4-dihydroquinoxalin-1(2H)-yl)benzoate and 50 ml of dichloromethane are introduced into a three-necked flask equipped with a magnetic stirrer and placed under an inert atmosphere. After cooling to 4° C., 4.2 ml of triethylamine and 1.19 g of triphosgene are successively added. The reaction medium is stirred at ambient temperature for 4 h. 2.11 g of 4-(pyrrolidin-3-yl)-1H-pyrazole dihydrochloride and 1.4 ml of triethylamine are then introduced and the mixture is stirred at ambient temperature for 18 h. The reaction medium is washed with a saturated aqueous sodium hydrogencarbonate solution; the organic phase is dried over sodium sulfate and concentrated under reduced pressure. The residue is chromatographed on silica gel eluted with a gradient of methanol from 1.5% to 3% in dichloromethane. 4.2 g of methyl 4-[4-{[3-(1H-pyrazol-4-yl)pyrrolidin-1-yl]carbonyl}-3,4-dihydroquinoxalin-1(2H)-yl]benzoate are obtained.

M+H$^+$=432

13.5: 4-[4-{[3-(1H-Pyrazol-4-yl)pyrrolidin-1-yl]carbonyl}-3,4-dihydroquinoxalin-1(2H)-yl]benzoic Acid 4.2 g of methyl 4-[4-{[3-(1H-pyrazol-4-yl)pyrrolidin-1-yl]carbonyl}-3,4-dihydroquinoxalin-1(2H)-yl]benzoate and 50 ml of a tetrahydrofuran/methanol/water 2/1/1 mixture are introduced into a 250 ml round-bottomed flask equipped with a magnetic stirrer and placed in an ice bath. 1.63 g of lithium hydroxide monohydrate are added and the reaction mixture is stirred at ambient temperature for 18 h. After evaporating the organic solvents, citric acid is added up to pH 5. The precipitate is filtered off and dried under vacuum. 3.87 g of 4-[4-{[3-(1H-pyrazol-4-yl)pyrrolidin-1-yl]carbonyl}-3,4-dihydroquinoxalin-1(2H)-yl]benzoic acid are obtained.

M+H$^+$=418

13.6: N-(Piperidin-1-yl)-4-{4-[3-(1H-pyrazol-4-yl)pyrrolidine-1-carbonyl]-3,4-dihydro-2H-quinoxalin-1-yl}benzamide 0.4 g of 4-[4-{[3-(1H-pyrazol-4-yl)pyrrolidin-1-yl]carbonyl}-3,4-dihydroquinoxalin-1(2H)-yl]benzoic acid, 0.19 g of 1-aminopiperidine, 0.26 g of hydroxybenzotriazole, 0.37 g of EDC.HCl and 7 ml of a dioxane/dimethylformamide 5/2 mixture are introduced into a 100 ml round-bottomed flask equipped with a magnetic stirrer. The reaction mixture is stirred at ambient temperature for 20 h and concentrated under vacuum. The residue is chromatographed on silica gel eluted with a dichloromethane/acetone/methanol/NH$_4$OH 88/10/2/0.2 and then 82/15/3/0.3 mixture. After triturating in ethyl ether, 0.28 g of N-(piperidin-1-yl)-4-{4-[3-(1H-pyrazol-4-yl)pyrrolidine-1-carbonyl]-3,4-dihydro-2H-quinoxalin-1-yl}benzamide is obtained.

Melting point=251° C.; M+H$^+$=500

$^1$H NMR (d$_6$-DMSO, 200 MHz), δ (ppm): 1.38 (m, 2H); 1.60 (m, 4H); 1.87 (m, 1H); 2.22 (m, 1H); 2.81 (m, 4H); 3.15-3.5 (m, 4H); 3.5-3.65 (m, 2H); 3.7-3.9 (m, 3H); 6.83 (m, 2H); 7.04 (m, 2H); 7.25 (d, 2H); 7.4 (m, 1H); 7.60 (m, 1H); 7.75 (d, 2H); 9.16 (s, 1H); 12.62 (s, 1H).

Example 14

N-Cyclopropyl-2-methoxy-4-{4-[3-(1H-pyrazol-4-yl)pyrrolidine-1-carbonyl]-3,4-dihydro-2H-quinoxalin-1-yl}benzamide (Example No. 78)

14.1: 4-(3-Methoxy-4-(methoxycarbonyl)phenyl)-3,4-dihydro-2H-quinoxaline-1-carboxylic Acid Tert-Butyl Ester 0.64 g of 3,4-dihydro-2H-quinoxaline-1-carboxylic acid tert-butyl ester, 1.44 g of potassium phosphate and 0.15 g of Solvias I catalyst (Palladium, [bis(bicyclo[2.2.1]hept-2-yl)phosphine]chloro[2'-(dimethylamino-κN)[1,1'-biphenyl]-2-yl-κC] (9Cl)) are introduced into a 50 ml three-necked flask. The mixture is degassed and placed under a nitrogen atmosphere. 1 g of methyl 4-bromo-2-methoxybenzoate and 14 ml of dimethoxyethane are added. The reaction medium is again degassed, then placed under a nitrogen atmosphere and stirred at 100° C. for 18 h. It is poured onto ice-cold water, neutralized by addition of solid ammonium chloride and extracted with ethyl acetate. The organic phase is washed with water and a saturated sodium chloride solution, dried over magnesium sulfate and concentrated under reduced pressure. The residue is purified by chromatography on a silica column eluted with a heptane/ethyl acetate 96/4 to 60/40 gradient. 1.1 g of 4-(3-methoxy-4-(methoxycarbonyl) phenyl)-3,4-dihydro-2H-quinoxaline-1-carboxylic acid tert-butyl ester are obtained in the form of a colorless oil.

M+H$^+$=399

14.2: Methyl ester of 4-(3,4-dihydro-2H-quinoxalin-1-yl)-2-methoxybenzoic Acid 1.0 g of 4-(3-methoxy-4-(methoxycarbonyl)phenyl)-3,4-dihydro-2H-quinoxaline-1-carboxylic acid tert-butyl ester in 10 ml of dioxane is introduced into a round-bottomed flask equipped with a magnetic stirrer. 10 ml of a 4N solution of hydrochloric acid in dioxane are added. After stirring at ambient temperature for 18 h, the reaction medium is concentrated under vacuum. 1 g of methyl ester of 4-(3,4-dihydro-2H-quinoxalin-1-yl)-2-methoxybenzoic acid is obtained.

M+H$^+$=299

14.3: Methyl ester of 2-methoxy-4-{4-[3-(1H-pyrazol-4-yl)pyrrolidine-1-carbonyl]-3,4-dihydro-2H-quinoxalin-1-yl}benzoic Acid 0.92 g of the methyl ester of 4-(3,4-dihydro-2H-quinoxalin-1-yl)-2-methoxybenzoic acid and 15 ml of dichloromethane are introduced into a three-necked flask equipped with a magnetic stirrer and placed under an inert atmosphere. After cooling to +4° C., 1.92 ml of triethylamine and 0.33 g of triphosgene are successively added. The reaction medium is stirred at ambient temperature for 3 h. 0.64 g of 4-pyrrolidin-3-yl-1H-pyrazole dihydrochloride is then introduced and the mixture is stirred at ambient temperature for 18 h. The reaction medium is washed with a saturated aqueous sodium hydrogencarbonate solution; the organic phase is dried over sodium sulfate and concentrated under reduced pressure. The residue is chromatographed on silica gel eluted with a gradient of methanol from 2% to 4% in dichloromethane. The product obtained is rechromatographed on silica gel eluted with a dichloromethane/methanol 99/1 to 92/8 gradient. 1.06 g of 2-methoxy-4-{4-[3-(1H-pyrazol-4-yl)pyrrolidine-1-carbonyl]-3,4-dihydro-2H-quinoxalin-1-yl}benzoic acid methyl ester are obtained.

M+H$^+$=462

14.4: 2-Methoxy-4-(4-[3-(1H-pyrazol-4-yl)pyrrolidine-1-carbonyl]-3,4-dihydro-2H-quinoxalin-1-yl)benzoic Acid 1.06 g of methyl ester of 2-methoxy-4-{4-[3-(1H-pyrazol-4-yl)pyrrolidine-1-carbonyl]-3,4-dihydro-2H-quinoxalin-1-yl}benzoic acid in 12 ml of a tetrahydrofuran/water 1/1 mixture are introduced into a 50 ml round-bottomed flask equipped with a magnetic stirrer and placed under an inert atmosphere. 0.39 g of lithium hydroxide are added and the reaction mixture is stirred for 18 h. The medium is diluted with water and acidified by addition of citric acid. The precipitate formed is filtered off and washed with water. After drying under vacuum, 0.82 g of 2-methoxy-4-{4-[3-(1H-pyrazol-4-yl)pyrrolidine-1-carbonyl]-3,4-dihydro-2H-quinoxalin-1-yl}benzoic acid is obtained.

M+H$^+$=448

14.5: N-Cyclopropyl-2-methoxy-4-{4-[3-(1H-pyrazol-4-yl)pyrrolidine-1-carbonyl]-3,4-dihydro-2H-quinoxalin-1-yl}benzamide 0.22 g of 2-methoxy-4-{4-[3-(1H-pyrazol-4-yl)pyrrolidine-1-carbonyl]-3,4-dihydro-2H-quinoxalin-1-yl}benzoic acid, 0.06 g of cyclopropylamine, 0.13 g of hydroxybenzotriazole, 0.19 g of 1-(3-dimethylaminopropyl)-3-ethylcarbodiimide hydrochloride and 3.5 ml of a dioxane/dimethylformamide 5/2 mixture are introduced into a 100 ml round-bottomed flask equipped with a magnetic stirrer and placed under nitrogen atmosphere. The reaction mixture is stirred at ambient temperature for 20 h and partially concentrated under vacuum. It is diluted with water and extracted with ethyl acetate. The organic phase is washed several times with water, dried over magnesium sulfate and concentrated under reduced pressure. The residue is chromatographed on silica gel eluted with a dichloromethane/methanol 99/1 to 90/10 gradient. After triturating in ethyl ether, 0.15 g of N-cyrlopropyl-2-methoxy-4-{4-[3-(1H-pyrazol-4-yl)pyrrolidine-1-carbonyl]-3,4-dihydro-2H-quinoxalin-1-yl}benzamide is obtained.

Melting point=100° C.; M+H$^+$=487

$^1$H NMR (d$_6$-DMSO, 200 MHz), δ (ppm): 0.54 (m, 2H); 0.71 (m, 2H); 1.83 (m, 1H); 2.16 (m, 1H); 2.81 (m, 1H); 3.12-3.45 (m, 4H); 3.5-3.65 (m, 2H); 3.7-3.9 (m, 3H); 3.83 (s, 3H); 6.82 (m, 4H); 7.04 (m, 2H); 7.38 (m, 1H); 7.58 (m, 1H); 7.70 (d, 1H); 7.91 (s, 1H); 12.62 (s, 1H)

Example 15

(4-Difluoromethylene-3,4-dihydro-2H-quinolin-1-yl) (3-(pyridin-3-yl)pyrrolidin-1-yl)methanone (Example 163)

15.1: tert-Butyl 4-difluoromethylene-3,4-dihydro-2H-quinoline-1-carbamate 0.17 g of 4-oxo-3,4-dihydro-2H-quinoline-1-carboxylic acid tert-butyl ester, 0.2 ml of tributylphosphine and 1 ml of N-methylpyrrolidinone are introduced into a 25 ml round-bottomed flask equipped with a magnetic stirrer and placed under a nitrogen atmosphere. The mixture is brought to 155° C. and small fractions of 0.21 g of sodium chlorodifluoroacetate and 1 ml of N-methylpyrrolidinone are added thereto. It is subsequently heated at 155° C. for 1 h and concentrated under reduced pressure. Water and dichloromethane are added to the residue. The organic phase is concentrated under vacuum. The residue is purified by chromatography on silica eluted with dichloromethane. 0.11 g of tert-butyl 4-difluoromethylene-3,4-dihydro-2H-quinoline-1-carbamate is obtained.

15.2: 4-Difluoromethylene-1,2,3,4-tetrahydroquinoline 0.11 g of tert-butyl 4-difluoromethylene-3,4-dihydro-2H-quinoline-1-carbamate in 10 ml of dichloromethane is introduced into a round-bottomed flask equipped with a magnetic stirrer. 6 ml of a 4N solution of hydrochloric acid in dioxane are added. After stirring at ambient temperature for 6 h, the reaction medium is concentrated under vacuum. 0.07 g of 4-difluoromethylene-1,2,3,4-tetrahydroquinoline is obtained.

15.3: (4-Difluoromethylene-3,4-dihydro-2H-quinolin-1-yl)(3-(pyridin-3-yl)pyrrolidin-1-yl)methanone (Fumarate)

0.07 g of 4-difluoromethylene-1,2,3,4-tetrahydroquinoline and 5 ml of dichloromethane are introduced into a three-necked flask equipped with a magnetic stirrer and placed under an inert atmosphere. After cooling to +4° C., 0.11 ml of triethylamine and 0.39 ml of a 20% solution of phosgene in toluene are successively added. The reaction medium is stirred at ambient temperature for 2 h. The reaction medium is cooled in an ice bath and 0.08 g of 3-(pyrrolidin-3-yl)pyridine in 2 ml of dichloromethane is then introduced. The mixture is stirred at ambient temperature for 18 h. The reaction medium is washed with a 1N sodium hydroxide solution; the organic phase is dried over sodium sulfate and concentrated under reduced pressure. The residue is chromatographed on silica gel eluted with a dichloromethane/methanol 98/2 mixture. 0.05 g of (4-difluoromethylene-3,4-dihydro-2H-quinolin-1-yl)(3-(pyridin-3-yl)pyrrolidin-1-yl)methanone is obtained and is treated with fumaric acid in an ethanol/diisopropyl ether mixture to give the fumarate.

M+H$^+$=356

$^1$H NMR (d$_6$-DMSO, 200 MHz), δ (ppm): 1.9-2.05 (m, 1H); 2.15-2.3 (m, 1H); 3.2-3.45 (m, 6H); 3.55-3.85 (m, 3H); 6.62 (m, 7.6H); 6.98-7.10 (m, 2H); 7.22 (t, 1H); 7.37 (m, 1H); 7.54 (d, 1H); 7.71 (m, 1H); 8.4-8.52 (m, 2H).

Example 16

(2,3-Dihydrobenzo[1,4]oxazin-4-yl)[3-(4-fluoro-2-(trifluoromethyl)phenyl)pyrrolidin-1-yl]methanone (Compound No. 159)

16.1: tert-Butyl 3-trifluoromethanesulfonyloxy-2,5-dihydropyrrole-1-carbamate 27 ml of a 2.5N solution of n-butyllithium in hexane are added dropwise, in a 500 ml three-necked flask under nitrogen, to a solution of 9.86 ml of diisopropylamine in 40 ml of tetrahydrofuran cooled to −78° C. After stirring for ¼ of an hour, a solution of 10 g of tert-butyl 3-oxopyrrolidine-1-carbamate in 40 ml of tetrahydrofuran is added dropwise at −78° C. Finally, still at −78° C., 21.22 g of N-phenyltrifluoromethanesulfonimide are added. After stirring at ambient temperature for 14 hours, the tetrahydrofuran is evaporated and the product is purified on silica gel using a cyclohexane/ether 9/1 mixture as eluent. 10.2 g of tert-butyl 3-trifluoromethanesulfonyloxy-2,5-dihydropyrrole-1-carbamate are obtained as a 1/1 mixture with C,C,C-trifluoro-N-phenylmethanesulfonamide.

(M-tbu)+H$^+$=262

16.2: Trifluoromethanesulfonic Acid 2,5-dihydro-1H-pyrrol-3-yl Ester 10.2 g of tert-butyl 3-trifluoromethanesulfonyloxy-2,5-dihydropyrrole-1-carbamate as a 1/1 mixture with C,C,C-trifluoro-N-phenylmethanesulfonamide in 50 ml of dioxane are placed in a 500 ml round-bottomed flask. 120.5 ml of a 4N solution of hydrochloric acid in dioxane are subsequently added carefully. The reaction mixture is stirred for 3 h. The dioxane is evaporated and the product is purified on silica gel using a dichloromethane/methanol 95/5 mixture as eluent. 5 g of trifluoromethanesulfonic acid 2,5-dihydro-1H-pyrrol-3-yl ester are obtained.

M+H$^+$=218

16.3: Trifluoromethanesulfonic acid 1-(2,3-dihydrobenzo[1,4]oxazine-4-carbonyl)-2,5-dihydro-1H-pyrrol-3-yl Ester 2.7 g of 3,4-dihydro-2H-benzo[1,4]oxazine and 50 ml of dichloromethane are introduced into a 250 ml three-necked flask equipped with a magnetic stirrer and placed under an inert atmosphere. After cooling to +4° C., 9.92 ml of diisopropylethylamine and 2.97 g of triphosgene are successively added. The reaction medium is stirred at ambient temperature for 3 h. 4.52 ml of diisopropylethylamine and 3.04 g of trifluoromethanesulfonic acid 2,5-dihydro-1H-pyrrol-3-yl ester are then introduced and the mixture is stirred at ambient temperature for 18 h. The reaction medium is washed with a saturated aqueous sodium hydrogencarbonate solution; the aqueous phase is extracted twice with ethyl acetate. The organic phases are combined, dried over sodium sulfate and concentrated under reduced pressure. The residue is chromatographed on silica gel eluted with a gradient of ethyl acetate from 0% to 10% in dichloromethane. 4.4 g of trifluoromethanesulfonic acid 1-(2,3-dihydrobenzo[1,4]oxazine-4-carbonyl)-2,5-dihydro-1H-pyrrol-3-yl ester are obtained.

M+H$^+$=379.1

16.4: (2,3-Dihydrobenzo[1,4]oxazin-4-yl)[3-(4,4,5,5-tetramethyl-[1,3,2]dioxaborolan-2-yl)-2,5-dihydropyrrol-1-yl]methanone 2.2 g of trifluoromethanesulfonic acid 1-(2,3-dihydrobenzo[1,4]oxazine-4-carbonyl)-2,5-dihydro-1H-pyrrol-3-yl ester, 1.92 g of bis(pinacolato)diboron, 0.28 g of bis(diphenylphosphino)ferrocenedichloropalladium(II), 1.7 g of potassium acetate and 0.06 g of 1,1'-bis(diphenylphosphino)ferrocene are introduced into a 100 ml three-necked flask equipped with a magnetic stirrer and placed under an inert atmosphere. The reaction medium is brought to reflux for 14 h and then concentrated under reduced pressure. Water and ethyl acetate are added and the heterogeneous mixture is filtered through celite. The organic phase is washed with water, dried over sodium sulfate and concentrated under reduced pressure. The residue is chromatographed on silica gel eluted with a gradient of ethyl acetate from 30% to 50% in heptane. 1.22 g of (2,3-dihydrobenzo[1,4]oxazin-4-yl)[3-(4,4,5,5-tetramethyl-[1,3,2]dioxaborolan-2-yl)-2,5-dihydropyrrol-1-yl]methanone are obtained.

M+H$^+$=357.2

16.5: (2,3-Dihydrobenzo[1,4]oxazin-4-yl)[3-(4-fluoro-2-(trifluoromethyl)phenyl)-2,5-dihydropyrrol-1-yl]methanone 0.4 g of (2,3-dihydrobenzo[1,4]oxazin-4-yl)[3-(4,4,5,5-tetramethyl-[1,3,2]dioxaborolan-2-yl)-2,5-dihydropyrrol-1-yl]methanone, 0.4 g of 1-bromo-4-fluoro-2-(trifluoromethyl)benzene, 1.4 ml of a 2N solution of sodium carbonate in water and 15 ml of ethylene glycol dimethyl ether are placed in a 100 ml three-necked flask equipped with a magnetic stirrer and placed under an inert atmosphere. The reaction mixture is degassed with nitrogen for 30 minutes and then the reaction mixture is heated at reflux for 14 h. After filtering and concentrating to dryness, the crude reaction product obtained is chromatographed on silica gel, elution being carried out with a gradient of ethyl acetate in dichloromethane varying from 0% to 10%. 0.31 g of (2,3-dihydrobenzo[1,4]oxazin-4-yl)[3-(4-fluoro-2-(trifluoromethyl)phenyl)-2,5-dihydropyrrol-1-yl]methanone is obtained.

M+H$^+$=393.1

16.6: (2,3-Dihydrobenzo[1,4]oxazin-4-yl)[3-(4-fluoro-2-(trifluoromethyl)phenyl)pyrrolidin-1-yl]methanone 0.07 g of (2,3-dihydrobenzo[1,4]oxazin-4-yl)[3-(4-fluoro-2-(trifluoromethyl)phenyl)-2,5-dihydropyrrol-1-yl]methanone in 3.57 ml of methanol is hydrogenated in an H-Cube device under hydrogen at atmospheric pressure with a cartridge of 100 mg of 10% palladium-on-charcoal. After concentrating to dryness, the crude reaction product obtained is chromatographed on silica gel, elution being carried out with a mixture of 5% of ethyl acetate in dichloromethane. 0.15 g of (2,3-dihydrobenzo[1,4]oxazin-4-yl)[3-(4-fluoro-2-(trifluoromethyl)phenyl)pyrrolidin-1-yl]methanone is obtained.

M+H$^+$=395.2

$^1$H NMR (d$_6$-DMSO, 400 MHz), δ (ppm): 2.08-2.2 (m, 1H); 2.22-2.34 (m, 1H); 3.42-3.88 (m, 7H); 4.2-4.3 (m, 1H); 4.31-4.4 (m, 1H); 6.81-6.96 (m, 3H); 7.15-7.21 (m, 1H); 7.6-7.7 (m, 2H); 7.78-7.84 (m, 1H)

Example 17

2,2-Difluoro-1'-{[3-(1H-pyrazol-4-yl)pyrrolidin-1-yl]carbonyl}-2',3'-dihydro-1'H-spiro[cyclopropane-1,4'-quinoline] (Example 183)

17.1: tert-Butyl 4-methylene-3,4-dihydro-2H-quinoline-1-carbamate 3.96 ml of a 1N solution of potassium tert-butoxide in tetrahydrofuran, 1.45 g of methyltriphenylphosphonium bromide and 30 ml of dimethyl ether are placed in a 150 ml three-necked flask equipped with a magnetic stirrer and placed under an inert atmosphere. The reaction mixture is heated at reflux for 1 h. After returning to ambient temperature, 0.7 g of tert-butyl 4-oxo-3,4-dihydro-2H-quinoline-1-carbamate is added and the reaction mixture is heated at reflux for 1.5 h and then concentrated under reduced pressure. Water and ethyl acetate are added. The organic phase is washed with water, dried over magnesium sulfate and concentrated under reduced pressure. The residue is chromatographed on silica gel eluted with dichloromethane. 0.556 g of tert-butyl 4-methylene-3,4-dihydro-2H-quinoline-1-carbamate is obtained.

$^1$H NMR (CDCl$_3$, 200 MHz), δ (ppm): 1.4 (s, 9H); 2.53-2.68 (m, 2H); 3.62-3.74 (m, 2H); 4.85 (s, 1H); 5.49 (s, 1H); 6.89-7.18 (m, 2H); 7.42-7.6 (m, 2H)

17.2: tert-Butyl 2,2-difluoro-2',3'-dihydro-1'H-spiro[cyclopropane-1,4'-quinoline]-1'-carbamate 0.275 g of tert-butyl 4-methylene-3,4-dihydro-2H-quinoline-1-carbamate, 0.0028 g of sodium fluoride and 1.5 ml of toluene are placed in a 10 ml round-bottomed flask equipped with a magnetic stirrer and placed under an inert atmosphere. The reaction mixture is heated at reflux for 1 h. 0.449 g of methyl fluorosulfonyldifluoroacetate is subsequently added and the reaction mixture is heated at reflux for 2 h, filtered through celite and then concentrated under reduced pressure. The residue is chromatographed twice on silica gel eluted with dichloromethane. 0.23 g of tert-butyl 2,2-difluoro-2',3'-dihydro-1'H-spiro[cyclopropane-1,4'-quinoline]-1'-carbamate is obtained.

M+H$^+$=296.2

17.3: 2,2-Difluoro-2',3'-dihydro-1'H-spiro[cyclopropane-1,4'-quinoline]

0.105 g of tert-butyl 2,2-difluoro-2',3'-dihydro-1'H-spiro[cyclopropane-1,4'-quinoline]-1'-carbamate is dissolved in 5 ml of dichloromethane and then 7.78 ml of a 4N solution of hydrochloric acid in dioxane are added. Stirring is maintained for 14 hours. After evaporating, the residue is taken up in dichloromethane and then hydrolyzed with a saturated solution of sodium hydrogencarbonate in water. The mixture is extracted twice with dichloromethane. The organic phases are combined, washed with water and then with a saturated solution of sodium hydrogencarbonate in water and then dried over magnesium sulfate and the solvent is evaporated under reduced pressure. 0.588 g of 2,2-difluoro-2',3'-dihydro-1'H-spiro[cyclopropane-1,4'-quinoline] is obtained.

M+H$^+$=196.3

17.4: 2,2-Difluoro-1'-{[3-(1H-pyrazol-4-yl)pyrrolidin-1-yl]carbonyl}-2',3'-dihydro-1'H-spiro[cyclopropane-1,4'-quinoline]

0.071 g of 2,2-difluoro-2',3'-dihydro-1'H-spiro[cyclopropane-1,4'-quinoline], 0.03 ml of pyridine and 8.4 ml of dichloromethane are placed in a 50 ml round-bottomed flask under a nitrogen atmosphere. 0.17 ml of a 20% solution of phosgene in toluene is added at 0° C. and then the reaction mixture is left stirring at 0° C. for ½ hour and at ambient temperature for one hour. 0.05 ml of triethylamine and 0.044 g of 4-(pyrrolidin-3-yl)-1H-pyrazole dihydrochloride are subsequently added at 0° C. and the reaction mixture is stirred for eighteen hours and then concentrated under reduced pressure. The residue is chromatographed on silica gel eluted with a 5% mixture of methanol in dichloromethane. 0.038 g of 2,2-difluoro-1'-{[3-(1H-pyrazol-4-yl)pyrrolidin-1-yl]carbonyl}-2',3'-dihydro-1'H-spiro[cyclopropane-1,4'-quinoline] is obtained.

M+H$^+$=359.3

$^1$H NMR (d$_6$-DMSO, 300 MHz), δ (ppm): 1.2-1.3 (bs, 1H); 1.45-1.6 (m, 1H); 1.5-2.6 (m, 6H); 3-3.8 (m, 5H); 6.81-7.2 (m, 4H); 7.2-7.7 (m, 2H)

The chemical structures and the physical properties of some compounds according to the invention are illustrated in the following table. In this table:

- in the "salt" column, "—" represents a compound in the form of the free base, while "HCl" represents a compound in the hydrochloride form, Ox. a compound in the oxalate form, Fum. a compound in the fumarate form and Na$^+$ a sodium salt and the ratio in brackets is the (acid:base) ratio, if it is not equal to 1,
- Me and Et respectively represent methyl and ethyl groups;
- Bn represents the benzyl group.

TABLE

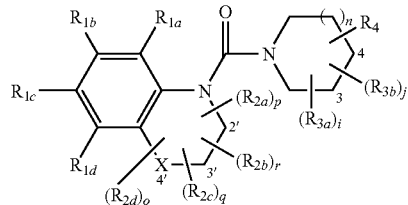

in Examples 1 to 205 below: o = q = j = 0, i = p = r = 1

| No. | X | n | $R_{1a}$ | $R_{1b}$ | $R_{1c}$ | $R_{1d}$ | $R_{2a}$ | $R_{2b}$ |
|---|---|---|---|---|---|---|---|---|
| 1 | C | 1 | H | H | H | H | H | H |
| 2 | O | 1 | H | H | H | H | H | 2-CH$_3$ |
| 3 | O | 1 | H | 8-Cl | H | H | H | H |
| 4 | C | 1 | H | H | H | H | H | H |
| 5 | C | 1 | H | H | H | H | H | H |
| 6 | C | 1 | H | H | H | H | H | H |
| 7 | C | 1 | H | H | H | H | H | 2-CH$_3$ |
| 8 | C | 1 | H | H | H | H | H | 2-CH$_3$ |
| 9 | C | 1 | H | H | H | H | H | 2-CH$_3$ |
| 10 | C | 1 | H | H | H | H | H | 2-CH$_3$ |
| 11 | C | 1 | H | H | H | H | H | H |
| 12 | C | 1 | H | H | H | H | H | 2-CH$_3$ |
| 13 | C | 1 | H | H | H | H | H | H |
| 14 | C | 1 | H | H | H | H | H | H |
| 15 | C | 1 | H | H | H | H | H | H |
| 16 | C | 1 | H | H | H | H | H | H |
| 17 | C | 1 | H | H | H | H | H | H |
| 18 | C | 1 | H | H | H | H | H | H |
| 19 | C | 0 | H | H | H | H | H | H |
| 20 | C | 0 | H | H | H | H | H | H |
| 21 | C | 0 | H | F | H | H | H | H |
| 22 | C | 1 | H | H | H | H | H | H |
| 23 | C | 1 | H | H | H | H | H | H |
| 24 | C | 1 | H | H | H | H | H | H |
| 25 | C | 1 | H | H | H | H | H | H |
| 26 | O | 0 | H | H | H | H | H | H |
| 27 | C | 0 | H | H | H | H | H | H |
| 28 | C | 1 | H | H | H | H | H | H |
| 29 | C | 1 | H | H | H | H | H | H |
| 30 | C | 1 | H | H | H | H | H | H |
| 31 | C | 0 | H | H | H | H | H | H |
| 32 | O | 1 | H | H | Cl | H | H | H |
| 33 | C | 1 | H | H | H | H | H | H |
| 34 | C | 1 | H | H | H | H | H | H |
| 35 | C | 1 | H | H | H | H | H | H |
| 36 | O | 1 | H | F | H | H | H | H |
| 37 | O | 0 | H | F | H | H | H | H |
| 38 | O | 1 | H | H | Cl | H | H | H |
| 39 | S | 0 | H | H | H | H | H | H |
| 40 | O | 0 | H | OMe | H | H | H | H |
| 41 | O | 0 | H | H | F | H | H | H |
| 42 | C | 0 | H | H | H | H | H | H |
| 43 | C | 1 | H | H | H | H | H | H |
| 44 | O | 1 | H | H | H | H | H | H |
| 45 | O | 1 | H | H | H | H | H | H |
| 46 | C | 1 | H | H | H | H | H | H |
| 47 | C | 1 | H | H | H | H | H | H |
| 48 | C | 1 | H | H | H | H | H | H |
| 49 | C | 1 | H | H | H | H | H | H |
| 50 | C | 1 | H | H | H | H | H | H |
| 51 | C | 0 | H | H | H | H | H | H |
| 52 | C | 0 | H | H | H | H | H | H |
| 53 | C | 1 | H | H | H | H | H | H |
| 54 | C | 0 | H | H | H | H | H | H |
| 55 | O | 0 | H | Cl | H | H | H | H |
| 56 | N | 0 | H | H | H | H | H | H |
| 57 | C | 0 | H | H | H | H | H | H |
| 58 | C | 0 | H | H | H | H | H | H |
| 59 | C | 0 | H | H | Me | H | H | H |
| 60 | C | 0 | H | H | H | H | H | H |
| 61 | C | 0 | H | H | H | H | H | H |
| 62 | N | 0 | H | H | H | H | 4-Me | H |

TABLE-continued

| | | | | | | | | |
|---|---|---|---|---|---|---|---|---|
| 63 | O | 0 | H | F | F | H | H | H |
| 64 | C | 0 | H | H | H | H | H | H |
| 65 | C | 0 | H | H | H | H | H | H |
| 66 | C | 0 | H | CF$_3$ | H | H | H | H |
| 67 | C | 0 | H | CF$_3$ | H | H | H | H |
| 68 | C | 0 | H | H | Br | H | H | H |
| 69 | S | 1 | H | H | H | H | H | H |
| 70 | C | 0 | H | H | H | H | H | H |
| 71 | C | 0 | H | H | OMe | H | H | H |
| 72 | C | 0 | H | H | CO$_2$Me | H | H | H |
| 73 | O | 0 | H | H | H | H | H | H |
| 74 | O | 0 | H | H | H | H | 4'=O | H |
| 75 | O | 0 | H | H | SO$_2$—NHMe | H | H | H |
| 76 | O | 0 | H | CO$_2$Me | H | H | H | H |
| 77 | C | 0 | OH | H | H | H | H | H |
| 78 | O | 0 | H | Cl | H | H | H | H |
| 79 | C | 0 | H | H | CO$_2$H | H | H | H |
| 80 | O | 0 | H | H | H | H | H | H |
| 81 | O | 0 | H | F | H | H | H | H |
| 82 | O | 0 | H | CH$_2$OH | H | H | H | H |
| 83 | O | 0 | H | H | H | H | H | H |
| 84 | C | 0 | H | H | H | H | 4'-NH$_2$ | H |
| 85 | C | 0 | H | H | H | H | H | H |
| 86 | C | 0 | H | H | H | H | H | H |
| 87 | C | 0 | H | H | H | H | H | H |
| 88 | C | 0 | H | H | H | H | H | H |
| 89 | O | 0 | H | H | H | H | H | H |
| 90 | O | 0 | H | H | H | H | H | H |
| 91 | O | 0 | H | H | H | H | H | H |
| 92 | O | 0 | H | H | H | H | H | H |
| 93 | O | 0 | H | H | H | H | H | H |
| 94 | O | 0 | H | H | H | H | H | H |
| 95 | O | 0 | H | H | H | H | H | H |
| 96 | O | 0 | H | H | H | H | H | H |
| 97 | O | 0 | H | H | H | H | H | H |
| 98 | O | 0 | H | H | H | H | H | H |
| 99 | C | 0 | H | H | SO$_2$—NMe$_2$ | H | H | H |
| 100 | N | 0 | H | H | H | H | 4'-Et | H |
| 101 | N | 0 | H | H | H | H | 4'-nPr | H |
| 102 | O | 0 | H | H | H | H | H | H |
| 103 | O | 0 | H | H | H | H | H | H |
| 104 | O | 0 | H | H | H | H | H | H |
| 105 | C | 0 | H | H | H | H | 4'-Me | 4'-Me |
| 106 | C | 0 | H | H | H | H | 4'-Me | 4'-Me |
| 107 | C | 0 | H | H | H | H | H | H |
| 108 | O | 0 | H | H | H | H | H | H |
| 109 | C | 0 | H | H | H | H | H | H |
| 110 | N | 0 | H | H | H | H | 4'CO—NMe$_2$ | H |
| 111 | O | 0 | H | H | H | H | H | H |
| 112 | C | 0 | H | H | H | H | H | H |
| 113 | O | 0 | H | H | H | H | H | H |
| 114 | O | 0 | H | H | H | H | H | H |
| 115 | O | 0 | H | H | H | H | H | H |
| 116 | O | 0 | H | H | H | H | H | H |
| 117 | C | 0 | H | H | H | H | 4'-OH | H |
| 118 | N | 0 | H | H | H | H | 4'-COOMe | H |
| 119 | N | 0 | H | H | H | H | 4'-nButyl | H |
| 120 | N | 0 | H | H | H | H | 4'-COOMe | H |
| 121 | N | 0 | H | H | H | H | 4'-Bn | H |
| 122 | N | 0 | H | H | H | H | 4'-Me | H |
| 123 | N | 0 | H | H | H | H | 4'-Me | H |
| 124 | O | 0 | H | Cl | H | H | H | H |
| 125 | O | 0 | H | Cl | H | H | H | H |
| 126 | O | 0 | H | Cl | H | H | H | H |
| 127 | O | 0 | H | Cl | H | H | H | H |
| 128 | O | 0 | H | Cl | H | H | H | H |
| 129 | O | 0 | H | Cl | H | H | H | H |
| 130 | C | 0 | H | Cl | H | H | 4'-Me | 4'-Me |
| 131 | C | 0 | H | F | F | H | 4'-Me | 4'-Me |
| 132 | C | 0 | H | F | F | H | 4'-Me | 4'-Me |

TABLE-continued

| | | | | | | | | |
|---|---|---|---|---|---|---|---|---|
| 133 | N | 0 | H | H | H | H | 4'-C₆H₄-CN (para) | H |
| 134 | C | 0 | H | MeO | H | H | 4'-Me | 4'-Me |
| 135 | C | 0 | H | H | H | H | 4'-cyclopropyl | |
| 136 | C | 0 | H | H | H | H | 4'-Me | 4'-Me |
| 137 | C | 0 | H | H | H | H | 4'-Me | 4'-Me |
| 138 | C | 0 | H | H | H | H | H | H |
| 139 | H | 0 | H | H | H | H | H | H |
| 140 | N | 0 | H | H | H | H | 4'-CH₂-C₆H₄-CN (para) | H |
| 141 | C | 0 | H | H | H | H | 4'-cyclopentyl | |
| 142 | C | 0 | H | H | Cl | H | 4'-Me | 4'-Me |
| 143 | O | 0 | H | CF₃ | H | H | H | H |
| 144 | O | 0 | H | CF₃ | H | H | H | H |
| 145 | C | 0 | H | H | H | H | H | H |
| 146 | C | 0 | H | H | H | H | 4'-Me | 4'-Me |
| 147 | C | 0 | H | H | H | Cl | 4'-Me | 4'-Me |
| 148 | N | 0 | H | H | H | H | H | H |
| 149 | O | 0 | H | H | H | H | H | H |
| 150 | N | 0 | H | H | H | H | H | 4'-(CH₂)₂-morpholinyl |
| 151 | C | 0 | H | H | H | H | OH | H |
| 152 | N | 0 | H | H | H | H | H | 4'-CH₂-morpholinyl |
| 153 | C | 0 | H | C | H | H | 4'-Me | 4'-Me |
| 154 | O | 0 | H | H | H | H | 2'-Me | H |
| 155 | O | 0 | H | H | H | H | H | H |
| 156 | N | 0 | H | H | H | H | H | 4'-CF₃ |

TABLE-continued
| | | | | | | | |
|---|---|---|---|---|---|---|---|
| 157 | N | 0 | H | H | H | H | H | 4'-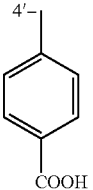 |
| 158 | N | 0 | H | H | H | H | H | 4'-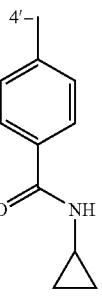 |
| 159 | O | 0 | H | H | H | H | H | H |
| 160 | N | 0 | H | H | H | H | H | 4'-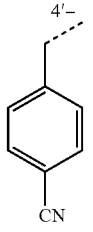 |
| 161 | N | 0 | H | H | H | H | H | 4'-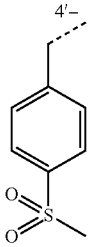 |
| 162 | N | 0 | H | H | H | H | H | 4'-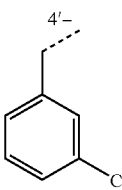 |
| 163 | C | 0 | H | H | H | H | H | 4-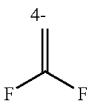 |
| 164 | N | 0 | H | H | H | H | H | 4'-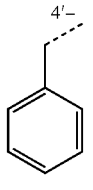 |
| 165 | O | 0 | H | H | H | H | H | H |
| 166 | N | 0 | H | H | H | H | H | H |
| 167 | N | 0 | H | F | F | H | H | H |

TABLE-continued
| 168 | N | 0 | H | H | H | H | H | 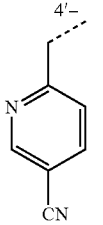 |
| 169 | N | 0 | H | H | H | H | H | H |
| 170 | O | 0 | H | H | H | H | H | H |
| 171 | N | 0 | H | H | H | H | H | 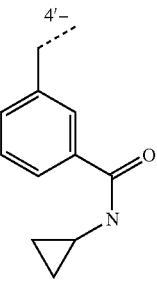 |
| 172 | N | 0 | H | H | H | H | H | 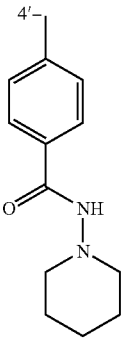 |
| 173 | N | 0 | H | H | H | H | H | 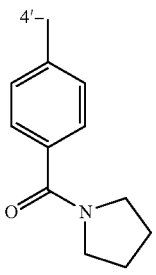 |
| 174 | N | 0 | H | H | H | H | H | 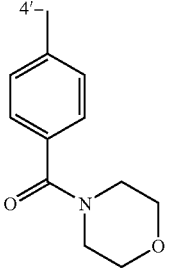 |

TABLE-continued

| | | | | | | | | |
|---|---|---|---|---|---|---|---|---|
| 175 | N | 0 | H | H | H | H | H | 4'- (4-methylpiperazin-1-yl)carbonyl-phenyl |
| 176 | N | 0 | H | H | H | H | H | 4'- [4-(N-cyclopropylcarbamoylmethyl)phenyl] |
| 177 | N | 0 | H | H | H | H | H | 4'- [4-(trifluoromethylsulfonyloxy)phenyl] |
| 178 | N | 0 | H | H | H | H | H | 4'- [4-(N-cyclopropylcarbamoyl)-3-methoxyphenyl] |
| 179 | N | 0 | H | H | H | H | H | 4'- [4-cyano-3-(trifluoromethyl)phenyl] |
| 180 | N | 0 | H | H | H | H | H | 4'- [4-(N-cyclopropylcarbamoylmethoxy)phenyl] |

TABLE-continued
| | | | | | | | | |
|---|---|---|---|---|---|---|---|---|
| 181 | N | 0 | H | H | H | H | H | 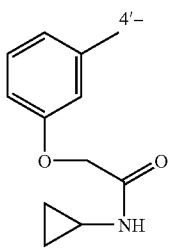 4'- |
| 182 | N | 0 | H | H | H | H | H | 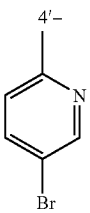 4'- |
| 183 | C | 0 | H | H | H | H | | 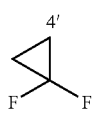 4' |
| 184 | C | 0 | H | H | H | H | H | 4-COOMe |
| 185 | O | 0 | H | H | H | CF$_3$ | H | H |
| 186 | N | 0 | H | H | H | H | H | 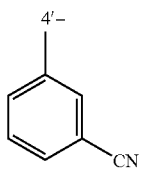 4'- |
| 187 | N | 0 | H | H | H | H | H | 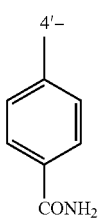 4'- |
| 188 | N | 0 | H | H | H | H | H | 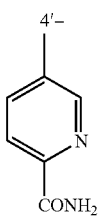 4'- |
| 189 | N | 0 | H | H | H | H | H | 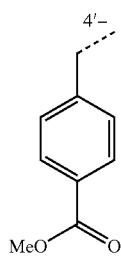 4'- |

TABLE-continued
| 190 | N | 0 | H | H | H | H | H | 4'- 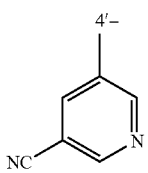 |
| 191 | N | 0 | H | H | H | H | H | 4'- 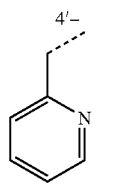 |
| 192 | O | 0 | H | H | H | H | H | H |
| 193 | O | 0 | H | H | H | H | H | H |
| 194 | N | 0 | H | H | H | H | H | 4'- 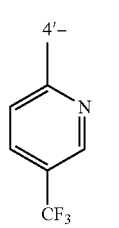 |
| 195 | N | 0 | H | H | H | H | H | 4'- 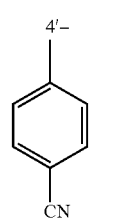 |
| 196 | N | 0 | H | H | H | H | H | 4'- 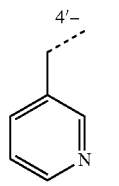 |
| 197 | N | 0 | H | H | H | H | H | 4'- 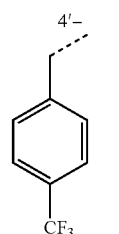 |
| 198 | O | 0 | H | H | H | Cl | H | H |
| 199 | N | 0 | H | H | H | H | H | 4'- 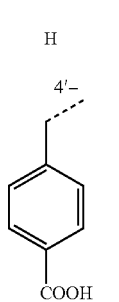 |

TABLE-continued

| | | | | | | | | |
|---|---|---|---|---|---|---|---|---|
| 200 | N | 0 | H | H | H | H | H | 4'- [4-(1,2,4-triazol-1-yl)phenyl] |
| 201 | O | 0 | H | H | H | H | H | H |
| 202 (S) | N | 0 | H | H | H | H | H | 4'- [4-cyanophenyl] |
| 203 | N | 0 | H | H | H | H | H | 4'- [4-cyanophenyl] |
| 204 | N | 0 | H | H | H | H | H | 4'- [4-carbamoylphenyl] |
| 205 | N | 0 | H | H | H | H | H | 4'- [5-(ethoxycarbonyl)pyridin-3-yl] |
| 206 | N | 0 | H | H | H | H | H | 4'- [4-(cyclopropylcarbamoyl)phenyl] |

| | | | | | | | |
|---|---|---|---|---|---|---|---|
| 207 | N | 0 | H | H | H | H | H | 4'– 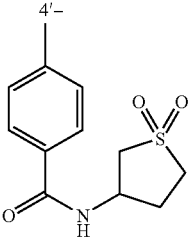 |
| 208 | N | 0 | H | H | H | H | H | 4'– 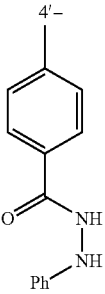 |
| 209 | N | 0 | H | H | H | H | H | 4'– 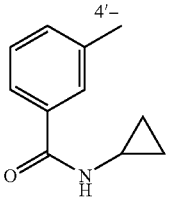 |
| 210 | N | 0 | H | H | H | H | H | 4'– 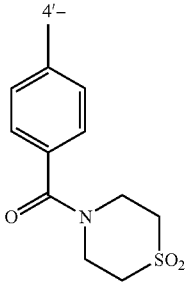 |
| No. | R$_{3a}$ | R$_4$ | Salt | M.p. (° C.) | M + H$^+$ | Synthesis |
|---|---|---|---|---|---|---|
| 1 | H | 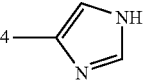 | Ox. (1/2) | 215-216 | — | Method 1 |
| 2 | H | 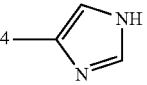 | Ox. (1/2) | 205 | — | Method 1 |
| 3 | H | 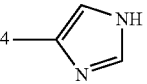 | Ox. (1/2) | 205 | — | Method 1 |
| 4 | H | 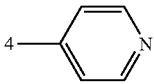 | HCl | 198 | — | Method 2 |
| 5 | H | 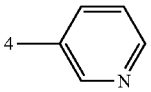 | HCl | 148-150 | — | Method 2 |

TABLE-continued
| | | | | | | |
|---|---|---|---|---|---|---|
| 6 | H | 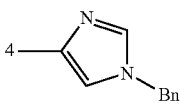 | Ox. (1/2) | 117-120 | 401.2 | Method 8 |
| 7 | H | 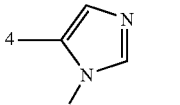 | Ox. (1/2) | 70-110 | 339.4 | Method 8 |
| 8 | H | 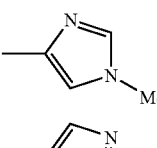 | — | 71-80 | — | Method 1 |
| 9 | H | 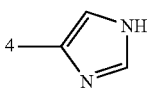 | HCl | 71-105 | — | Method 1 |
| 10 | 4-CN | 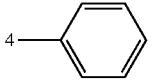 | — | 45-55 | — | Method 1 |
| 11 | H | 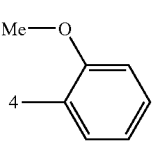 | — | — | 351 | Method 1 |
| 12 | H | 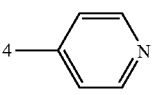 | HCl | 85-100 | — | Method 2 |
| 13 | H | 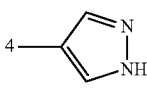 | — | 141-161 | — | Method 2 |
| 14 | H | 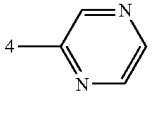 | — | — | 323.3 | Method 2 |
| 15 | | 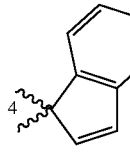 | — | 130-133 | — | Method 1 |
| 16 | | 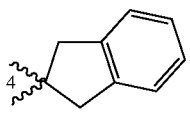 | — | 119-125 | — | Method 1 |
| 17 | 4-CN | 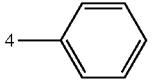 | — | 53-59 | — | Method 3 |

TABLE-continued

| | | | | | | |
|---|---|---|---|---|---|---|
| 18 | | tetrahydronaphthalenyl (4-position) | — | 52-65 | — | Method 1 |
| 19 | H | 3-pyridyl (4-) | HCl | 159-163 | — | Method 2 |
| 20 | H | 4-pyridyl (4-) | HCl | 204-208 | — | Method 2 |
| 21 | H | 4-pyridyl (4-) | HCl | 205 | — | Method 1 |
| 22 | H | 4-phenylthiazol-2-yl (4-) | — | 135 | — | Method 5 |
| 23 | H | 1,2,4-oxadiazol-3-yl (4-) | — | 95 | — | Method 7 |
| 24 | H | thiazol-2-yl (4-) | — | 85 | — | Method 5 |
| 25 | H | 5-(2,6-dichlorophenyl)-1,2,4-oxadiazol-3-yl (4-) | — | 63-68 | — | Method 6 |
| 26 | H | 3-pyridyl (4-) | HCl | 60-90 | 310.4 | Method 1 |
| 27 | H | 5-fluoro-3-pyridyl (4-) | HCl | — | 326 | Method 1 |
| 28 | 4-CN | cyclohexyl (4-) | — | 124 | — | Method 4 |
| 29 | 4-CN | 4-Me | — | — | 284.2 | Method 4 |
| 30 | 4-CN | 4-Et | — | — | 298.4 | Method 4 |
| 31 | H | 1H-pyrazol-3-yl (4-) | — | — | 297.4 | Method 2 |

TABLE-continued
| | | | | | | |
|---|---|---|---|---|---|---|
| 32 | H | 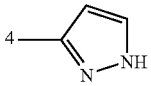 | — | 85 | — | Method 2 |
| 33 | | 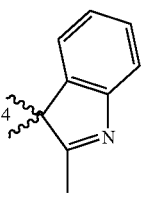 | — | 126 | — | Method 1 |
| 34 | | 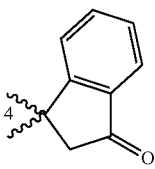 | — | 152 | — | Method 1 |
| 35 | | 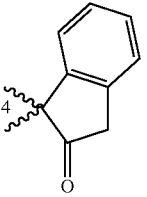 | — | 190 | — | Method 1 |
| 36 | H | 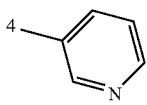 | HCl | 205 | — | Method 1 |
| 37 | H | 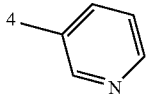 | — | 85 | — | Method 1 |
| 38 | H | 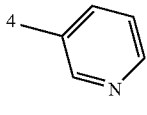 | HCl | 205 | — | Method 1 |
| 39 | H | 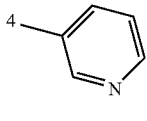 | — | — | 326.2 | Method 1 |
| 40 | H | 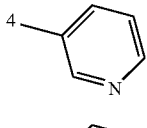 | HCl | 90-92 | — | Method 1 |
| 41 | H | 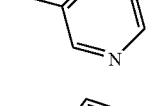 | HCl | 107-110 | — | Method 1 |
| 42 | H | 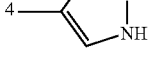 | — | 123-130 | — | Method 2 |
| 43 | | 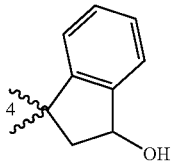 | — | 80 | — | Method 1 |

| | | | | | | |
|---|---|---|---|---|---|---|
| 44 | H | 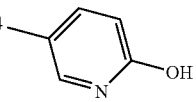 | — | 202-208 | — | Method 2 |
| 45 | H | 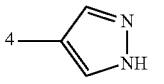 | — | 153-158 | — | Method 1 |
| 46 | H | 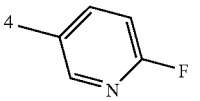 | — | 106 | — | Method 1 |
| 47 | H | 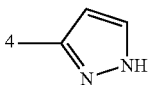 | — | — | 311.3 | Method 2 |
| 48 | H | 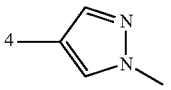 | — | — | 325.4 | Method 1 |
| 49 | H | 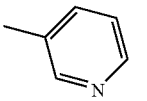 | HCl | 65-Dec. | — | Method 1 |
| 50 | H | 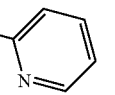 | HCl | 50-65 | — | Method 1 |
| 51 | 4-OH | 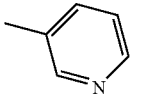 | Fum. | 50-65 | — | Method 1 |
| 52 | H | 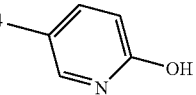 | — | 75 | — | Method 2 |
| 53 | | 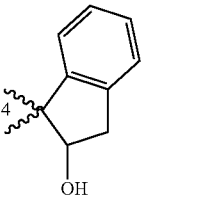 | — | 80 | — | Method 1 |
| 54 | H | 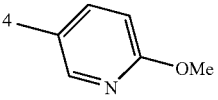 | — | 124-130 | — | Method 2 |
| 55 | H | 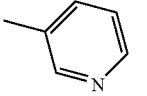 | — | 150 | — | Method 1 |
| 56 | H | 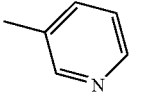 | HCl | 125-128 | — | Method 1 |

TABLE-continued
| | | | | | | |
|---|---|---|---|---|---|---|
| 57 | H | 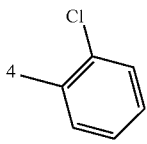 | — | 105-109 | — | Method 1 |
| 58 | H | 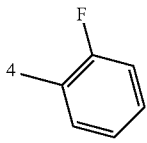 | — | 110-114 | — | Method 1 |
| 59 | H | 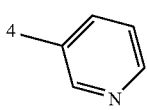 | HCl | 95 | — | Method 1 |
| 60 | | 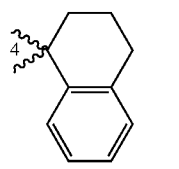 | — | — | 347.3 | Method 1 |
| 61 | H | 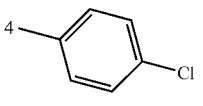 | — | 112-117 | — | Method 1 |
| 62 | H | 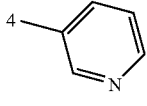 | HCl | 126-128 | — | Method 1 |
| 63 | H | 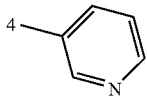 | HCl | 212 | — | Method 1 |
| 64 | H | 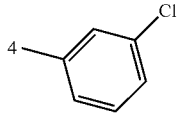 | — | — | 341.3 | Method 1 |
| 65 | H | 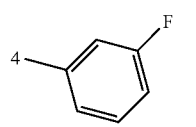 | — | — | 325.3 | Method 1 |
| 66 | H | 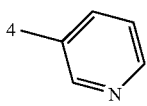 | HCl | 116 | — | Method 1 |
| 67 | H | 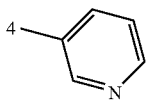 | HCl | 116 | — | Method 1 |
| 68 | H | 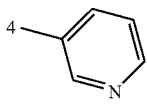 | HCl | 87 | — | Method 1 |

TABLE-continued
| | | | | | | | |
|---|---|---|---|---|---|---|---|
| 69 | H | 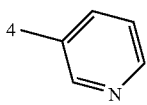 | HCl | — | 340.3 | Method 1 |
| 70 | H | 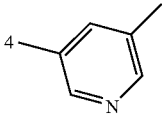 | HCl | 100-130 | — | Method 2 |
| 71 | H | 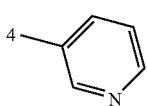 | HCl | — | 338.3 | Method 1 |
| 72 | H | 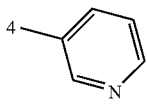 | HCl | 186-188 | — | Method 1 |
| 73 | H | 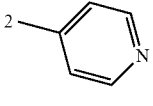 | — | — | 308.3 | Method 1 |
| 74 | H | 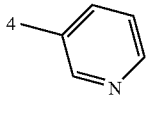 | HCl | — | 322.3 | Method 1 |
| 75 | H | 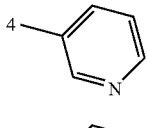 | HCl | — | 401.3 | Method 1 |
| 76 | H | 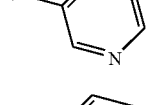 | — | 61 | — | Method 1 |
| 77 | H | 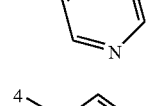 | — | 103 | — | Method 1 |
| 78 | H | 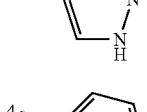 | — | 60 | — | Method 1 |
| 79 | H | 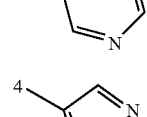 | Na+ | 197-202 | — | Method 13 |
| 80 | H | 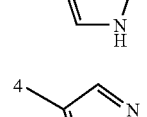 | — | 65 | — | Method 1 |
| 81 | H | 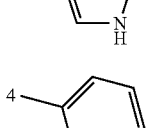 | — | 50 | — | Method 1 |
| 82 | H | 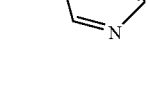 | HCl | 273 | — | Method 1 |

TABLE-continued
| | | | | | | |
|---|---|---|---|---|---|---|
| 83 | H | 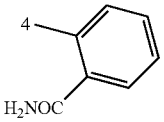 | — | 92 | — | Method 2 |
| 84 | H | 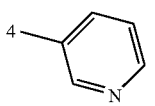 | HCl | 112-120 | — | Method 1 |
| 85 | H | 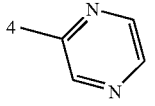 | — | — | 309.3 | Method 2 |
| 86 | H | 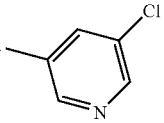 | — | — | 342.3 | Method 2 |
| 87 | H | 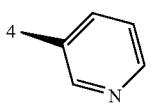 | HCl | — | 308.3 | Method 1 |
| 88 | H | 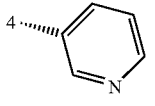 | HCl | — | 308.3 | Method 1 |
| 89 | H | 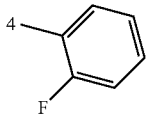 | — | — | 327.3 | Method 1 |
| 90 | H | 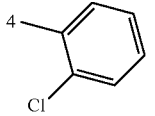 | — | — | 343.2 | Method 1 |
| 91 | H | 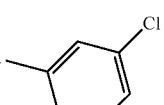 | — | — | 343.2 | Method 1 |
| 92 | | 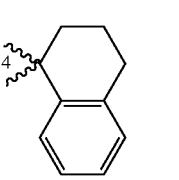 | — | 55-60 | — | Method 1 |
| 93 | H | 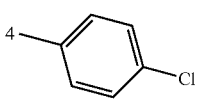 | — | — | 343.2 | Method 1 |
| 94 | H | 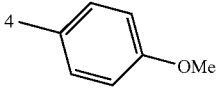 | — | — | 339.3 | Method 1 |

TABLE-continued
| | | | | | | |
|---|---|---|---|---|---|---|
| 95 | H | 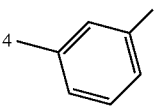 4-(3-CF₃-phenyl) | — | — | 377.2 | Method 1 |
| 96 | H | 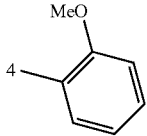 4-(2-MeO-phenyl) | — | 96-99 | — | Method 1 |
| 97 | H | 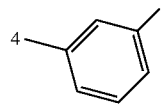 4-(3-F-phenyl) | — | — | 327.3 | Method 1 |
| 98 | H | 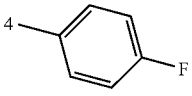 4-(4-F-phenyl) | — | — | 327.3 | Method 1 |
| 99 | H | 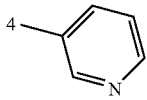 4-(3-pyridyl) | HCl | 198-200 | — | Method 1 |
| 100 | H | 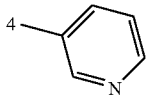 4-(3-pyridyl) | HCl | 202 | — | Method 9 |
| 101 | H | 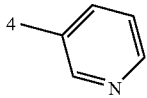 4-(3-pyridyl) | HCl | 121 | — | Method 9 |
| 102 | H | 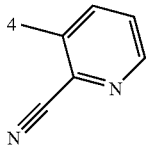 | HCl | 140-142 | — | Method 2 |
| 103 | H | 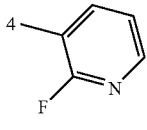 | HCl | — | 328.3 | Method 2 |
| 104 | H | 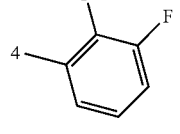 | — | 60 | — | Method 1 |
| 105 | H | 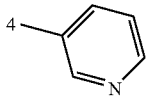 | — | 60 | — | Method 1 |
| 106 | H | 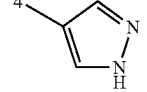 | — | 55 | — | Method 1 |

TABLE-continued
| | | | | | | |
|---|---|---|---|---|---|---|
| 107 | 4-CN | 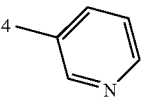 | — | 60 | — | Method 1 |
| 108 | 4-CN | 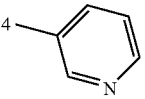 | — | 50 | — | Method 1 |
| 109 | 4-CN | 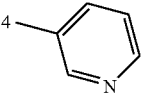 | — | 92 | — | Method 1 |
| 110 | H | 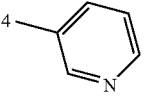 | HCl | 181 | — | Method 10 |
| 111 | H | 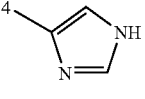 | Ox. (1/2) | — | 299.3 | Method 1 |
| 112 | H | 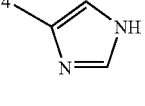 | Ox. (1/2) | — | 297.3 | Method 1 |
| 113 | H | 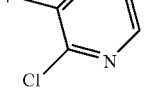 | — | 138-140 | — | Method 2 |
| 114 | H | 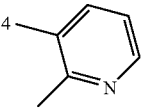 | HCl | — | 324.3 | Method 2 |
| 115 | H | 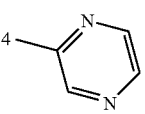 | — | — | 311.3 | Method 2 |
| 116 | H | 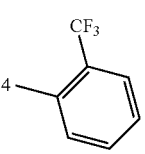 | — | — | 377.2 | Method 1 |
| 117 | H | 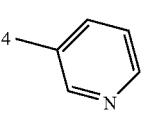 | — | 65-67 | — | Method 1 |
| 118 | H | 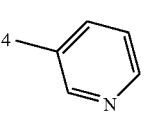 | — | 83 | — | Method 1 |
| 119 | H | 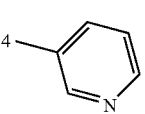 | HCl | 191 | — | Method 9 |

| | | | | | | |
|---|---|---|---|---|---|---|
| 120 | H | 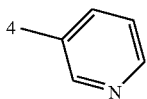 4-(pyridin-3-yl) | HCl | 201 | — | Method 11 |
| 121 | H | 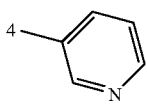 4-(pyridin-3-yl) | HCl | 180 | — | Method 9 |
| 122 | H | 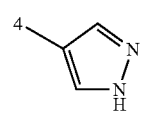 4-(1H-pyrazol-4-yl) | HCl | 145 | — | Method 1 |
| 123 | H | 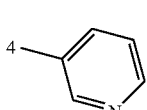 4-(pyridin-3-yl) | HCl | 170 | — | Method 1 |
| 124 | H | 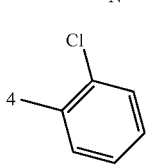 4-(2-chlorophenyl) | — | 111-116 | — | Method 1 |
| 125 | H | 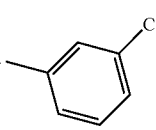 4-(3-chlorophenyl) | — | 53-60 | — | Method 1 |
| 126 | H | 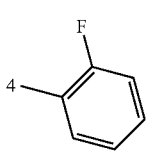 4-(2-fluorophenyl) | — | — | — | Method 1 |
| 127 | H | 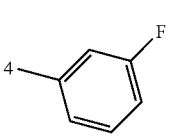 4-(3-fluorophenyl) | — | 108-112 | — | Method 1 |
| 128 | H | 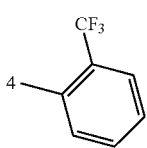 4-(2-trifluoromethylphenyl) | — | 50-55 | — | Method 1 |
| 129 | | 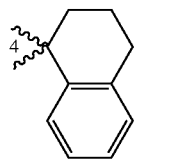 | — | 115-120 | — | Method 1 |
| 130 | H | 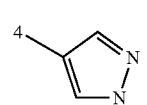 4-(1H-pyrazol-4-yl) | — | 200 | — | Method 1 |
| 131 | H | 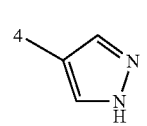 4-(1H-pyrazol-4-yl) | — | 77-95 | — | Method 1 |

TABLE-continued

| | | | | | | |
|---|---|---|---|---|---|---|
| 132 | H | 4-(3-pyridyl) | HCl | 196-198 | — | Method 1 |
| 133 | H | 4-(1H-pyrazol-4-yl) | — | 183 | — | Method 1 |
| 134 | H | 4-(1H-pyrazol-4-yl) | — | 73 | — | Method 1 |
| 135 | H | 4-(1H-pyrazol-4-yl) | — | — | 323.3 | Method 1 |
| 136 | H | 4-(2-chlorophenyl) | — | — | 369.4 | Method 1 |
| 137 | H | 4-(2-methoxycarbonylphenyl) | — | — | 367.3 | Method 1 |
| 138 | 4-OMe | 4-(3-pyridyl) | Fum. (3.5/1) | 205 | — | Method 1 |
| 139 | H | 4-(2-methoxy-3-pyridyl) | — | — | 340.3 | Method 2 |
| 140 | H | 4-(1H-pyrazol-4-yl) | — | 211 | — | Method 1 |
| 141 | H | 4-(1H-pyrazol-4-yl) | — | — | 351.4 | Method 1 |
| 142 | H | 4-(1H-pyrazol-4-yl) | — | 57-65 | — | Method 1 |
| 143 | H | 4-(1H-pyrazol-4-yl) | — | 52-60 | — | Method 1 |
| 144 | H | 4-(2-trifluoromethylphenyl) | — | 52-60 | — | Method 1 |

| | | | | | | |
|---|---|---|---|---|---|---|
| 145 | H | 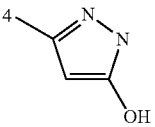 | — | 226-230 | — | Method 1 |
| 146 | H | 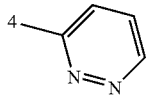 | — | — | 337.4 | Method 2 |
| 147 | H | 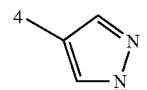 | — | 69 | — | Method 1 |
| 148 | H | 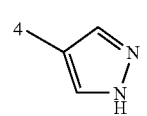 | HCl | 108-110 | — | Method 10 |
| 149 | |  | — | — | 301.4 | Method 1 |
| 150 | H | 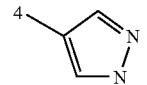 | Fum. (1/1.3) | 83 | — | Method 1 |
| 151 | H | 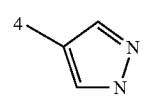 | — | — | 313.4 | Method 1 |
| 152 | H | 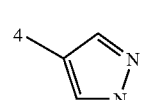 | Fum. | — | 411.4 | Method 1 |
| 153 | H | 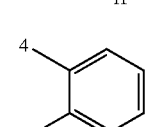 | — | — | 403.3 | Method 1 |
| 154 | H | 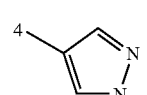 | — | 50-57 | — | Method 1 |
| 155 | H | 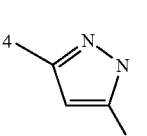 | — | — | 315.4 | Method 1 |
| 156 | H | 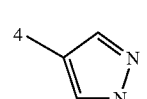 | — | — | 380.3 | Method 1 |
| 157 | H | 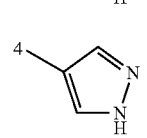 | — | — | 418.3 | Method 1 |

| | | | | | | |
|---|---|---|---|---|---|---|
| 158 | H | 4-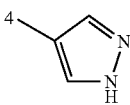 | — | 154-156 | 457.3 | Method 1 |
| 159 | H | 4-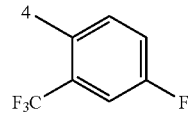 | — | — | 395.2 | Method 1 |
| 160 | 4-OH | 4-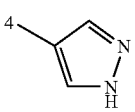 | — | 122 | 429.2 | Method 15 |
| 161 | H | 4-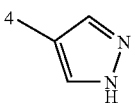 | — | 239 | 466.3 | Method 15 |
| 162 | H | 4-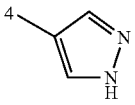 | — | 174 | 413.3 | Method 15 |
| 163 | H | 4-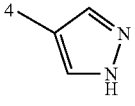 | Fum | — | 356.3 | Method 1 |
| 164 | H | 4-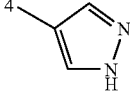 | — | 176 | 388.3 | Method 15 |
| 165 | 4-OH | 4-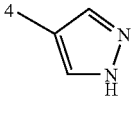 | — | 153 | 315.3 | Method 1 |
| 166 | H | 4-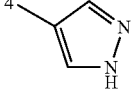 | — | 170-172 | 298.3 | Method 1 |
| 167 | H | 4-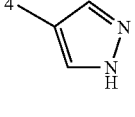 | HCl | 97 | 334.3 | Method 1 |
| 168 | H | 4-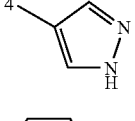 | — | 210 | 414.3 | Method 15 |
| 169 | | 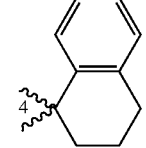 | HCl | 168-172 | 348.4 | Method 1 |
| 170 | H | 4-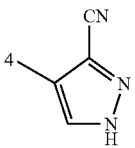 | — | — | 324.3 | Method 2 |

| | | | | | | |
|---|---|---|---|---|---|---|
| 171 | H | 4-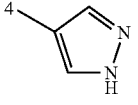 | — | 120 | 471.3 | Method 14 |
| 172 | H | 4-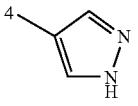 | — | 251 | 500.4 | Method 14 |
| 173 | H | 4-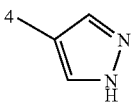 | — | 78 | 471.4 | Method 14 |
| 174 | H | 4-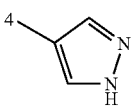 | — | 94 | 487.3 | Method 14 |
| 175 | H | 4-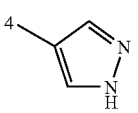 | — | 72 | 500.4 | Method 14 |
| 176 | H | 4-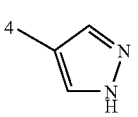 | — | 105 | 471.3 | Method 14 |
| 177 | H | 4-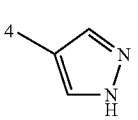 | — | 82-90 | 522.2 | Method 1 |
| 178 | H | 4-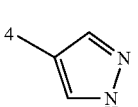 | — | 100 | 487.4 | Method 14 |
| 179 | H | 4-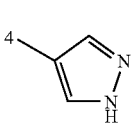 | — | 95 | 467.3 | Method 1 |
| 180 | H | 4-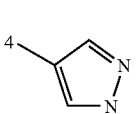 | — | 95 | 487.4 | Method 14 |
| 181 | H | 4-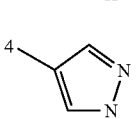 | — | 85 | 487.4 | Method 1 |
| 182 | H | 4-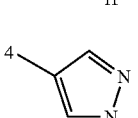 | — | 85 | 453.1 | Method 1 |
| 183 | H | 4-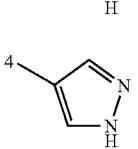 | — | — | 359.3 | Method 1 |

| | | | | | | |
|---|---|---|---|---|---|---|
| 184 | H | 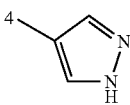 4-pyrazole | — | 55-62 | 355.3 | Method 1 |
| 185 | H | 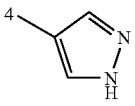 4-pyrazole | — | 65 | 367 | Method 1 |
| 186 | H | 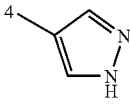 4-pyrazole | — | 81 | 399.3 | Method 1 |
| 187 | H | 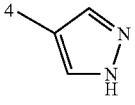 4-pyrazole | — | — | 417.3 | Method 14 |
| 188 | H | 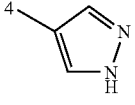 4-pyrazole | — | 90 | 418.3 | Method 14 |
| 189 | H | 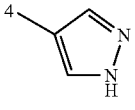 4-pyrazole | — | 226-229 | 446.3 | Method 15 |
| 190 | H | 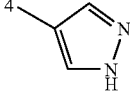 4-pyrazole | — | 81 | 400.3 | Method 1 |
| 191 | H | 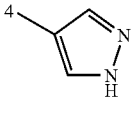 4-pyrazole | — | 211 | 389.3 | Method 15 |
| 192 | H | 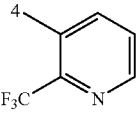 | — | 73 | 378.3 | Method 2 |
| 193 | H | 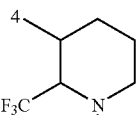 | — | 150 | 384.3 | Method 2 |
| 194 | H | 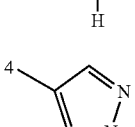 4-pyrazole | — | 85 | 443.3 | Method 1 |
| 195 | H | 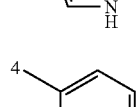 | — | 146 | 477.3 | Method 1 |
| 196 | H | 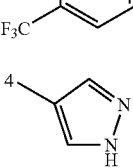 4-pyrazole | — | 136 | 389.3 | Method 15 |

TABLE-continued
| | | | | | | |
|---|---|---|---|---|---|---|
| 197 | H | 4-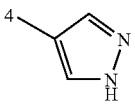 | — | 243 | 456.3 | Method 15 |
| 198 | H | 4-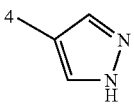 | — | 80 | 333.3 | Method 1 |
| 199 | H | 4-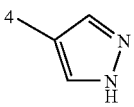 | — | 244 | 432.3 | Method 14 |
| 200 | H | 4-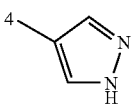 | — | 210 | 455.3 | Method 15 |
| 201 | H | 4-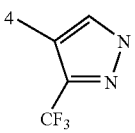 | — | 90 | 367.2 | Method 2 |
| 202 (S) | H | 4-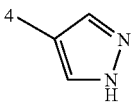 | — | 185 | 399.3 | Method 1 |
| 203 | H | 4-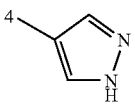 | — | 185 | 399.3 | Method 1 |
| 204 | H | 4-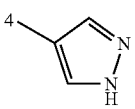 | — | 247 | 453.2 | Method 14 |
| 205 | H | 4-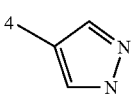 | Fum. | 76 | 447.3 | Method 15 |
| 206 | H | 4-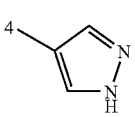 | — | 230 | 471.3 | Method 14 |
| 207 | H | 4-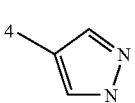 | — | 111 | 535.3 | Method 14 |
| 208 | H | 4-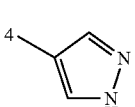 | — | 12 | 508.3 | Method 14 |
| 209 | H | 4-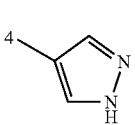 | — | 108 | 547.3 | Method 14 |

TABLE-continued

| 210 | H | 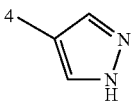 | — | 100 | 457.3 | Method 14 |

The compounds according to the invention formed the subject of pharmacological tests which make it possible to determine their inhibiting effect on the 11β-HSD1 enzyme, which is an enzyme which is involved in the metabolism of lipids or the metabolism of glucose.

These tests consisted in measuring the in vitro inhibiting activity of the compounds of the invention by virtue of an SPA (Scintillation Proximity Assay) test in 384-well format. The recombinant 11β-HSD1 protein was produced in the yeast S. cerevisiae. The reaction was carried out by incubating the enzyme in the presence of $^3$H-cortisone and of NADPH, in the absence or in the presence of an increasing concentration of inhibitor. SPA beads coupled to an antimouse antibody, which are preincubated with anticortisol antibody, made it possible to measure the amount of cortisol formed during the reaction.

The inhibiting activity with regard to the enzyme 11β-HSD1 is given by the concentration which inhibits 50% of the activity of 11β-HSD1 ($IC_{50}$).

The $IC_{50}$ values of the compounds according to the invention are less than 1 μM. For example, the $IC_{50}$ values of the compounds Nos. 4, 7, 18, 78, 101, 162 and 188 are respectively 0.115 μM, 0.230 μM, 0.043 μM, 0.039 μM, 0.09 μM, 0.057 μM and 0.130 μM.

It thus appears that the compounds according to the invention have an inhibiting activity for the enzyme 11β-HSD1. The compounds according to the invention can thus be used in the preparation of medicaments, in particular of medicaments which inhibit the enzyme 11β-HSD1.

Thus, according to another of its aspects, a subject matter of the invention is medicaments which comprise a compound of formula (I) or an addition salt of the latter with a pharmaceutically acceptable acid or also a hydrate or a solvate of the compound of formula (I).

These medicaments are employed therapeutically, in particular in the treatment of obesity, diabetes, insulin resistance, the metabolic syndrome, Cushing's syndrome, hypertension, atherosclerosis, cognition and dementia, glaucoma, osteoporosis and some infectious diseases by increasing the effectiveness of the immune system.

According to another of its aspects, the present invention relates to pharmaceutical compositions comprising, as active principle, a compound according to the invention. These pharmaceutical compositions comprise an effective dose of at least one compound according to the invention or a pharmaceutically acceptable salt, a hydrate or a solvate of said compound, and at least one pharmaceutically acceptable excipient.

Said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and to human beings, for the prophylaxis or the treatment of the above disorders or diseases.

The appropriate unit administration forms comprise oral forms, such as tablets, soft or hard gelatin capsules, powders, granules and oral solutions or suspensions, sublingual, buccal, intratracheal, intraocular or intranasal administration forms, forms for administration by inhalation, topical, transdermal, subcutaneous, intramuscular or intravenous administration forms, rectal administration forms and implants. For topical application, the compounds according to the invention can be used in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The present invention, according to another of its aspects, also relates to a method for the treatment of the pathologies indicated above which comprises the administration, to a patient, of an effective dose of a compound according to the invention or one of its pharmaceutically acceptable salts or its hydrates or solvates.

We claim:
1. A compound of formula (I):

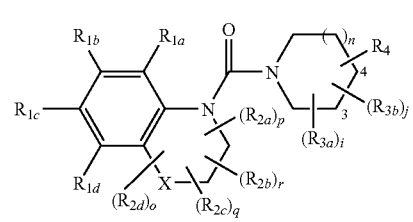

wherein:
X is $NR_{2a}$, $NR_{2b}$, $NR_{2c}$ or $NR_{2d}$;
$R_{1a}$, $R_{1b}$, $R_{1c}$, $R_{1d}$, $R_{2a}$, $R_{2b}$, $R_{2c}$ and $R_{2d}$ are, independently, hydrogen, halogen, $(C_1-C_5)$alkyl, $(C_1-C_5)$alkoxy, $(C_1-C_5)$haloalkyl, hydroxyl, hydroxy$(C_1-C_5)$alkyl, cyano, —$COOR_5$, —$NR_6R_7$, $R_5OOC$—$(C_1-C_5)$alkyl, $R_6R_7N$—$(C_1-C_5)$alkyl, —$CONR_6R_7$, $R_6R_7NCO$—$(C_1-C_5)$alkyl, —$SO_2NR_6R_7$, —$COR_5$, aryl, heteroaryl, aryl$(C_1-C_5)$alkyl, heteroaryl$(C_1-C_5)$alkyl or heterocycloalkyl$(C_1-C_5)$alkyl, wherein the aryl or heteroaryl moiety is optionally substituted by 1 to 3 times by cyano, $COOR_5$, $CONR_6R_7$, $SO_2R_5$, $(C_1-C_5)$alkoxy, $OCH_2CONR_6R_7$, halogen, or $(C_1-C_5)$haloalkyl, and when one or more of $R_{1a}$, $R_{1b}$, $R_{1c}$, $R_{1d}$, $R_{2a}$, $R_{2b}$, R$_{2c}$ and R$_{2d}$ are aryl(C$_1$-C$_5$)alkyl, then one of the aryl (C$_1$-C$_5$)alkyl is additionally optionally substituted by heteroaryl;

R$_{3a}$ and R$_{3b}$ are, independently, hydrogen, fluorine, (C$_1$-C$_5$)alkyl, (C$_1$-C$_5$)alkoxy, alkoxy(C$_1$-C$_5$)alkyl, hydroxyl, hydroxy(C$_1$-C$_5$)alkyl, (C$_1$-C$_5$)haloalkyl, cyano, —COOR$_5$, —NR$_6$R$_7$, R$_5$OOC—(C$_1$-C$_5$)alkyl, R$_6$R$_7$N—(C$_1$-C$_5$)alkyl, —CONR$_6$R$_7$ or R$_6$R$_7$NCO—(C$_1$-C$_5$)alkyl;

R$_4$ is (C$_1$-C$_5$)alkyl, (C$_3$-C$_6$)cycloalkyl, heterocycloalkyl, mono- or bicyclic aryl having from 5 to 10 carbon atoms, or mono- or bicyclic heteroaryl having from 2 to 9 carbon atoms, wherein when R$_4$ is aryl, heteroaryl or heterocycloalkyl, it is optionally substituted by 1 to 4 times by halogen, (C$_1$-C$_5$)alkyl, (C$_1$-C$_5$)alkoxy, (C$_1$-C$_5$)haloalkyl, hydroxyl, hydroxy(C$_1$-C$_5$)alkyl, (C$_1$-C$_5$)alkoxy (C$_1$-C$_5$)alkyl, cyano, optionally substituted phenyl, optionally substituted benzyl, —COOR$_5$, —NR$_6$R$_7$, R$_5$OOC—(C$_1$-C$_5$)alkyl, R$_6$R$_7$N—(C$_1$-C$_5$)alkyl, —CONR$_6$R$_7$ or —SO$_2$NR$_6$R$_7$, or when two of R$_{3a}$, R$_{3b}$ and R$_4$ are carried by the same carbon atom, they can form together with the carbon atom to which they are attached a spiro ring of formula a), b), c) or d):

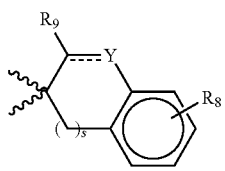
a)

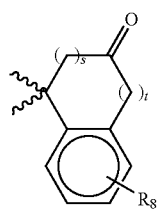
b)

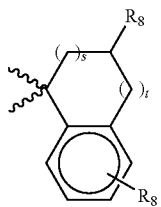
c)

d)

wherein:

---- is a single bond or a double bond;

s is 0, 1, 2 or 3, t is 0, 1, 2 or 3, provided that s and t are not 0 at the same time;

R$_8$ is hydrogen, halogen, (C$_1$-C$_5$)alkyl, (C$_1$-C$_5$)alkoxy, trifluoromethyl, hydroxyl, hydroxymethyl, cyano, —COOR$_5$, or —NR$_6$R$_7$;

R$_9$ is hydrogen, (C$_1$-C$_5$)alkyl or hydroxyl;

Y is a bond, carbon or nitrogen;

n is 0 or 1;

o, p, q and r are, independently, 0, 1 or 2;

i and j are 0, 1, 2, 3 or 4;

R$_5$ is hydrogen, (C$_1$-C$_5$)alkyl, (C$_3$-C$_6$)cycloalkyl, or halo(C$_1$-C$_5$)alkyl; and R$_6$ and R$_7$ are, independently, hydrogen, (C$_1$-C$_5$)alkyl, (C$_3$-C$_6$)cycloalkyl, (C$_1$-C$_5$)alkylcarbonyl, hydroxymethyl(C$_1$-C$_5$)alkyl, (C$_1$-C$_5$)alkoxymethyl (C$_1$-C$_5$)alkyl, aryl, optionally substituted heterocycloalkyl, or —SO$_2$R$_5$, or R$_6$ and R$_7$, taken together with the nitrogen atom to which they are attached, form an optionally substituted heterocycloalkyl;

or a pharmaceutically acceptable acid addition salt thereof.

2. The compound according to claim 1, wherein:

R$_{3a}$, R$_{3b}$ and R$_4$ are carried by different carbon atoms;

or a pharmaceutically acceptable acid addition salt thereof.

3. The compound according to claim 1, wherein:

two of R$_{3a}$, R$_{3b}$ and R$_4$ are carried by the same carbon atom but do not form a spiro group;

or a pharmaceutically acceptable acid addition salt thereof.

4. The compound according to claim 1, wherein:

R$_{1a}$, R$_{1b}$, R$_{1c}$, R$_{1d}$, R$_{2a}$, R$_{2b}$, R$_{2c}$ and R$_{2d}$ are, independently, hydrogen, halogen, (C$_1$-C$_5$)alkyl, (C$_1$-C$_5$)alkoxy, (C$_1$-C$_5$)haloalkyl, hydroxyl or hydroxy(C$_1$-C$_5$)alkyl, —COOR$_5$, —CONR$_6$R$_7$, —SO$_2$NR$_6$R$_7$, —COR$_5$, aryl, heteroaryl, aryl(C$_1$-C$_5$)alkyl, heteroaryl (C$_1$-C$_5$)alkyl or heterocycloalkyl(C$_1$-C$_5$)alkyl, wherein the aryl or heteroaryl moiety is optionally substituted by 1 to 3 times by cyano, COOR$_5$, CONR$_6$R$_7$, SO$_2$R$_5$, (C$_1$-C$_5$)alkoxy, OCH$_2$CONR$_6$R$_7$, halogen, or (C$_1$-C$_5$) haloalkyl, and when one or more of R$_{1a}$, R$_{1b}$, R$_{1c}$, R$_{1d}$, R$_{2a}$, R$_{2b}$, R$_{2c}$ and R$_{2d}$ are aryl(C$_1$-C$_5$)alkyl, then one of the aryl(C$_1$-C$_5$)alkyl is additionally optionally substituted by heteroaryl;

R$_{3a}$ and R$_{3b}$ are hydrogen;

R$_4$ is (C$_1$-C$_5$)alkyl, (C$_3$-C$_6$)cycloalkyl, heterocycloalkyl, a monocyclic aryl group having from 5 to 6 carbon atoms, or a monocyclic heteroaryl group having from 2 to 5 carbon atoms, wherein when R$_4$ is aryl, heteroaryl, or heterocycloalkyl, it is optionally substituted by 1 to 2 times by halogen, (C$_1$-C$_5$)alkyl, (C$_1$-C$_5$)alkoxy, (C$_1$-C$_5$)haloalkyl, hydroxyl, cyano, optionally substituted phenyl, optionally substituted benzyl, or —CONR$_6$R$_7$;

o, p, q and r are, independently, 0 or 1;

i and j are 0 or 1;

R$_5$ is hydrogen or (C$_1$-C$_5$)alkyl; and

R$_6$ and R$_7$ are, independently, hydrogen, (C$_1$-C$_5$)alkyl, (C$_3$-C$_6$)cycloalkyl or heterocycloalkyl, or R$_6$ and R$_7$, taken together with the nitrogen atom to which they are attached, form an optionally substituted heterocycloalkyl;

or a pharmaceutically acceptable acid addition salt thereof.

5. The compound according to claim 1, wherein:

R$_{1a}$, R$_{1b}$, R$_{1c}$, R$_{1d}$, R$_{2a}$, R$_{2b}$, R$_{2c}$ and R$_{2d}$ are, independently, hydrogen, halogen, (C$_1$-C$_5$)alkyl, (C$_1$-C$_5$) alkoxy, (C$_1$-C$_5$)haloalkyl, hydroxyl, hydroxy(C$_1$-C$_5$) alkyl, —COOR$_5$, —CONR$_6$R$_7$, —SO$_2$NR$_6$R$_7$, —COR$_5$, aryl, heteroaryl, aryl(C$_1$-C$_5$)alkyl, heteroaryl (C$_1$-C$_5$)alkyl or heterocycloalkyl(C$_1$-C$_5$)alkyl, wherein the aryl or heteroaryl moiety is optionally substituted by 1 to 3 times by cyano, COOR$_5$, CONR$_6$R$_7$, SO$_2$R$_5$, (C$_1$-C$_5$)alkoxy, OCH$_2$CONR$_6$R$_7$, halogen, or (C$_1$-C$_5$) haloalkyl, and when one or more of R$_{1a}$, R$_{1b}$, R$_{1c}$, R$_{1d}$, R$_{2a}$, R$_{2b}$, R$_{2c}$ and R$_{2d}$ are aryl(C$_1$-C$_5$)alkyl, then one of the aryl(C$_1$-C$_5$)alkyl is additionally optionally substituted by heteroaryl;

R$_{3a}$ and R$_{3b}$ are hydrogen or hydroxyl;

R$_4$ is (C$_1$-C$_5$)alkyl, (C$_3$-C$_6$)cycloalkyl, heterocycloalkyl, a monocyclic aryl group having from 5 to 6 carbon atoms, or a monocyclic heteroaryl group having from 2 to 5 carbon atoms, wherein when R$_4$ is aryl, heteroaryl or heterocycloalkyl, it is optionally substituted by 1 to 2 times by halogen, (C$_1$-C$_5$)alkyl, (C$_1$-C$_5$)alkoxy, (C$_1$-C$_5$)haloalkyl, hydroxyl, cyano, optionally substituted phenyl, optionally substituted benzyl, or —CONR$_6$R$_7$;

o, p, q and r are, independently, 0 or 1;

i and j are 0 or 1;

R$_5$ is hydrogen, or (C$_1$-C$_5$)alkyl; and

R$_6$ and R$_7$ are, independently, hydrogen, (C$_1$-C$_5$)alkyl, (C$_3$-C$_6$)cycloalkyl or heterocycloalkyl, or R$_6$ and R$_7$, taken together with the nitrogen atom to which they are attached, form an optionally substituted heterocycloalkyl;

or a pharmaceutically acceptable acid addition salt thereof.

6. The compound according to claim 1 of formula

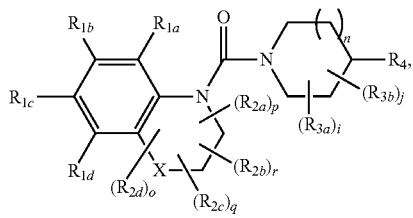

wherein:

p and r are 1;

o and q are 0;

i and j are 1 or 2;

n is 0 or 1;

R$_{1a}$, R$_{1b}$, R$_{1c}$, and R$_{1d}$ are hydrogen, or one of R$_{1a}$, R$_{1b}$, R$_{1c}$, and R$_{1d}$ is halogen and the others are hydrogen;

R$_{2a}$ and R$_{2b}$ are hydrogen, or one of R$_{2a}$ and R$_{2b}$ is (C$_1$-C$_5$) alkyl, and the other is hydrogen;

R$_{3a}$ and R$_{3b}$ are hydrogen; and

R$_4$ is pyridine, pyrazine, pyrazole, oxadiazole, thiazole, or imidazole;

or a pharmaceutically acceptable acid addition salt thereof.

7. The compound according to claim 1 of formula

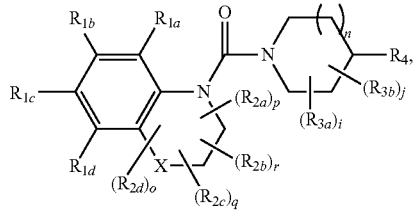

wherein:

n is 0; and

R$_4$ is pyrazole or pyridine;

or a pharmaceutically acceptable acid addition salt thereof.

8. The compound according to claim 1 of formula

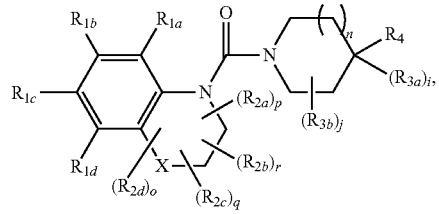

wherein:

n is 0 or 1;

i is 1; and

R$_{3a}$ is cyano or (C$_1$-C$_5$)alkoxy;

or a pharmaceutically acceptable acid addition salt thereof.

9. The compound according to claim 1 of formula

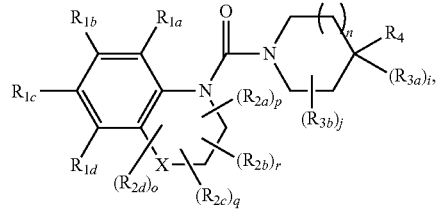

wherein:

R$_{1a}$, R$_{1b}$, R$_{1c}$, R$_{1d}$, R$_{2a}$, R$_{2b}$, R$_{2c}$ and R$_{2d}$ are hydrogen;

i is 1; and

R$_{3a}$ and R$_4$ together with the carbon atom to which they are attached, form one of the following optionally substituted groups at the spiro position:

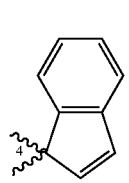 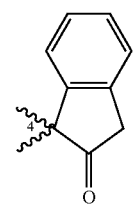

-continued

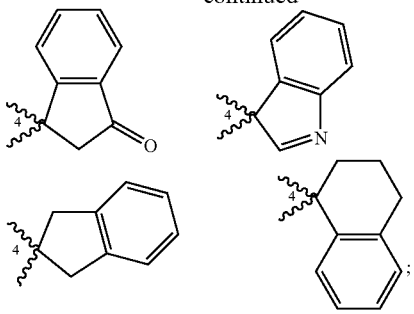

or a pharmaceutically acceptable acid addition salt thereof.

10. The compound according to claim 1 of formula

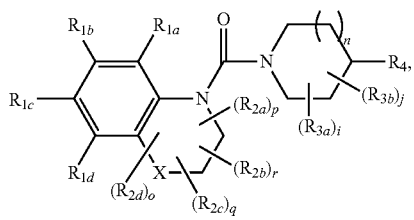

wherein:
n is 0;
p is 1;
r, q and o are 0;
$R_{2a}$ is carried by X, and is aryl optionally substituted by $CONR_6R_7$ or $OCH_2CONR_6R_7$; and
$R_4$ is pyrazole or pyridine;
or a pharmaceutically acceptable acid addition salt thereof.

11. A process for preparing the compound according to claim 1, comprising reacting a compound of formula (IV):

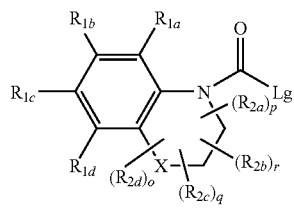

(IV)

wherein $R_{1a}$, $R_{1b}$, $R_{1c}$, $R_{1d}$, $R_{2a}$, $R_{2b}$, $R_{2c}$, $R_{2d}$, o, p, q and r are as defined in claim 1, and Lg is a leaving group, with a compound of formula (V)

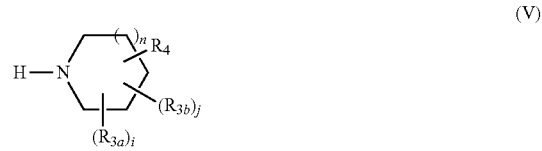

(V)

wherein i, j, n, $R_{3a}$, $R_{3b}$ and $R_4$ are as defined in claim 1, optionally in the presence of a base at a temperature varying from ambient temperature to 100° C.

12. A process for preparing the compound according to claim 1, comprising hydrogenating a compound of formula (XV):

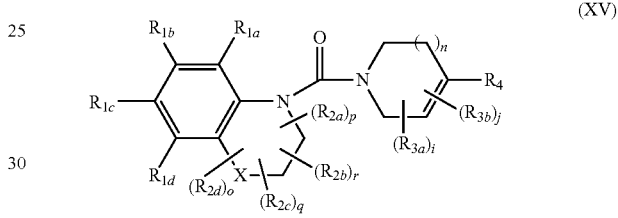

(XV)

wherein i, j, n, o, p, q, r, $R_{1a}$, $R_{1b}$, $R_{1c}$, $R_{1d}$, $R_{2a}$, $R_{2b}$, $R_{2c}$, $R_{2d}$, $R_{3a}$, $R_{3b}$ and $R_4$ are as defined in claim 1.

13. A process for preparing the compound according to claim 1, wherein $R_{3a}$ and $R_4$ are at the 4-position, and $R_{3a}$ is cyano, comprising reacting a compound of formula (XX):

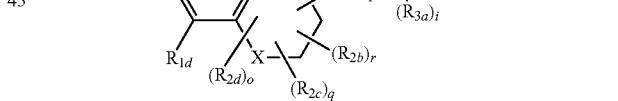

(XX)

wherein j, n, o, p, q, r, $R_{1a}$, $R_{1b}$, $R_{1c}$, $R_{1d}$, $R_{2a}$, $R_{2b}$, $R_{2c}$, $R_{2d}$ and $R_{3b}$ are as defined in claim 1,
with a compound of formula (XXI) Lg-$R_4$ wherein $R_4$ is as defined in claim 1, and Lg is a leaving group.

* * * * *